US010925950B2

(12) United States Patent
Murphy et al.

(10) Patent No.: US 10,925,950 B2
(45) Date of Patent: Feb. 23, 2021

(54) IMMUNOGENIC COMPOSITIONS, ANTIGEN SCREENING METHODS, AND METHODS OF GENERATING IMMUNE RESPONSES

(71) Applicant: UNIVERSITY OF WASHINGTON, Seattle, WA (US)

(72) Inventors: Sean C. Murphy, Seattle, WA (US); Brad Stone, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 0 days.

(21) Appl. No.: 15/749,928

(22) PCT Filed: Aug. 3, 2016

(86) PCT No.: PCT/US2016/045439
§ 371 (c)(1),
(2) Date: Feb. 2, 2018

(87) PCT Pub. No.: WO2017/024084
PCT Pub. Date: Feb. 9, 2017

(65) Prior Publication Data
US 2018/0221464 A1 Aug. 9, 2018

Related U.S. Application Data

(60) Provisional application No. 62/200,487, filed on Aug. 3, 2015.

(51) Int. Cl.
A61K 48/00 (2006.01)
A61K 39/015 (2006.01)
A61K 47/69 (2017.01)
A61P 33/06 (2006.01)
A61K 45/06 (2006.01)
C07K 14/15 (2006.01)
A61K 39/00 (2006.01)

(52) U.S. Cl.
CPC ............ A61K 39/015 (2013.01); A61K 45/06 (2013.01); A61K 47/6921 (2017.08); A61P 33/06 (2018.01); C07K 14/15 (2013.01); A61K 2039/5154 (2013.01); A61K 2039/53 (2013.01); A61K 2039/545 (2013.01); Y02A 50/30 (2018.01)

(58) Field of Classification Search
CPC .................................................. A61K 39/015
See application file for complete search history.

(56) References Cited

U.S. PATENT DOCUMENTS 7,253,333 B2 * 8/2007 Tanaka ............... A01K 67/0339
800/10
2003/0157534 A1 8/2003 Engelhorn et al.
2005/0208078 A1 * 9/2005 Hoffman ................. A61P 33/06
424/272.1
2005/0266017 A1 * 12/2005 Druilhe ................ C07K 14/445
424/191.1
2006/0051348 A1 3/2006 Gorlach et al.
2006/0094649 A1 * 5/2006 Keogh .................... C07K 14/71
424/185.1
2009/0274726 A1 11/2009 Brett et al.
2011/0184160 A1 7/2011 Weiner et al.

FOREIGN PATENT DOCUMENTS

WO 9631613 A1 10/1996
WO 9941383 A1 8/1999
WO 2005025614 A2 3/2005

OTHER PUBLICATIONS

Aguiar, JC, et al. "Discovery of Novel Plasmodium falciparum Pre-Erythrocytic Antigens for Vaccine Development" PLoS One, Aug. 20, 2015, 10(8). 24 pages.
Arrington, J. et al. "Plasmid Vectors Encoding Cholera Toxin or the Heat-Labile Enterotoxin from *Escherichia coli* Are Strong Adjuvants for DNA Vaccines" Journal of Virology, May 2002, vol. 76, No. 9, pp. 4536-4546.
Barth, S. et al. "Autophagy: Assays and Artifacts" Journal of Pathology, Jun. 2010, 221(2) pp. 117-124.
Bergmann-Leitner, Elke S et al. "Immunization with Pre-Erythrocytic Antigen CelTOS from Plasmodium Falciparum Elicits Cross-Species Protection against Heterologous Challenge with Plasmodium Berghei." PLoS One, Aug. 2010, 5(8), e12294, 9 pages.
Braeckel-Budimir et al. "Highly focused TCR Vβ repertoire is associated with a large number of naive precursors and robust CD8 T cell responses specific for a Plasmodium antigen" Journal of Immunology, May 2015, vol. 194, Supplement 1, 4 pages.
Braeckel-Budimir, N. et al. "CD8T-cell-mediated protection against liver-stage malaria: lessons from a mouse model" Frontiers in Microbiology, Jun. 2014, vol. 5, 9 pages.

(Continued)

Primary Examiner — Albert M Navarro
(74) Attorney, Agent, or Firm — Perkins Coie LLP; Lara J. Dueppen

(57) ABSTRACT

An immunogenic composition is provided herein. The immunogenic compositions are used to identify and select immunogenic antigens that elicit immune responses in a subject and may be subsequently used in multi-antigen vaccine compositions against one or more diseases or conditions. According to some embodiments, the immunogenic composition may include a plurality of nucleic acid fragments or minigenes derived from a nucleic acid library, wherein each nucleic acid fragment encodes a different antigen or functional portion thereof, and wherein the different antigens or functional portions thereof are associated with one or more disease or condition. The immunogenic composition may also include a delivery medium loaded with the plurality of nucleic acid fragments and in some embodiments, the delivery medium is loaded with nucleic acid fragments in such a way that individual antigen presenting cells receive only a subset of the nucleic acids within a vaccine in order to minimize antigenic competition.

14 Claims, 18 Drawing Sheets

(56) References Cited

OTHER PUBLICATIONS

Canakoglu, Nurettin et al. "Immunization of Knock-Out A/β Interferon Receptor Mice against High Lethal Dose of Crimean-Congo Hemorrhagic Fever Virus with a Cell Culture Based Vaccine." PLoS Neglected Tropical Diseases, Mar. 11, 2015, 14 pages.
Cardile, AP, et al. Monitoring Exposure to Ebola and Health of U.S. Military Personnel Deployed in Support of Ebola Control Efforts—Liberia, Oct. 25, 2014-Feb. 27, 2015. MMWR Morbidity and Mortality Weekly Report. 2015;64(25):690-694.
De Filette, Marina et al. "Vaccination of Mice Using the West Nile Virus E-Protein in a DNA Prime-Protein Boost Strategy Stimulates Cell-Mediated Immunity and Protects Mice against a Lethal Challenge." PLoS One, Feb. 2014, 9(2), e87837, 10 pages.
Dobano, C et al. "Targeting antigen to MHC Class I and Class II antigen presentation pathways for malaria DNA vaccines" Immunology Letters, 2007, vol. 111, pp. 92-102.
Doll, K. et al. "Protective capacity of CD8 T cells targeting aspectrum of Plasmodium-specific epitopes (MPF6P.735)" Jounal of Immunology, May 2014, vol. 192, Supplement 1, 5 pages.
Doolan, D. et al. "Circumventing genetic restriction of protection against malaria with multigene DNA immunization: CD8+ cell-, interferon gamma-, and nitric oxide-dependent immunity" Journal of Experimental Medicine, 1996, 183(4), pp. 1739-1746.
Doolan, D. et al. "Identification of Plasmodium falciparum antigens by antigenic analysis of genomic and proteomic data." Proc Natl Acad Sci USA. Aug. 19, 2003, 100(17) pp. 9952-9957.
Doolan, D. et al. "The Complexity of Protective Immunity Against Liver-Stage Malaria" J Immunol Aug. 1, 2000, 165 (3) pp. 1453-1462.
Duffy, P. et al. "Pre-erythrocytic malaria vaccines: identifying the targets" Expert Rev Vaccines. Oct. 2012;11(10):pp. 1261-1280.
Dunachie, S.J. et al. "A DNA Prime-Modified Vaccinia Virus Ankara Boost Vaccine Encoding Thrombospondin-Related Adhesion Protein but Not . . . " Infection and Immunity, Oct. 2006, 74(10), pp. 5933-5942.
Epstein, J.E. et al. "Live Attenuated Malaria Vaccine Designed to Protect Through Hepatic CD8+ T Cell Immunity" Science, Oct. 28, 2011, vol. 334; pp. 475-480.
Ferraro, B., et al. "Inducing humoral and cellular responses to multiple sporozoite and liver-stage malaria antigens using exogenous plasmid DNA" Infect Immun. Oct. 2013; 81(10):pp. 3709-3720.
Fidock, D. et al. "Cloning and characterization of a novel Plasmodium falciparum sporozoite surface antigen, STARP" Molecular and Biochemical Parasitology, 1994, vol. 64, pp. 219-232.
Frevert, U. et al. "Plasmodium cellular effector mechanisms and the hepatic microenvironment" Frontiers in Microbiology, May 27, 2015; vol. 6; 19 pages.
Friedrich, TC. et al. "Subdominant CD8+ T-cell responses are involved in durable control of AIDS virus replication" J. Virology; Apr. 2007; 81(7); pp. 3465-3476.
From the Centers for Disease Control and Prevention, "Dengue fever among U.S. military personnel—Haiti, Sep.-Nov. 1994" JAMA, 1995, vol. 273, No. 1, pp. 14-15.
Fu, T-M. et al. "Induction of MHC class I-restricted CTL response by DNA immunization with ubiquitin-influenza virus nucleoprotein fusion antigens" Vaccine, 1998, vol. 16, No. 18, pp. 1711-1717.
Fuller, D. et al. "Therapeutic DNA Vaccine Induces Broad T Cell Responses in the Gut and Sustained Protection from Viral Rebound and AIDS in SIV-Infected Rhesus Macaques" PLoS One; Mar. 2012; 7(3); e33715; 16 pages.
Gibbons, RV. et al. "Dengue and US military operations from the Spanish-American War through today" Emerg Infect Dis. Apr. 2012;18(4) pp. 623-630.
Goicochea, MA. et al. "Evaluation of Lassa virus vaccine immunogenicity in a CBA/J-ML29 mouse model" Vaccine. Feb. 14, 2012; 30(8):pp. 1445-1452.

Goldwich, A. et al. "Targeting HIV-1 Gag into the Defective Ribosomal Product Pathway Enhances MHC Class I Antigen Presentation and CD8+ T Cell Activation" J Immunol; Jan. 1, 2008, 180(1) pp. 372-382.
Guerin-Marchand, C. et al. "A Liver-stage-specific antigen of Plasmodium falciparum characterized by gene cloning" Nature, Sep. 1987, vol. 329, pp. 164-167.
Guo, H. et al. "Immunodominant Epitopes Mapped by Synthetic Peptides on the Capsid Protein of Avian Hepatitis E Virus Are Non-Protective" Viral Immunology, 2008, vol. 21, No. 1, pp. 61-67.
Hassan, I. A. et al. "Immunological response and protection of mice immunized with plasmid encoding Toxoplasma gondii glycolytic enzyme malate dehydrogenase" Parasite Immunology, 2014, vol. 36, pp. 674-683.
Hiller, N. et al. "A Host-Targeting Signal in Virulence Proteins Reveals a Secretome in Malarial Infection"Science, Dec. 10, 2004; 306(5703); pp. 1934-1937.
Hoffman, SL. et al. "The march toward malaria vaccines" Vaccine. Nov. 27, 2015;33 Suppl 4:D13-23.
Hoffmann, SL. et al. "The march towards malaria vaccines" Am J Prev Med. Dec. 2015;49(6 Suppl 4):S319-33.
Hooper, JW. et al. "DNA Vaccination with Vaccinia Virus L1R and A33R Genes Protects Mice against a Lethal Poxvirus Challenge" Virology. Jan. 20, 2000;266(2):329-39.
Hooper, JW. et al. "Four-gene-combination DNA vaccine protects mice against a lethal vaccinia virus challenge and elicits appropriate antibody responses in nonhuman primates" Virology, 2003, vol. 306, pp. 181-195.
Hospers, G. et al. "Construction of a triple modified p53 containing DNA vaccine to enhance processing and presentation of the p53 antigen" Vaccine 2010, vol. 28, pp. 386-391.
Im, E-J. et al. "Protective Efficacy of Serially Up-Ranked Subdominant CD8+ T Cell Epitopes against Virus Challenges" PLoS Pathogens, May 2011, vol. 7, Issue 5, 13 pages.
Imai, T. et al. "tigen-specific CD8+ T cells induced by the ubiquitin fusion degradation pathway" Biochemical and Biophysical Research Communications 365 (2008) 758-763.
Kariu, T. et al. "CelTOS, a novel malarial protein that mediates transmission to mosquito and vertebrate hosts" Molecular Microbiology, 2006, vol. 59, pp. 1369-1379.
Keitany, G. et al. "Immunization of Mice with Live-Attenuated Late Liver Stage-Arresting Plasmodium yoelii Parasites Generates Protective Antibody Responses to Preerythrocytic Stages of Malaria" Infection & Immunity, Dec. 2014, 82(12), pp. 5143-5153.
Khusmith, S. et al. "Protection Against Malaria by Vaccination with Sporozoite Surface Protein 2 Plus CS Protein" Science, New Series, vol. 252, No. 5006 (May 3, 1991), pp. 715-718.
Kumar, S. et al. "Cytotoxic T cells specific for the circumsporozoite protein of Plasmodium falciparum" Nature, Jul. 1988, vol. 334, pp. 258-260.
Kunwar, R. et al. "Dengue outbreak in a large military station: Have we learnt any lesson?" Medical Journal Armed Forces India, 2015, vol. 71, pp. 11-14.
La Motte, R. et al. "Importance of B7-1-Expressing Host Antigen-Presenting Cells for the Eradication of B7-2 Transfected P815 Tumor Cells" J. Immunol, 1998, vol. 161, pp. 6552-6558.
Lauer, P. et al. "Construction, Characterization, and Use of Two Listeria monocytogenes Site-Specific Phage Integration Vectors" Journal of Bacteriology, Aug. 2002, vol. 184, No. 15, pp. 4177-4186.
Liu, J. et al. "Modulation of DNA Vaccine-Elicited CD8 T-Lymphocyte Epitope Immunodominance Hierarchies" Journal of Virolology, Dec. 2006, vol. 80, No. 24, pp. 11991-11997.
Luke, J. et al. "Improved antibiotic-free DNA vaccine vectors utilizing a novel RNA based plasmid selection system" published in Vaccine, Oct. 2009, vol. 27, No. 46. Author manuscript. 16 pages.
Lundegaard, C. "NetMHC-3.0: accurate web accessible predictions of human, mouse and monkey MHC class I affinities for peptides of length 8-11" Nucleic Acids Research, 2008, vol. 36. W509-W512.
Marti, M. et al. "Targeting Malaria Virulence and Remodeling Proteins to the Host Erythrocyte" Science, Dec. 2004, vol. 306, pp. 1930-1933.

(56) References Cited

OTHER PUBLICATIONS

Mishra, S. et al. "Identification of non-CSP antigens bearing CD8 epitopes in mice immunized with irradiated sporozoites" Vaccine, Oct. 2011, vol. 29, No. 43, pp. 7335-7342.

Moelans, I. et al. "A novel protein antigen of the malaria parasite Plasmodium falciparum, located on the surface of gametes and sporozoites" Molecular and Biochemical Parasitology, 1991, vol. 45, pp. 193-204.

Moorthy, V.S., et al. "Safety of DNA and modified vaccinia virus Ankara vaccines against liver-stage P. falciparum malaria in non-immune volunteers" Vaccine 21 (2003) pp. 1995-2002.

Mueller, A-K. et al. "Genetically modified Plasmodium parasites as a protective experimental malaria vaccine" Nature, Jan. 2005, vol. 433, pp. 164-167 with additional Corrections & Amendments page.

Mullbacher, A. et al. Alloreactive Cytotoxic T-Cell Function, Peptide Nonspecific Scand. J. Immunol. 1999, vol. 49, pp. 563-569.

Murphy, S. et al. "A T-cell response to a liver-stage Plasmodium antigen is not boosted by repeated sporozoite immunizations" PNAS, Apr. 2013, vol. 110, No. 15, pp. 6055-6060.

Nagata, L. et al. "Efficacy of DNA vaccination against western equine encephalitis virus infection" Vaccine 23 (2005) pp. 2280-2283.

Novotny, L. et al. "The Fourth Surface-Exposed Region of the Outer Membrane Protein P5-Homologous Adhesin of Nontypable Haemophilus influenza Is an Immunodominant But Nonprotective Decoying Epitope" J. Immunol., 2003, vol. 171, pp. 1978-1983.

Nussenzweig, R.S. et al. "Protective Immunity produced by the Injection of X-irradiated Sporozoites of Plasmodium berghei" Nature, Oct. 1967, vol. 216. pp. 160-162.

Peng, S. et al. "Cluster intradermal DNA vaccination rapidly induces E7-specific CD8+ T-cell immune responses leading to therapeutic antitumor effects" Gene Therapy (2008) 15, pp. 1156-1166.

Pertmer, T. et al. "Gene gun-based nucleic acid immunization: elicitation of humoral and cytotoxic T lymphocyte responses following epidermal delivery of nanogram quantities of DNA" Vaccine, 1995, vol. 13, No. 15, pp. 1427-1430.

Pinto, A. et al. "Defining New Therapeutics Using a More Immunocompetent Mouse Model of Antibody-Enhanced Dengue Virus Infection" MBio, Sep./Oct. 2015, vol. 6, Issue 5, 13 pages.

Putrianti, E. et al. "Vaccine-like Immunity against Malaria by Repeated Causal-Prophylactic Treatment of Liver-Stage Plasmodium Parasites" The Journal of Infectious Diseases, vol. 199, No. 6 (Mar. 15, 2009), pp. 899-903.

Reed, D. et al. "Combined Alphavirus Replicon Particle Vaccine Induces Durable and Cross-Protective Immune Responses against Equine Encephalitis Viruses" Journal of Virology, Oct. 2014, vol. 88, No. 20. pp. 12077-12086.

Reguzova, A. et al. "Design and Evaluation of Optimized Artificial HIV-1 Poly-T Cell-Epitope Immunogens" PLoS One, Mar. 2015, 18 pages.

Reisler, R. et al. "Immune interference in the setting of same-day administration of two similar inactivated alphavirus vaccines: Eastern equine and western equine encephalitis" Vaccine 30 (2012) pp. 7271-7277.

Richie, T. et al. "Clinical trial in healthy malaria-naïve adults to evaluate the safety, tolerability, immunogenicity and efficacy of MuStDO5 . . . " Human Vaccines & Immunotherapeutics, Nov. 2012, 8(11), pp. 1564-1584.

Robson, K. et al. "A highly conserved amino-acid sequence in thrombospondin, properdin and in proteins from sporozoites and blood stages of a human malaria parasite" Nature, Sep. 1988, vol. 335, pp. 79-82.

Rodriguez, F. et al. "Immunodominance in Virus-Induced CD8 T-Cell Responses Is Dramatically Modified by DNA Immunization and Is Regulated by Gamma Interferon" Journal of Virology, May 2002, vol. 76, No. 9p. 4251-4259.

Roestenberg, M. et al. "Protection against a Malaria Challenge by Sporozoite Inoculation" New England Journal of Medicine, 2009, vol. 361, pp. 468-477.

Ruckwardt, T. et al. "Responses against a Subdominant CD8+ T Cell Epitope Protect against Immunopathology Caused by a Dominant Epitope" Journal of Immunology, 2010, vol. 185, pp. 4673-4680.

Sanchez, G. et al. "Plasmodium falciparum: Exported Protein-1, a Blood Stage Antigen, is Expressed in Liver Stage Parasites" Experimental Parasitology, 1994, vol. 79, pp. 59-62.

Schmidt, N. et al. "Extreme CD8 T Cell Requirements for Anti-Malarial Liver-Stage Immunity following Immunization with Radiation Attenuated Sporozoites" PloS Pathogens, Jul. 2010, vol. 6, No. 7, 15 pages.

Schmidt, N. et al. "Memory CD8 T cell responses exceeding a large but definable threshold provide long-term immunity to malaria" PNAS, Sep. 2008, vol. 105, No. 37, pp. 14017-14022.

Schwartz, J. et al. "Accurate gene synthesis with tag-directed retrieval of sequence-verified DNA molecules" Nature Methods, Sep. 2012, vol. 9, No. 9, pp. 913-915 with two supplemental pages.

Sedegah, M. "Sterile Immunity to Malaria after DNA Prime/Adenovirus Boost Immunization Is Associated with Effector Memory CD8+T Cells Targeting AMA1 Class I Epitopes" PLoS One, Sep. 2014, vol. 9, No. 9, 19 pages.

Sedegah, M. et al. "Effect on antibody and T-cell responses of mixing five GMP-produced DNA plasmids and administration with plasmid expressing GM-CSF" Genes and Immunity (2004) vol. 5, pp. 553-561.

Sedegah, M. et al. "Protection against malaria by immunization with plasmid DNA encoding circumsporozoite protein" Proc. Natl. Acad. Sci. USA, Oct. 1994, vol. 91, pp. 9866-9870.

Seder, R. et al. "Protection against Malaria by Intravenous Immunization with a Nonreplicating Sporozoite Vaccine" Science, Sep. 2013, vol. 341, pp. 1359-1365.

Seidlein, L. et al. "Malaria vaccines: past, present and future" Arch Dis Child 2013;98:981-985.

Spring, M. et al. "First-in-human evaluation of genetically attenuated Plasmodium falciparum sporozoites administered by bite of Anopheles mosquitoes to adult volunteers" Vaccine, 2013, vol. 31, pp. 4975-4983.

Stoute, J. et al. "A Preliminary Evaluation of a Recombinant Circumsporozoite Protein Vaccine against Plasmodium Falciparum Malaria" New England Journal of Medicine, Jan. 1997, pp. 86-91.

Trofa, A. et al. "Dengue Fever in US Military Personnel in Haiti" JAMA, May 1997, vol. 277, No. 19, pp. 1546-1548.

Tsuda, Y. et al. "A cytomegalovirus-based vaccine provides long-lasting protection against lethal Ebola virus challenge after a single dose" Vaccine, 2015, vol. 33, pp. 2261-2266.

Van Der Most, R. et al. "Analysis of Cytotoxic T Cell Responses to Dominant and Subdominant Epitopes During Acute and Chronic Lymphocytic Choriomeningitis Virus Infection" J Immunol 1996; 157, pp. 5543-5554.

Van der Most, R. et al. "Identification of Db- and Kb-Restricted Subdominant Cytotoxic T-Cell Responses in Lymphocytic Choriomeningitis Virus-Infected Mice" Virology, 1998, vol. 240, pp. 158-167.

Vaughan, A. et al. "Type II fatty acid synthesis is essential only for malaria parasite late liver stage development" Cellular Microbiology (2009) 11(3), 506-520.

Wang, R. "Simultaneous Induction of Multiple Antigen-Specific Cytotoxic T Lymphocytes in Nonhuman Primates by Immunization with a Mixture of Four Plasmodium falciparum DNA Plasmids" Infection and Immunity, Sep. 1998, pp. 4193-4202.

Wang, R. et al. "Boosting of DNA Vaccine-Elicited Gamma Interferon Responses in Humans by Exposure to Malaria Parasites" Infection and Immunity, May 2005, vol. 73, No. 5, pp. 2863-2872.

Wang, R. et al. "Induction of Antigen-Specific Cytotoxic T Lymphocytes in Humans by a Malaria DNA Vaccine" Science, Oct. 1998, vol. 282, pp. 476-480.

Warfield, K. et al. "Development and Characterization of a Mouse Model for Marburg Hemorrhagic Fever" Journal of Virology, Jul. 2009, pp. 6404-6415.

Weiss, W. et al. "Cytotoxic T Cells recognize a peptide from the circumsporozoite protein on malartia-infected hepatocytes" Journal of Experimental Medicine, Mar. 1990, vol. 171, pp. 763-773.

(56) References Cited

OTHER PUBLICATIONS

Weiss, W. et al. "Protective CE8+ T lymphocytes in Primates Immunized with Malaria Sporozoites" PLoS One, Feb. 2012, 4 pages.

WHO, "Global Malaria Programme: World Malaria Report 2014" 2014, 142 pages.

Wick, D. et al. "Profound CD8+ T cell immunity elicited by sequential daily immunization with exogenous antigen plus the TLR3 agonist poly(I:C)" Vaccine, 2011, vol. 29, pp. 984-993.

Williams, J. "Improving DNA Vaccine Performance Through Vector Design" Current Gene Therapy, Aug. 2014, vol. 14, No. 3, 21 pages.

Yager, E. et al. "Particle-mediated DNA vaccines against seasonal and pandemic influenza viruses elicit strong mucosal antibody and T cell responses in the lung" Procedia in Vaccinology 3 (2010) 2-11.

Zhang, Y. et al. "Seamless Ligation Cloning Extract (SLiCE) Cloning Method" Methods Mol Biol. 2014 ; 1116: 235-244.

Zhu, J. et al. "Structure of Plasmodium falciparum liver stage antigen-1" Molecular and Biochemical Parasitology, 1991, vol. 48, pp. 223-226.

USPTO, "International Search Report and Written Opinion", for PCT/US16/45439, 8 pgs, dated Oct. 18, 2016.

Barry, M. et al. "Expression library immunization to discover and improve vaccine antigens" Immunological Reviews, 2004, vol. 199, pp. 68-83.

Cao, Y. et al. "Gene Gun Bombardment with DNA-Coated Golden Particles Enhanced the Protective Effect of a DNA Vaccine Based on Thioredoxin Glutathione Reductase of Schistosoma japonicum" Biomed Research International, 2012 vol. 13, Article ID 952416, 10 pages.

Fan, Y. et al. "B7-DC-silenced dendritic cells induce stronger anti-HBV immunity in transgenic mice" Archives of Virology, 2009, vol. 154, pp. 1813-1821.

Hondowicz, B. et al. "Discovery of T Cell Antigens by High-Throughput Screening of Synthetic Minigene Libraries" PLoS One, 2012, 7(1). 10 pages.

Liu J, et al. "Enhancing Virus-Specific Immunity In Vivo by Combining Therapeutic Vaccination and PD-L1 Blockade in Chronic Hepadnaviral Infection" PLoS Pathogens, 2014 10(1): 14 pages.

Steitz, J. et al. "Biolistic DNA vaccination against melanoma" Biolistic DNA Delivery, Springer; 2013. p. 317-337.

\* cited by examiner

FIG. 2
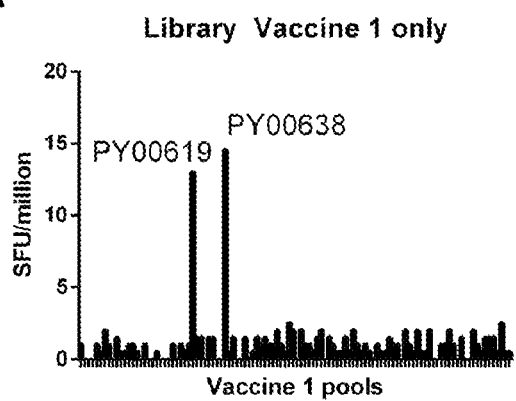
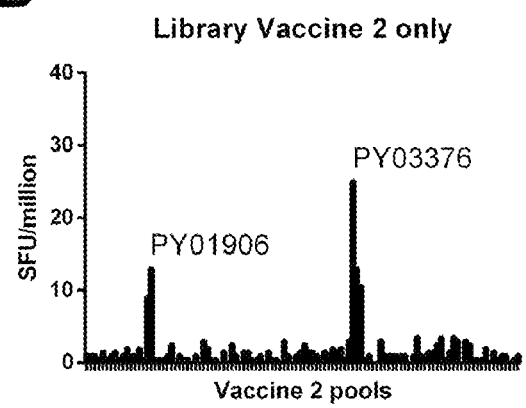
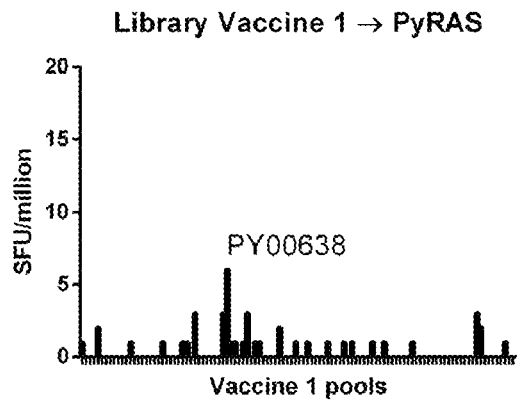
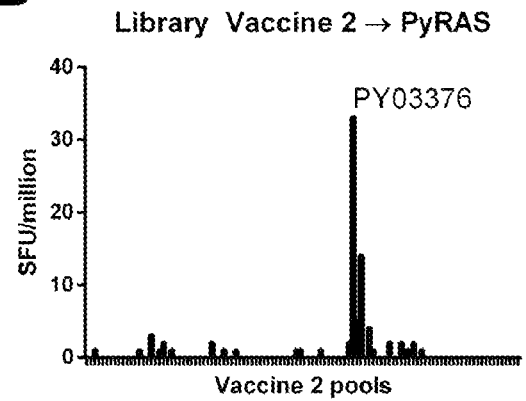
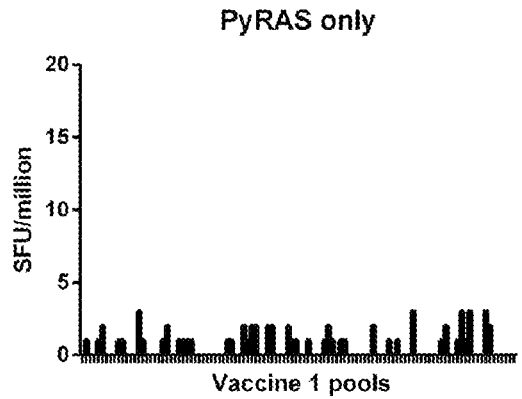

FIG. 11

| Vaccination regimen | | Day 6 ELISPOT | |
|---|---|---|---|
| Prime → | Boost (Day 0) | CSP | L3 |
| Naive | | | |
| DNA libraries | | | |
| Py | | | |
| Py | Py | | |
| Stage(s) expressed | | Spz/LS | LS |
| Epitope defined? | | Yes | Yes |

FIG. 16

| Vaccine | Gene ID | Product / Protein |
|---|---|---|
| 1 | PY00088 | hypothetical protein |
| 1 | PY00204 | hypothetical protein |
| 1 | PY00278 | 93 kDa protein |
| 1 | PY00286 | hypothetical protein |
| 1 | PY00293 | Papain family cysteine protease, putative |
| 1 | PY00444 | hypothetical protein |
| 1 | PY00454 | MAC/Perforin domain, putative |
| 1 | PY00455 | hypothetical protein |
| 1 | PY00565 | ClpB protein |
| 1 | PY00582 | heat shock protein 90-131 |
| 1 | PY00586 | hypothetical protein |
| 1 | PY00619** | hypothetical protein |
| 1 | PY00622 | rhoptry associated protein 1-31 |
| 1 | PY00638** | protein disulfide isomerase |
| 1 | PY00688 | Ribosomal protein L15 amino terminal region, putative |
| 1 | PY00775 | cytochrome c oxidase subunits 1-17 |
| 1 | PY00781 | peptidyl-prolyl cis-trans isomerase, cyclophilin-type |
| 1 | PY00802 | methionine aminopeptidase-like protein-related |
| 1 | PY00855 | Arabidopsis thaliana At3g05350/T12H1_32-52 |
| 1 | PY00891 | tRNA nucleotidyltransferase, mitochondrial precursor |
| 1 | PY00915 | Ser/Thr protein phosphatase, putative |
| 1 | PY00927 | prolyl-tRNA synthetase-related |
| 1 | PY01013 | hypothetical protein |
| 1 | PY01020 | Drosophila melanogaster CG15040 gene product |
| 1 | PY01024 | CCAAT-box DNA binding protein subunit B |
| 1 | PY01071 | multidomain scavenger receptor protein PbSR precursor |
| 1 | PY01204 | glutathione reductase |
| 1 | PY01244 | hypothetical protein |
| 1 | PY01448 | hypothetical protein |
| 1 | PY01475 | hypothetical protein |
| 1 | PY01557 | m1-family aminopeptidase |
| 1 | PY01589 | hypothetical protein |
| 1 | PY01622 | putative membrane glycoprotein yil173w precursor |
| 1 | PY01695 | acetyl-CoA carboxylase 1 precursor-related |
| 1 | PY01717 | hypothetical protein |
| 1 | PY01731 | hypothetical protein |
| 1 | PY01695 | acetyl-CoA carboxylase 1 precursor-related |
| 1 | PY01557 | m1-family aminopeptidase |
| 1 | PY01448 | hypothetical protein |
| 1 | PY01071 | multidomain scavenger receptor protein PbSR precursor |
| 1 | PY00927 | prolyl-tRNA synthetase-related |
| 1 | PY00891 | tRNA nucleotidyltransferase, mitochondrial precursor |
| 1 | PY00781 | peptidyl-prolyl cis-trans isomerase, cyclophilin-type |
| 2 | PY01750 | 60S ribosomal protein L27 homolog |
| 2 | PY01796 | hypothetical protein |
| 2 | PY01812 | phosphate translocator |
| 2 | PY01863 | hypothetical protein |
| 2 | PY01879 | Uba1 gene product-related |
| 2 | PY01906** | heat shock protein(s) 83-135 |
| 2 | PY01929 | hypothetical protein |
| 2 | PY01930 | hypothetical protein |
| 2 | PY01938 | PDZ domain protein |
| 2 | PY01972 | hypothetical protein |
| 2 | PY02090 | hypothetical protein |

FIG. 16 cont.

| Vaccine | Gene ID | Product / Protein |
|---|---|---|
| 2 | PY02148 | merozoite surface protein 7 precursor |
| 2 | PY02159 | Drosophila melanogaster CG15040 gene product |
| 2 | PY02266 | GTP-binding protein |
| 2 | PY02405 | hypothetical protein |
| 2 | PY02416 | 3-oxoacyl-acyl-carrier protein reductase precursor |
| 2 | PY02510 | PfSec61-78 |
| 2 | PY02587 | hypothetical protein |
| 2 | PY02884 | O1-O25 |
| 2 | PY02892 | hypothetical protein |
| 2 | PY02932 | PyRhopH1A-related |
| 2 | PY02935 | hypothetical protein |
| 2 | PY03047 | hypothetical protein |
| 2 | PY03081 | alanyl-tRNA synthetase, putative |
| 2 | PY03168 | circumsporozoite protein |
| 2 | PY03207 | 19-27 kDa sporozoite antigen, putative |
| 2 | PY03215 | hypothetical protein |
| 2 | PY03220 | hypothetical protein |
| 2 | PY03236 | DNA replication licensing factor mcm7-mcm40 |
| 2 | PY03372 | hypothetical protein |
| 2 | PY03376** | malate dehydrogenase |
| 2 | PY03421 | Arabidopsis thaliana P42268 |
| 2 | PY03426 | Elongation factor Tu family, putative |
| 2 | PY03544 | DnaJ homolog, putative |
| 2 | PY03549 | hypothetical protein |
| 2 | PY03582 | hypothetical protein |
| 2 | PY03622 | hribosomal protein S6, putative |
| 2 | PY03715 | hypothetical protein |
| 2 | PY03733 | hypothetical protein |
| 2 | PY03846 | enoyl-acyl carrier reductase |
| 2 | PY03885 | l-lactate dehydrogenase |
| 2 | PY03918 | RAP2, putative |
| 2 | PY04029 | hypothetical protein |
| 2 | PY04062 | Ribosomal protein S19e, putative |
| 2 | PY04147 | hypothetical protein |
| 2 | PY04254 | tyrosyl-tRNA synthetase 1-related |
| 2 | PY04273 | hypothetical protein |
| 2 | PY04408 | hypothetical protein |
| 2 | PY04421 | U43539 hepatocyte erythrocyte protein 17 kDa |
| 2 | PY04445 | malaria antigen-related |
| 2 | PY04452 | 3-oxoacyl-acyl-carrier protein synthase I/II |
| 2 | PY04489 | Sm protein, putative |
| 2 | PY04495 | 1st euk. member |

IMMUNOGENIC COMPOSITIONS, ANTIGEN SCREENING METHODS, AND METHODS OF GENERATING IMMUNE RESPONSES

CROSS-REFERENCE TO RELATED APPLICATION(S)

This application claims priority to U.S. Provisional Application No. 62/200,487, filed Aug. 3, 2015, the subject matter of which is hereby incorporated by reference in its entirety as if fully set forth herein.

STATEMENT REGARDING FEDERALLY SPONSORED RESEARCH

This invention was made with government support under Grant No. K08 AI097238-05, awarded by the National Institutes of Health. The government has certain rights in the invention.

BACKGROUND

Vaccines are one of the most effective interventions for combatting infectious diseases. However, economics has mainly led to the development of vaccines for only the most common viral and bacterial pathogens such as hepatitis A/B and polio viruses. There is a lack of useful vaccines for most human pathogens particularly those that are extremely complex and/or highly biohazardous. To address the unmet need for vaccines, new and more economically viable technologies are needed.

As an example, the recent Ebola virus (EBOV) outbreak in West Africa highlights the importance of developing vaccines against these types of emerging and re-emerging pathogens. To further illustrate the deficiencies in conventional vaccine strategies, the list of pre-erythrocytic T cell antigens suitable for use as malaria vaccine subunits has not grown appreciably in recent decades. This lack of progress is due in part to a fundamental flaw in the conventional approach to antigen identification. In the conventional approach, T cells from animals or humans repeatedly exposed to sporozoites are screened for responses against small numbers of pre-erythrocytic *Plasmodium* proteins. However, the antigens recognized by multiply-exposed responders do not include responses against two important classes of target antigens. Screening multiply-exposed animals fails to detect responses to subdominant antigens, as well as responses against dominant antigens that are expressed in the liver stage but not in sporozoites (Murphy et al. 2013). Both classes of antigens are likely to be rich sources of protective vaccine subunits (Ruckwardt et al. 2010; Im et al. 2011; Van Der Most et al. 1998; Van Der Most et al. 1996; Friedrich et al. 2007), but are undetectable in screens of sporozoite-hyperimmunized responders. In addition, the conventional approach is also limited by technological bottlenecks that limit the efficient study of T cell responses against the >1,000 *Plasmodium* proteins expressed the pre-erythrocytic stages. Collectively, these issues have dramatically curtailed the progress of malaria T cell vaccine research.

Conventional vaccine studies routinely assess responses against much smaller groups of manually cloned, non-codon optimized "candidate antigens", relying on guesswork and luck that a significant target is included in their analysis. Further, conventional approaches frequently use hyperimmunization with whole organisms as the paradigm for antigen discovery. This prevailing paradigm of sporozoite hyperimmunization leads to boosted responses against sporozoite-expressed antigens but fails to recall responses against antigens newly expressed in hepatocytes, even though primary sporozoite exposure primes such responses. Moreover, this conventional approach fails to identify subdominant antigens.

Shortcomings of the conventional approach to pathogen subunit identification must be addressed to generate effective multi-antigen subunit vaccines for numerous infectious diseases and other conditions that the conventional approach has failed to produce.

SUMMARY

An immunogenic composition is provided herein. The immunogenic compositions are used to identify and select immunogenic antigens that elicit immune responses in a subject and may be subsequently used in multi-antigen vaccine compositions against one or more diseases or conditions. According to some embodiments, the immunogenic composition may include a plurality of nucleic acid fragments or minigenes derived from a nucleic acid library, wherein each of the plurality of nucleic acid fragments encode a different antigen or functional portion thereof, and wherein the different antigens or functional portions thereof are associated with one or more disease or condition. The immunogenic composition may also include a delivery medium loaded with the plurality of nucleic acid fragments.

In other embodiments, the immunogenic composition may include one or more plasmid pools loaded into a dosing container. In such embodiments, each plasmid pool comprises a plurality of plasmids loaded onto a delivery medium, and wherein each of the plurality of plasmids comprise a nucleic acid fragment encoding a different antigen or functional portion thereof.

In some embodiments, the immunogenic compositions described herein may be used in a method for inducing an immune response in a subject or a population of cells. Such methods include a step of administering the immunogenic composition to the subject or population of cells. In certain aspects, administration may be accomplished using a gene gun.

In other embodiments, the immunogenic compositions described herein may be used in a method of screening candidate antigens or epitopes associated with a disease or condition. In such embodiments, the method may include steps of exposing one or more subjects or population of cells to the immunogenic composition, analyzing one or more biological samples obtained from the one or more subjects or population of cells using an assay to measure the response to the immunogenic composition, and identifying a nucleic acid fragment that is part of the immunogenic composition as encoding a candidate antigen or epitope when the nucleic acid fragment elicits a response measured by the assay in the one or more biological samples.

BRIEF DESCRIPTION OF THE DRAWINGS

FIG. 2 illustrates INFγ ELISPOT responses to sets of antigens within two different vaccine compositions. IFNγ responses in mice immunized with minigene library vaccines alone (FIGS. 2A-2B), library vaccines followed by sporozoites (FIGS. 2C-2D) or sporozoites alone (FIGS. 2E-2F) identify novel responses. ELISPOT results for Vaccine 1 (FIGS. 2A, 2C, 2E) and Vaccine 2 (FIGS. 2B, 2D, 2F), as indicated. Responses to Library vaccination alone are shown in FIGS. 2A-2B), responses to Library vaccine plus Sporozoites are shown in FIGS. 2C-2D. and responses to Sporozoites only are shown in FIGS. 2E-2F. Minigene pools are indicated along the x-axis (Vaccine 1=103 pools; Vaccine 2=105 pools) with the y-axis indicating average spots/well (SFU/million splenocytes). Targets were generated by transfecting PCR-amplified expression cassettes from each vaccine pool into $1\times10^6$ P815 cells using the RAW 264.7 program of an AMAXA 96-well shuttle. Transfected target cells from an individual transfection well were mixed with $10^6$ splenocytes (responding cell population) and ELISPOT plates were incubated overnight. ConA was included as a positive control and mock transfected P815's were used as negative controls. Plates were developed according to the manufacturers' instructions and scanned and analyzed using an ImmunoSPOT counter.

FIG. 11 depicts several vaccination strategies for the discovery and vaccination of sub-dominant antigens according to some embodiments.

DETAILED DESCRIPTION

Figure 1:
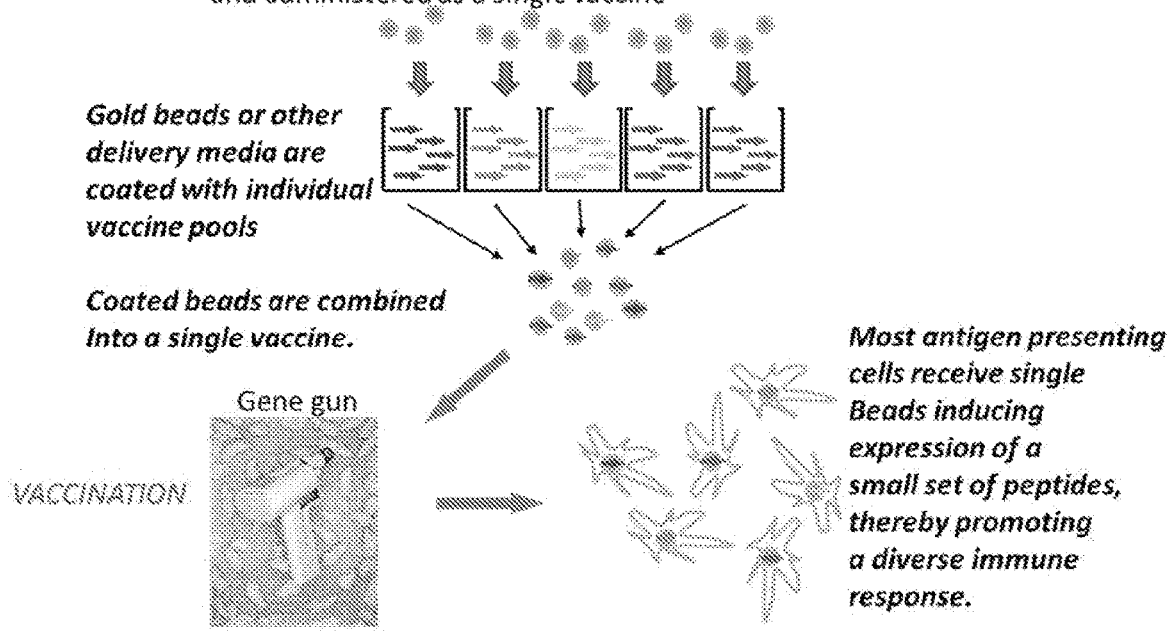
FIG. 1 depicts a model of one embodiment described herein. This FIG. depicts simultaneous delivery of multiple, small, low-complexity packets of antigens each to individual antigen presenting cells (APCs) during a single immunization. In this embodiment, while a whole vaccine composition may be large and complex, delivery of small sets of antigens or potential antigens allows each to be expressed, processed and presented to the immune system in the absence of competition from other antigens, either within or at the surface of antigen presenting cells. This provides responding immune cells access to each antigen within the vaccine composition.

Disclosed herein are various immunogenic compositions, methods for screening antigens, and methods for generating an immune response against multiple antigens.

The embodiments described herein are directed to an antigen discovery and vaccination/immunization platform sometimes referred to herein as "Highly parallel immunization" (HPI) or "minigene immunization/screening system" or "minigene vaccination system." HPI involves the use of immunogenic compositions or vaccines (i.e., "HPI compositions") that are derived from large, ordered libraries of plasmid clones that collectively encode the antigenic entirety of not only a single protein, but from sets of hundreds to thousands of proteins. These immunogenic compositions are used to identify and select immunogenic antigens that elicit immune responses in a subject and may be subsequently used in multi-antigen vaccine compositions against one or more diseases or conditions.

Development of antibody-based subunit vaccines has been aided by the inherent stability, sensitivity and soluble nature of antibodies in serum. In contrast, the development of T cell-based vaccines requires evaluation of live cellular MHC-restricted interactions between T cells and MHC-matched APCs displaying the cognate target antigen. For intracellular pathogens expressing thousands of potential targets, this requirement has inhibited discovery of protective vaccine subunits. The synthetic minigene vaccine platform technology (i.e., HPI platform) described herein is designed to enable the rapid evaluation of T-cell responses against large numbers of pathogen-derived proteins in order to identify both dominant and sub-dominant antigens.

Although the methods described herein regarding HPI platform can be applied to any antigen, protein, peptide, or pathogen, HPI was initially developed based on work directed to malaria vaccines. In that work, it was found that whole sporozoite vaccines initially induce many responses against abundant, immunodominant though non-protective (or 'chaff') proteins (Murphy et al. 2013). Many immunodominant responses are likely to be the result of cross-presentation of abundant epitopes from dead or dying parasites. Given that these responses are not protective, this type of "chaff" epitope is not likely to be under selective pressure to alter its primary structure to avoid immune detection. In contrast, epitopes that are processed and presented by a pathogen-infected somatic cell at a stage that is sensitive to T-cell mediated protection may be under significant selective pressure to evolve into less "immunodominant" forms. Dominant antigens have proven non-protective in bacterial and viral pathogens as well. Thus, in the malaria model, HPI can be used to search for protective liver-stage antigens (the 'wheat') whose potential importance has long been obscured by 'natural' immunizations with whole organisms.

The wheat vs. chaff dilemma described above is not specific to malaria, and in fact plagues all of vaccinology. For example, most antigen discovery platforms are applied following exposure to live whole pathogens and therefore rely on an immunogen (the whole organism) whose antigen stoichiometry and evolutionary history are likely to first reveal its most dispensable and largely non-protective antigens (the chaff). As described in detail in the working examples below, HPI can be used to overcome these past inadequacies by efficiently vaccinating naïve animals with highly complex vaccines where each subunit is delivered to distinct antigen presenting cells (APCs), thereby maintaining antigenic diversity and leveling the antigenic "playing field" prior to infection. HPI is therefore broadly applicable to many complex pathogens.

The HPI platform in accordance with the embodiments and working examples described herein provide advantages over conventional approaches in numerous and significant ways. For example, the embodiments disclosed herein are directed to antigen screening and vaccine development that uses minigene technology and comprehensive, high-throughput, ordered methods for both inducing and evaluating T cell responses against hundreds to thousands of pathogen-encoded proteins. In contrast, most conventional approaches for vaccine development assess natural exposure using peptide libraries or a limited library of manually-cloned, non-codon optimized candidate genes.

Additionally, the embodiments described herein that are directed to screening methods are pathogen and antigen unbiased. In other words, all antigens have an opportunity to be presented, which is not true for conventional whole organism approaches. Consequently, the methods described herein can be applied to any pathogen or to multiple pathogens at once. This is possible because T cells respond to linear peptide fragments. The methods described herein also maximize physical segregation at the level of antigen presentation, allowing for capture of dominant and subdominant responses. Sub-dominant immune responses can often provide protective effects that are not achieved when only the immunodominant responses are present. Thus, certain embodiments may be used to separate immunogenic antigens from the protective antigens which may be useful for subsequent vaccine development or reformulation.

Moreover, the methods described herein allow for screening and analysis of antigens by examining T cell immunogenicity of complete viral proteomes in biosafety level 1 (BSL1) conditions. The delivery components of the immunogenic compositions are non-pathogenic and are loaded with short amino acid-coding nucleotide sequences with non-viral sequences at both termini—thus it is not possible to re-assemble a full-length pathogens from these materials. Such embodiments allow most pre-clinical work to be done under BSL1 conditions. This aspect reduces costs and increases the number of facilities that can use the platform described by the embodiments described herein.

With these advantages in mind, the methods and compositions that are encompassed by the HPI platform are described below.

Immunogenic Compositions

According to the embodiments described herein, an immunogenic composition is provided that may be used in methods for inducing an immune response, methods for screening candidate antigens or epitopes associated with a disease or condition, or any other suitable methods.

In some embodiments, the immunogenic composition includes a plurality of nucleic acid fragments or "minigenes", each of which encodes an antigen, protein or peptide or a portion thereof. As discussed herein, a portion of an antigen may be any portion of an antigen that is encoded by a portion of the coding domain of an antigen, and in certain embodiments, may be a functional portion of an antigen. A functional portion of an antigen may be any portion of an antigen that is recognized by a subject's cellular or humoral immune system, e.g., by T lymphocytes, B lymphocytes, or antibodies. Functional portions of an antigen may elicit an immune response or reaction by the subject's immune system. Examples of functional portions of antigens include, but are not limited to, antigenic determinants or epitopes (including conformational epitopes or linear epitopes).

In accordance with the embodiments described herein, immunogenic compositions provided for use in the HPI platform include a plurality of nucleic acid fragments that are derived a nucleic acid library that encodes a plurality of antigens or functional portions thereof. This nucleic acid library may also be referred to as an antigen library. The nucleic acid library is designed by selecting a plurality of target proteins that are associated with a pathogen, protein or other molecule that causes or is involved with one or more diseases or conditions. The proteins may represent a selected portion or the entirety of a pathogen's proteome, or may be selected from published or experimental expression data, proteomics data, or other suitable selection criteria for target proteins involved with the diseases or conditions. Sets of minigenes may optionally be selected based on a complex, ordered antigen source such as a cDNA-derived or synthetic DNA expression library encoding a large number of pathogen or tumor-derived proteins, or a peptide or protein library.

Any number of target proteins may be selected. Once the target proteins are selected, the coding domains of the genes encoding the target proteins are fragmented into a set of nucleic acid fragments—or minigenes. In some aspects, the nucleic acid fragments are designed to have overlapping codons on each end, and in certain aspects, the minigene fragments are codon optimized. In one embodiment, each minigene fragment is appended with a suitable promoter sequence (e.g., T7 promoter, CMV promoter) and a start codon at the 5' end; and with suitable primer sequences on each end to allow for amplification of the minigenes. In some embodiments, the nucleic acid fragments loaded onto a delivery medium have a tag. In some embodiments, the tag is a ubiquitin tag.

In certain embodiments, the minigenes are amplified and subjected to an error correction strategy to ensure the minigenes do not have errors. In some embodiments a "dial-out" error correction strategy is used (Schwartz & Shendure 2012).

The immunogenic composition can include any number of nucleic acid fragments (or minigenes). In certain embodiments, the immunogenic composition includes a plurality of nucleic acid fragments, wherein each of the plurality of nucleic acid fragments encode a different antigen or functional fragment thereof. In such embodiments, the immunogenic composition may include 2 or more nucleic acid fragments which encode 2 or more antigens or functional fragments thereof; 3 or more nucleic acid fragments which encode 3 or more antigens or functional fragments thereof; 4 or more nucleic acid fragments which encode 4 or more antigens or functional fragments thereof; 5 or more nucleic acid fragments which encode 5 or more antigens or functional fragments thereof; 6 or more nucleic acid fragments which encode 6 or more antigens or functional fragments thereof; 7 or more nucleic acid fragments which encode 7 or more antigens or functional fragments thereof; 8 or more nucleic acid fragments which encode 8 or more antigens or functional fragments thereof; 9 or more nucleic acid fragments which encode 9 or more antigens or functional fragments thereof; 10 or more nucleic acid fragments which encode 10 or more antigens or functional fragments thereof; 11 or more nucleic acid fragments which encode 11 or more antigens or functional fragments thereof; 12 or more nucleic acid fragments which encode 12 or more antigens or functional fragments thereof; 13 or more nucleic acid fragments which encode 13 or more antigens or functional fragments thereof; 14 or more nucleic acid fragments which encode 14 or more antigens or functional fragments thereof; 15 or more nucleic acid fragments which encode 15 or more antigens or functional fragments thereof; 16 or more nucleic acid fragments which encode 16 or more antigens or functional fragments thereof; 17 or more nucleic acid fragments which encode 17 or more antigens or functional fragments thereof; 18 or more nucleic acid fragments which encode 18 or more antigens or functional fragments thereof; 19 or more nucleic acid fragments which encode 19 or more antigens or functional fragments thereof; 20 or more nucleic acid fragments which encode 20 or more antigens or functional fragments thereof; 25 or more nucleic acid fragments which encode 25 or more antigens or functional fragments thereof; 30 or more nucleic acid fragments which encode 30 or more antigens or functional fragments thereof; 35 or more nucleic acid fragments which encode 35 or more antigens or functional fragments thereof; 40 or more nucleic acid fragments which encode 40 or more antigens or functional fragments thereof; 45 or more nucleic acid fragments which encode 45 or more antigens or functional fragments thereof; 50 or more nucleic acid fragments which encode 50 or more antigens or functional fragments thereof; 55 or more nucleic acid fragments which encode 55 or more antigens or functional fragments thereof; 60 or more nucleic acid fragments which encode 60 or more antigens or functional fragments thereof; 65 or more nucleic acid fragments which encode 65 or more antigens or functional fragments thereof; 70 or more nucleic acid fragments which encode 70 or more antigens or functional fragments thereof; 75 or more nucleic acid fragments which encode 75 or more antigens or functional fragments thereof; 80 or more nucleic acid fragments which encode 80 or more antigens or functional fragments thereof; 85 or more nucleic acid fragments which encode 85 or more antigens or functional fragments thereof; 90 or more nucleic acid fragments which encode 90 or more antigens or functional fragments thereof; 95 or more nucleic acid fragments which encode 95 or more antigens or functional fragments thereof; 100 or more nucleic acid fragments which encode 100 or more antigens or functional fragments thereof; 200 or more nucleic acid fragments which encode 200 or more antigens or functional fragments thereof; 300 or more nucleic acid fragments which encode 300 or more antigens or functional fragments thereof; 400 or more nucleic acid fragments which encode 400 or more antigens or functional fragments thereof; 500 or more nucleic acid fragments which encode 500 or more antigens or functional fragments thereof; 600 or more nucleic acid fragments which encode 600 or more antigens or functional fragments thereof; 700 or more nucleic acid fragments which encode 700 or more antigens or functional fragments thereof; 800 or more nucleic acid fragments which encode 800 or more antigens or functional fragments thereof; 900 or more nucleic acid fragments which encode 900 or more antigens or functional fragments thereof; or 1000 or more nucleic acid fragments which encode 1000 or more antigens or functional fragments thereof.

In certain embodiments, the plurality of nucleic acid fragments are incorporated into a vector for production and delivery. In certain aspects, the plurality of nucleic acid fragments are incorporated into a plasmid to generate a plasmid pool. The plasmid pool includes plasmids which express each of the nucleic acid fragments in the immunogenic composition.

In some embodiments, the nucleic acid fragments (or minigenes) are grouped into one or more pools. And, in accordance with certain embodiments, the immunogenic composition is comprised of nucleic acid fragments from each of the one or more pools. In certain aspects, the immunogenic composition is generated from combining an aliquot of each of the one or more pools into a single composition. The immunogenic compositions therefore may include one or more pools, wherein each pool includes 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, or more than 20 different minigenes. In one example, the nucleic acid fragments are grouped into pools of 10 different minigenes. In these embodiments, each minigene is appended with a pool-specific primer sequence (unique to the minigenes of each pool) and a common primer sequence in addition to the promoter sequence and start codon.

Each minigene in a pool may be incorporated into a suitable vector—such as a plasmid—for production and delivery. Thus, the one or more pools of the immunogenic compositions may comprise one or more plasmid pool in accordance with certain embodiments. In these embodiments, each plasmid pool may include 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, or more than 20 different minigenes, each of which is incorporated into a plasmid.

For immunogenic compositions that are designed from a combination of one or more pools or plasmid pools, the immunogenic composition may include minigenes or plasmids (which comprise a minigene) from 1, 2, 3, 4, 5, 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 50 or more, 60 or more, 70 or more, 80 or more, 90 or more, 100 or more, 200 or more 300 or more, 400 or more, 500 or more, 600 or more, 700 or more, 800 or more, 900 or more, or 1000 or more plasmid pools. In this manner, the immunogenic compositions may include between 2 to over 5000 minigenes. For example, the immunogenic compositions may be comprised of an aliquot from each of 100 pools or plasmid pools, where each plasmid pool includes 10 different minigenes, resulting in an immunogenic composition that includes 1000 different minigenes. As further explained herein, the minigenes may target one or more different antigens, proteins or functional portions thereof (e.g., epitopes).

In certain embodiments, the nucleic acid fragments that make up the immunogenic composition are selected from codons within the coding domain of a single protein or antigen. In these embodiments, the nucleic acid fragments or minigenes that make up the immunogenic compositions described herein encode antigens or functional portions thereof that are part of a single protein. Proteins may have several antigenic sites (or epitopes) that may elicit an immune response by the subject's cellular immune system (i.e., B and T lymphocytes). As such, the immunogenic compositions may be designed to include multiple antigenic sites (or epitopes) to generate a more effective or a more robust immune response against that protein. Alternatively, the immunogenic compositions may be designed to include multiple antigenic sites by including nucleic acid fragments that encompass an entire protein gene in order to determine and screen for antigenic sites for that protein.

In other embodiments, the nucleic acid fragments or minigenes that make up the immunogenic compositions described herein encode antigens or functional portions thereof that are part of different proteins. As described herein, the HPI platform can be used to generate compositions that include minigenes that span the entirety of a plurality—up to 1000 or more—of proteins.

In some embodiments, the nucleic acid fragments that make up the immunogenic composition are selected from codons within the coding domain of a portion of single antigen or protein or from codons within the coding domain of the entirety of one or more antigens or proteins. In some embodiments, the nucleic acid fragments that make up the immunogenic composition are selected from codons within the coding domain of a portion or the entirety of a plurality of target proteins or antigens. In some embodiments, the nucleic acid fragments that make up the immunogenic composition are selected from partially overlapping regions within the coding domain of an antigen such that at least a portion of the individual minigenes within the set partially overlap with other nucleic acid fragments within the same set. Antigenic sites that are identified using the immunogenic compositions described herein may then be assessed for any protective effect for use in an immunogenic composition.

According to some embodiments, the nucleic acid fragments or minigenes that are part of the immunogenic compositions are loaded onto a suitable delivery media. Thus, according to the embodiments described herein, the immunogenic composition also includes a delivery medium that is loaded with the nucleic acid fragments or the plasmids comprising the nucleic acid fragments. The delivery medium may be of any suitable media for gene or microgene delivery of nucleic acid fragments or plasmids to target cells (e.g., antigen presenting cells). Non-limiting examples of suitable delivery media may include, but is not limited to, viral vectors, (e.g., retroviral vectors, leniviral vectors, adeno-associated viral vectors, adenoviral vectors), lipid cations, liposomes, chitosan, modified cyclodextrins, PLGA, nanobubbles, cell penetration enhancer peptides, nanoparticles (e.g., albumin-bound nanoparticles, polymeric nanoparticles, dendrimers, iron oxide nanoparticles, quantum dots, silver nanoparticles, and gold nanoparticles), gold particles or beads, microneedles and dissolving microneedles. In one embodiment, the delivery medium is gold particles or gold beads. In certain embodiments, a hybrid particle may be used as the delivery medium, for example, chitosan coated onto small gold beads.

According to some embodiments disclosed herein, sets of minigenes from a single protein are individually loaded onto the delivery media resulting in distinct, low-complexity pools of antigens or portions of antigens that are delivered to different antigen presenting cells (APCs) thereby avoiding "antigenic" or "immune" competition among antigens within the composition. This approach is known to diversify immune responses compared to immunization with a complex but completely mixed DNA sample (see Yager et al. 2010; Liu et al. 2006; Rodriguez et al. 2002). Moreover, immune recognition in the absence of competition promotes immune responses against a diverse set of antigens.

In certain embodiments, the nucleic acid fragments (or minigenes) are independently loaded onto individual media. In certain aspects of these embodiments, the delivery medium may be loaded with individual nucleic acid fragments (or minigenes), a single pool, or plasmid pool (e.g., the pools and plasmid pools described above); or may be loaded with a subpool of any individual pool or plasmid pool (e.g., a pool or plasmid pool may be subdivided into different subpools of related minigenes within one pool or plasmid pool). In certain embodiments, an individual aliquot of each pool, plasmid pool, or subpool thereof is loaded onto individual aliquots of the delivery media in a parallel manner. This process may be referred to as massive parallel loading of the delivery media. When loaded in this manner, the immunogenic or vaccine composition minimizes antigenic competition in individual antigen presenting cells (APC) upon administration of the immunogenic or vaccine composition. Further, the delivery medium is loaded with nucleic acid fragments in this manner, individual antigen presenting cells receive only a subset of the nucleic acids within a vaccine in order to minimize antigenic competition.

To this end, certain embodiments of the immunogenic or vaccine compositions are generated as follows. In one embodiment, an individual aliquot of the delivery medium (e.g., gold particles or beads) is loaded with a plurality of nucleic acid fragments that are part of a single pool or a plasmid pool (e.g., the pools or plasmid pools described above and in the working examples), the result of which generates a pool of loaded delivery media (e.g., a pool of loaded gold particles). This pool of loaded delivery media represents a distinct subset of antigens or functional portions thereof to minimize antigenic competition in individual antigen presenting cells as discussed herein. In certain embodiments, to minimize antigenic competition, each distinct subset of antigens or functional portions thereof are derived from or related to a single protein or antigen. The pool of loaded delivery media may be combined with one or more additional pools of loaded delivery media to generate a vaccine composition—each pool generated as described above. As described herein, the immunogenic compositions may be used as vaccines—and the one or more pools of loaded delivery media may comprise a vaccine composition for delivery of the plurality of nucleic acid fragments (or minigenes).

In other embodiments, an immunogenic composition includes one or more pools or plasmid pools (e.g., the pools or plasmid pools described above. In such embodiments, an aliquot of each of the one or more pools or plasmid pools is loaded onto an individual aliquot of a delivery medium (e.g., gold particles or beads) to generate a vaccine composition comprising one or more pools of loaded delivery media (e.g., loaded gold particles). Each of the one or more pools of loaded delivery media encode a distinct subset of antigens or functional fragments thereof. As a non-limiting example, one pool of loaded delivery media may include a pool or plasmid pool that comprises nucleic acid fragments that encode one protein, or a portion of a protein, but the vaccine composition may include pools of loaded delivery media that comprise nucleic acid fragments that encode hundred to thousands of proteins, as discussed in detail above.

In certain embodiments, the vaccine and immunogenic compositions described above may be delivered via a Particle Mediated Epidermal Delivery (PMED or "gene gun") by "shooting" the compositions (generally loaded into a cassette) across the dermis or skin. When delivered to a subject, loaded delivery media (e.g. loaded gold particles or beads) enter antigen presenting cells (APC)—each APC receiving one loaded particle or bead. Thus, each APC only expresses a small subset of the antigens encoded by the entire vaccine composition. This minimizes competition and promotes a more diverse immune response.

In some embodiments, the delivery medium is gold particles. In one embodiment, each species of plasmid encoding a single protein, antigen, or functional portion thereof, is formulated onto or loaded onto individual aliquots of gold beads. In some aspects of this embodiment, collections of gold beads representing 10 to 50 different proteins may then be generated as described above, combined and delivered in a single shot by PMED. Separating the plasmid DNA in this manner allows each transfected APC to process and present peptides from a single foreign antigen, thereby circumventing antigenic "cross-competition" within and at the surface of an APC. This maximizes the diversity of T cell or antibody responses in the host. Other complex DNA vaccine technologies (e.g. Expression Library Immunization or "ELI") do not define or normalize the DNA constituents within a vaccine or deliver antigens individually to distinct APCs.

When delivered to a subject in accordance with the methods described herein, the plurality of nucleic acid fragments are expressed as antigens or functional portions thereof and presented on the surface of the subject's antigen presenting cells (APCs). One or more of the antigens or functional portions thereof encoded by the nucleic acid fragments may ultimately elicit an immune response or reaction in response to these nucleic acid fragments. In certain embodiments, the immunogenic compositions elicit a beneficial immune response, and can be used in methods for inducing an immune response described below. In certain aspects, the immune reaction may be protective against a disease or condition. In these aspects, antigens or portions of antigens may elicit immune responses similar to those elicited in subjects having various diseases or conditions. These diseases or conditions may include, for example, infectious diseases, malignancies, autoimmune diseases, bacterial infections, fungal infections, viral infections, or transplants.

In some embodiments, the immunogenic composition may be part of a vaccine composition. In certain embodiments a vaccine composition comprises at least one active ingredient. In one embodiment, an active ingredient of the vaccine composition may comprise an immunogenic composition described in the embodiments above. A vaccine composition is intended to elicit an immune response when administered to a subject or population of cells. In some aspects, the vaccine composition, when administered to a subject or a population of cells, promotes or enhances acquired humoral immunity, cellular immunity, or both as described herein. Thus, in some aspects, the recombinant adenovirus as described herein is useful as a vaccine to promote or enhance humoral immunity, cellular immunity, or both.

In further embodiments, the vaccine composition may enhance infection-preventing effects against infectious antigens. Thus, the vaccine composition may be a prophylactic or protective vaccine against one or more diseases or conditions associated with or caused by a foreign pathogen, protein or peptide, or by a host protein or peptide. Alternatively the vaccine composition may be used as a therapeutic vaccine to elicit an immune response against a current infection, disease or condition. A vaccine composition may also be used as an investigative tool in antigen discovery. Vaccine compositions used in antigen discovery methods elicit putative immune responses when administered to a subject or to a population of cells. Thus, the vaccine or immunogenic compositions contemplated herein may be protective or non-protective.

A vaccine composition as described herein may comprise a therapeutically effective amount of an immunogenic composition described herein, and further comprising a pharmaceutically acceptable carrier according to a standard method. Examples of acceptable carriers include physiologically acceptable solutions, such as sterile saline and sterile buffered saline.

In some embodiments, the immunogenic or vaccine composition may be used in combination with a an adjuvant to enhance the immune response elicited by the immunogenic composition. Any immunologic or immunomodulatory adjuvant that may stimulate the immune system and increase the response to a vaccine, without having any specific antigenic effect itself may be used as the adjuvant. Many immunologic adjuvants mimic evolutionarily conserved molecules known as pathogen-associated molecular patterns (PAMPs) and are recognized by a set of immune receptors known as Toll-like Receptors (TLRs). Examples of adjuvants that may be used in accordance with the embodiments described herein include Freund's complete adjuvant, Freund's incomplete adjuvant, double stranded RNA (a TLR3 ligand), LPS, LPS analogs such as monophosphoryl lipid A (MPL) (a TLR4 ligand), flagellin (a TLR5 ligand), lipoproteins, lipopeptides, single stranded RNA, single stranded DNA, imidazoquinolin analogs (TLR7 and TLR8 ligands), CpG DNA (a TLR9 ligand), Ribi's adjuvant (monophosphoryl-lipid A/trehalose dicorynoycolate), glycolipids (α-GalCer analogs), unmethylated CpG islands, oil emulsion, liposomes, virosomes, saponins (active fractions of saponin such as QS21), muramyl dipeptide, alum, aluminum hydroxide, squalene, BCG, cytokines such as GM-CSF and IL-12, chemokines such as MIP 1-α and RANTES, N-acetylmuramine-L-alanyl-D-isoglutamine (MDP), thymosin αl and MF59. The amount of adjuvant used can be suitably selected according to the degree of symptoms, such as softening of the skin, pain, erythema, fever, headache, and muscular pain, which might be expressed as part of the immune response in humans or animals after the administration of this type of vaccine. In some embodiments, the amount of adjuvant used may be a pharmaceutically effective amount.

Other adjuvants that may be used in combination with the immunogenic or vaccine compositions include, but are not limited to, one or more molecules that provide for non-systemic blockade of one or more immunomodulatory molecules including, but not limited to, RNAi molecules (e.g., siRNA, shRNA, or the like), genetic adjuvants, or DNA encoding *Escherichia coli* heat-liable enterotoxin LT. For example, the adjuvant molecule may be one of these molecules that provides for non-systemic blockade against programmed death-ligand 1 (PDL-1), programmed death-ligand 2 (PDL-2), a toll-like receptor (TLR), TLR1, TLR2, TLR3, TLR4, TLR5, TLR6, TLR7, TLR8, TLR9, TLR19, TLR11, TLR12, TLR13, B7 family members (e.g., B7-H3, B7-H4 and the like), ligands to TLR and B7 family members, salts, gels, aluminum salts, aluminum gels, monophosphoryl lipid A, bacterial adjuvants, or other suitable adjuvants. In certain embodiments, the immunogenic or vaccine composition includes an inhibitor against PDL-1, PDL-2, or both. In some aspects of this embodiments, the inhibitor is an RNAi molecule, and in one aspect the RNAi molecule is an shRNA.

According to certain embodiments, an adjuvant may be considered to be used in combination with the immunogenic or vaccine compositions described herein if the adjuvant is co-administered with the immunogenic or vaccine compositions in any suitable non-systemic manner. For example, the adjuvant may be mixed with or otherwise made part of the immunogenic or vaccine compositions itself and is therefore administered in the same manner as the composition. In another example, the adjuvant may be administered separately from, but at approximately the same time as the immunogenic or vaccine compositions.

In further embodiments, use of various other adjuvants, drugs or additives with the immunogenic or vaccine compositions of the invention, as discussed above, may enhance the therapeutic effect achieved by the administration of the vaccine or immunogenic composition. The pharmaceutically acceptable carrier may contain a trace amount of additives, such as substances that enhance the isotonicity and chemical stability. Such additives should be non-toxic to a human or other mammalian subject in the dosage and concentration used, and examples thereof include buffers such as phosphoric acid, citric acid, succinic acid, acetic acid, and other organic acids, and salts thereof; antioxidants such as ascorbic acid; low molecular weight (e.g., less than about 10 residues) polypeptides (e.g., polyarginine and tripeptide) proteins (e.g., serum albumin, gelatin, and immunoglobulin); amino acids (e.g., glycine, glutamic acid, aspartic acid, and arginine); monosaccharides, disaccharides, and other carbohydrates (e.g., cellulose and derivatives thereof, glucose, mannose, and dextrin), chelating agents (e.g., EDTA); sugar alcohols (e.g., mannitol and sorbitol); counterions (e.g., sodium); nonionic surfactants (e.g., polysorbate and poloxamer); and PEG.

The immunogenic or vaccine compositions described herein may be loaded into and/or stored as an aqueous solution or a lyophilized product in a dosing container such as a biolistic cartridge, a sealed ampoule or a vial.

According to some embodiments disclosed herein, the compositions described herein may be used in methods for inducing or eliciting an immune response in a subject or a population of cells. In certain embodiments, the compositions may be used in methods that provide protective immunization to a subject. The compositions may also be used in methods for identifying both dominant and subdominant antigens for a disease or condition. For example, this approach has been used to identify both dominant and subdominant malaria T cell antigens from among 100 candidate targets (see the working examples below).

In other embodiments, a plurality of nucleic acid fragments (or minigenes) that encode different antigens that are determined to be effective in protecting a subject from an epidemic, endemic, hyperendemic, or pandemic disease or condition may be used to form an immunogenic composition or vaccine.

In other embodiments, the immunogenic composition may include a plurality of nucleic acid fragments that encode antigenic portions of proteins associated with a single disease or condition. Complex pathogens may have multiple proteins that contribute to infection of host cells and diseases or conditions associated with that infection. Further, those proteins may have multiple antigens or antigenic determinants that can be targeted to enhance an immune response against that pathogen. In addition, conditions such as autoimmune diseases or conditions related to or caused by transplantation may be caused by several different proteins.

Epidemic, pandemic, and endemic diseases: Avian influenza, Cholera, Coronaviruses (e.g., MERS-CoV, SARS), Emerging diseases (e.g. nodding disease), Ebola, Hendra virus infection, Hepatitis B, HIV, Influenza (seasonal, pandemic), Leptospirosis, Malaria, Meningitis, Nipah virus infection, Plague, Rift Valley fever, Smallpox and human monkeypox, Tularaemia, Viral haemorrhagic fevers (e.g., Ebola, Marburg, Lassa, Crimean-Congo haemorrhagic fever, etc.), Yellow fever, Zika virus. It is noted, however, that epidemic, pandemic, and endemic diseases are an evolving group of diseases, thus the aforementioned diseases only represent examples and additional diseases may become epidemic, pandemic, or endemic at a later date. In accordance with this embodiment, one or more immunogenic compositions may be formulated to protect a subject or a population of subjects from one or more of the aforementioned diseases. Using the HPI methods described herein, these compositions may be tailored to deliver a multi-antigenic vaccine to deliver a robust response to these diseases. Thus, in such embodiments, the immunogenic composition comprises a plurality of nucleic acid fragments or minigenes that encode antigens that are associated with one or more of the aforementioned diseases or conditions.

Target Diseases and Conditions

The list of FDA-approved vaccines for use in humans is short (www.fda.gov/BiologicsBloodVaccines/Vaccines/ApprovedProducts/UCM093833). Safe, effective vaccines are still needed for most human pathogens including the pathogens targeted by the immunogenic compositions described herein.

Because the compositions, vaccines and methods described herein are broadly applicable and can be used to develop immunogenic compositions relating to any pathogen, protein or peptide, the embodiments described herein may be used in antigen discovery and vaccination of subjects for any disease or condition. Exemplar diseases and conditions that may be targeted include endemic, epidemic and pandemic diseases, diseases that may be used as weapons, diseases that affect livestock, and diseases that affect travelers.

Non-limiting examples of diseases and conditions that may be targeted using the immunogenic compositions described herein are as follows.

Malaria. In a non-limiting example, the embodiments described herein may be used in antigen discovery and vaccination of subjects for malaria. *Plasmodium* parasites cause malaria, a mosquito-borne disease responsible for hundreds of thousands of deaths and hundreds of millions of clinical cases annually (WHO Global Malaria Programme, 2014). After transmission from feeding Anopheline mosquitoes, injected sporozoite-stage parasites travel through the skin and eventually make their way to the liver where they initiate an asymptomatic hepatocyte infection that culminates days later in release of erythrocyte-stage merozoites. The merozoites initiate a cyclical infection of erythrocytes that leads to the clinical manifestations of malaria, including fevers and chills and sometimes progressing to severe anemia, coma and death. Researchers have long been investigating ways to produce a safe and effective vaccine that induces complete protection against infection with *Plasmodium* sporozoites, but to no avail. To achieve this goal, a major focus has been placed on vaccines targeting the pre-erythrocytic stages of development (the transmitted sporozoite stage and the subsequent liver stage) (Hoffman et al. 2015a). Experimental vaccination of humans and mice with attenuated sporozoites protects against challenge with wild-type sporozoites (Nussenzweig et al. 1967; Clyde et al. 1973; Mueller et al. 2005; Putrianti et al. 2009; Roestenberg et al. 2009; Seder et al. 2013). Antibodies can block hepatocyte invasion (Keitany et al. 2014), while CD8+ cytotoxic T cells recognize parasite-infected hepatocytes Doolan & Hoffman 2000; Kumar et al. 1988; Weiss et al. 1990) and can provide sterile protection in several mouse models (Van Braeckel-Budimir & Harty 2014). Furthermore, CD8+ T cells play a role in protection in primates (Weiss & Jiang 2012) and likely in humans as well (Sedegah et al. 2014) and are induced in humans experimentally immunized with attenuated sporozoites (Epstein et al. 2011; Spring et al. 2013). Parasite-specific CD8+ T cells may kill infected cells by one or more proposed mechanisms (reviewed in Freyert & Krzych]). Thus, inclusion of CD8+ T cell target antigens is likely to be critical for any sterile protective malaria vaccine.

There are two basic approaches to pre-erythrocytic malaria vaccine development—manufacture of an attenuated 'whole organism' vaccine or identification and manufacture of a single subunit antigen or set of antigens that can provide complete protection (Hoffman et al. 2015b; von Seidlein & Bejon 2013). However, the extremely large number of genes expressed by *Plasmodium* has thus far prevented the efficient identification of broadly protective antigens suitable either for inclusion within a subunit vaccine or for targeting by transgenic parasite vaccines with improved protective efficacy.

For subunit vaccines, there are two sequential phases of development: antigen discovery and formulation testing. Antigen discovery typically involves screening of immune cells from pathogen-exposed subjects for responses against small numbers of laboriously cloned, pathogen-derived gene products or predicted peptide epitopes. Antigen discovery is then followed by an equally laborious process of production and evaluation of experimental vaccines targeting the newly discovered antigenic proteins-many vaccines fail here because the antigens discovered simply do not induce protective responses. As the number of proteins increases, each step requires considerable investment of time and money, with no guarantee that the antigens discovered will ultimately confer protection when formulated as a vaccine.

*Plasmodium* species each encode ~5,300 proteins but only a few pre-erythrocytic *Plasmodium* proteins (i.e., CSP, TRAP, LSA1, Exp1/Hep17, CelTOS, L3, Pf16, STARP) have been studied as T cell antigens (Khusmith et al. 1991; Robson et al. 1988; Sanchez et al. 1994; Moelans et al. 1991; Fidock et al. 1994; Murphy et al. 2013; Doolan et al. 1996; Guerin-Machand et al. 1987; Zhu & Hollingdale 1991; Kariu et al. 2006; Bergmann-Leitner et al. 2010). Amongst those tested in humans (CSP, LSA-1, Exp-1, TRAP, CelTOS), most have not reliably induced complete protection (reviewed in Duffy et al. 2012), Because it is nearly impossible to systematically study all potential T cell antigens using conventional methods, a number of higher throughput approaches have been applied to malaria T cell antigen discovery. Synthetic *Plasmodium* peptides (Reyes-Sandoval et al. 2009; Doolan et al. 2003; Mishra et al. 2011; Aguiar et al. 2015) or antigen presenting cells (APCs) transfected with *Plasmodium* protein-expressing plasmids (Wang et al. 2005a) have all been used to screen for T cell interferon-γ (IFNγ) responses in vitro,_but such approaches are limited by the cost of large peptide libraries and the complexity of cloning A/T-rich Plasmodial genes, respectively. Recently, a peptide screening approach identified multiple new antigens targeted by T cell responses from RAS-immunized humans (Aguiar et al. 2015)—protection afforded by these antigens is not yet known. APCs transfected with minigene libraries encoding long *Plasmodium* peptides have been utilized in an effort to capture a larger portion of the proteome using synthetic biology techniques (Murphy et al. 2013).

New methods that accelerate discovery of vaccine subunits for pathogens with thousands of genes would be a major step forward in the fight against *Plasmodium* and other complex intracellular pathogens. DNA vaccination and screening is ideally suited for such higher-complexity evaluation of vaccine candidates.

In accordance with the working examples below, an immunogenic or vaccine composition is provided against malaria. In the embodiment described in Example 1 below, minigenes comprising nucleic acid fragments that encode a portion a pathogen, protein or peptide are used to both initiate specific immune responses in vivo as a DNA-based vaccine, and to subsequently screen DNA vaccine-induced T cell responses to identify antigenic targets. This approach combines the antigenic complexity achieved by whole organism vaccines with the feasibility of multi-subunit vaccination. A microarray-based oligonucleotide synthesis technology was used to rapidly produce two complex minigene vaccines, each encoding over 1,000 peptides derived from 36 (vaccine 1) and 53 (vaccine 2) liver-stage *P. yoelii* proteins (FIG. 16). Targets were a set of pre-erythrocytic proteins containing signal peptides and/or transmembrane domains. Putatively secreted or transmembrane proteins were selected based on their potential to cross both the parasite membrane and the parasitophorous vacuolar membrane to enter the hepatocyte MHC class I pathway. The assumption that such parasite proteins may be exported into the hepatocyte is based on the observation that exported erythrocyte-stage PEXEL/HT domain-containing proteins also contain a signal peptide or a transmembrane domain (Hiller et al. 2004; Marti et al. 2004).

Following vaccine production, mice were repeatedly gene gun vaccinated with the minigene libraries followed, in some mice, by sporozoite exposures. T cell IFNγ responses were evaluated and several novel responses were identified including a strong response to *P. yoelii* malate dehydrogenase (PyMDH), which was further characterized and found to bear similarities to another recently described *Plasmodium* liver-stage T cell response.

The preliminary study to evaluate this embodiment indicates that T cell responses against genuine *Plasmodium* antigens can be induced and detected using highly complex DNA minigene vaccines. As described in the working examples, additional improvements designed to increase the breadth and magnitude of responses, coupled with improved screening sensitivity may allow minigene vaccination/screening technology to be used for high-throughput identification of protective T cell antigens.

Ebola and hemorrhagic fever viruses. On Sep. 2, 2014, Médecins Sans Frontières (MSF) requested civilian and military aid to assist with the crisis and approximately 2,500 U.S. troops were deployed to assist. As of September 2015, the EBOV Zaire outbreak in West Africa caused thousands of deaths in Guinea (2,530), Sierra Leone (3,953) and Liberia (4,808) (www.cdc.gov/vhf/ebola/outbreaks/2014-west-africa/case-counts.html; accessed Sep. 9, 2015). U.S. military personnel were required to perform twice-daily temperature and symptom monitoring of all personnel throughout deployment and conducted exit screening and 21 days of post-deployment monitoring in segregated areas on U.S. military installations. This intensive approach prevented any known cases in U.S. personnel (Cardile et al. 2015) but at considerable cost. Recent studies demonstrate promising data on EBOV vaccine development, but there are multiple EBOV strains and EBOVs represent just one of several geographically-related filoviruses that can cause hemorrhagic fevers. Other hemorrhagic fever viruses include LASV and MARV—neither has an approved vaccine available. The multi-virus HPI approach described herein has the potential to illuminate the response profiles to these viruses and to potentially develop a multi-virus vaccination platform to prevent such infections.

Dengue. DENV outbreaks have occurred in militaries worldwide (Kunwar & Prakash 2015) including during multiple U.S. deployments. DENV accounted for at least 20% of hospitalizations in the U.S. Somalia deployment (Gibbons et al. 2012) and was responsible for >30% of febrile illness in hospitalized U.S. troops deployed to Haiti in 1994 (Gibbons et al. 2012; From the CDC 1994; Trofa et al. 1997). More recently, 500 samples from US Army Special Forces collected during 2006-2008 showed an 11% seroprevalence for DENV antibodies (Gibbons et al. 2012). Vaccines that induce non-neutralizing antibodies may put recipients at risk of antibody-dependent enhancement of infection with a different DENV serotype. Without an effective vaccine, DENV will remain a significant risk in many destabilized tropical and subtropical regions and pose a threat to the U.S. military.

Other viruses. Viruses such as Venezuelan equine encephalitis (VEE), Western equine encephalitis (WEE), Eastern equine encephalitis (EEE), Chikungunya (CHIKV), Crimean-Congo hemorrhagic fever (CCHF), Japanese encephalitis virus (JEV), enterovirus 71 (EV71) and West Nile Virus (WNV), also pose ongoing military and civilian threats. Notably WNV and CHIKV virus transmission is occurring in the domestic U.S. following introduction from abroad. Some of these viruses such as the alphaviruses have demonstrated immune interference following co-administration of formalin-inactivated EEE and WEE in humans (Reisler et al. 2012), making approaches like HPI more desirable since it aims to reduce interference.

*Coxiella burnetii*. *Coxiella burnetii* is an obligate intracellular gram-negative bacterium and the agent of Q fever in humans. *C. burnetii* has a broad host range including small ruminants (sheep/goats), representing an efficient, inexpensive and easily concealed host for propagation. *C. burnetii* is recognized as a Category B bioterrorism agent because of its ability to disseminate through the air, persist in the environment, and induce disease following inhalation of a single organism. Outside of the host cell, the bacterium is extremely resilient in a spore-like form able to resist ultraviolet radiation, heat, desiccation, pressure and osmotic and oxidative stress, making it more easily weaponizable. Infected sheep and goats shed large numbers of *C. burnetii* in birth products, and this material is easy to obtain and transport. Human infection may be asymptomatic or can lead to acute or chronic Q fever, a debilitating, influenza-like illness that may be accompanied by pneumonia, endocarditis, abortion, premature birth or even death. Disease can be especially severe when diagnosis is delayed and when persons with cardiac diseases or immunocompromised states are infected. As a potential bioweapon, *Coxiella* could be engineered to express novel virulence factors and/or to deliver potent novel toxins, leading to devastating outcomes. Unfortunately, despite agricultural, medical and biodefense importance, there are no vaccines available in the U.S. for humans or livestock. A T-cell subunit vaccine for *C. burnetii* may be developed using the HPI platform approach to functionally test the 1,000 most likely vaccine target antigens in *C. burnetii* murine models. A refined multi-antigen subunit vaccine could be used to vaccinate military personnel, animal workers and even livestock.

*Theileria parva.* East Coast fever, a devastating disease of cattle, sheep and goats, is caused by *Theileria parva.* The HPI platform described herein may be used to develop viable vaccines against *T. parva* as described in the working examples below.

Methods of Antigen Screening

According to some embodiments disclosed herein, the immunogenic and/or vaccine compositions described above methods may be used in screening methods for antigen discovery. Such methods include a step of exposing one or more subjects or populations of cells to any immunogenic composition or a vaccine composition described above. In certain embodiments, the subject or population of cells is exposed to between 5 and 100 pools of nucleic acid fragments or plasmids, but may be exposed to hundreds to thousands of proteins and the minigenes encoding said proteins in accordance to the description and working examples described herein.

The subject or population of cells may be exposed to the immunogenic or vaccine compositions by any suitable delivery or administration method including, but not limited to, biolistic particle bombardment (i.e., via gene gun delivery), electroporation, highly parallel electroporation, a transdermal patch, microneedles, or via highly parallel microneedles. Subjects may include humans, animals (such as mammals, birds, reptiles, fish, and amphibians), or any other subjects that may become infected with or suffers from the target diseases or conditions associated with the antigens or proteins that are included in the immunogenic compositions described herein.

After exposure to the immunogenic or vaccine composition, a suitable sample or biological sample (e.g., cell culture media or extract, blood, serum, cerebrospinal fluid, urine, saliva, etc.) is analyzed using an assay to measure the response to the immunogenic or vaccine composition. Any suitable assay may be used to analyze the response including, but not limited to, enzyme-linked immunospot assay (ELISPOT), lymphocyte proliferation assay (LPA), cytokine production (CP) assay, and intracellular cytokine production (ICC) assay. These assays may be used to generate readouts for any cytokine or other substance that indicates the activation or activity of an immune response. For example, these assays may assess levels of gamma interferon, granszyme B, tumor necrosis factor (TNF), antibodies produced from activated B cells, or any other suitable markers.

A nucleic acid fragment that is part of the immunogenic or vaccine composition is identified as encoding a candidate antigen or epitope that may be used in a targeted vaccine composition when the nucleic acid fragment (or minigene) elicits a response measured by the assay.

These methods can be used in a variety of ways to identify antigens and/or induce immune protection against specific pathogens or diseases. For example, according to one embodiment, the screening methods facilitate the discovery of novel subdominant antigens through the vaccination of naïve test animals followed by antigenic screening in the absence of exposure to pathogen.

In another embodiment, screening methods facilitate the discovery of novel pathogen-derived antigens that are recalled by exposure to the pathogen following vaccination of naïve test animals followed by exposure to the pathogen and antigenic screening (pathogenic "boosting" following vaccine "priming").

According to some embodiments, adjuvants may be co-administered with delivery components as an alternative to or in addition to including adjuvants in the immunogenic compositions or vaccine compositions described above. Embodiments described herein allow for the differential use of adjuvants, wherein adjuvants may be matched with appropriate antigens. For example, an adjuvant that promotes an antibody response can be co-loaded with B cell target antigens, while T cell target antigens can be co-loaded with adjuvants that promote a T cell response. Adjuvants that may be used in accordance with the embodiments described herein are described in detail above.

According to some embodiments, the methods for antigen screening described herein allow for the addition of new antigenic targets to an established vaccine, enabling a vaccine to be "updated" or "patched" as new antigens or new strains of pathogens evolve.

Additionally, according to embodiments described herein, methods of screening antigens may include ordered analysis of a plurality of antigens or pieces thereof and determining whether a particular minigene elicits an immune response in a subject. Further, according to embodiments described herein, vaccine compositions may be administered to a subject for a plurality of different conditions and antigens or pieces thereof simultaneously.

Additional embodiments related to the screening methods described herein are further described and included in the working examples below.

Methods for Eliciting an Immune Response Against Multiple Antigens

According to some embodiments, the immunogenic composition or vaccine compositions may be used in methods for inducing an immune response in a subject or in a population of cells. Such methods may include a step of administering an immunogenic or vaccine composition to the subject or population of cells, wherein the immunogenic or vaccine composition is a composition described above.

The subject or population of cells may be exposed to the immunogenic or vaccine compositions by any suitable delivery or administration method including, but not limited to, biolistic particle bombardment (i.e., via gene gun delivery), electroporation, highly parallel electroporation, a transdermal patch, microneedles, or via highly parallel microneedles. In certain embodiments, the immunogenic or vaccine compositions administered to the subject may be loaded into a biolistic cassette or a plurality of biolistic cassettes, each biolistic cassette.

Subjects may include humans, animals (such as mammals, birds, reptiles, fish, and amphibians), or any other subjects that may become infected with or suffers from the target diseases or conditions associated with the antigens or proteins that are included in the immunogenic compositions described herein.

In certain embodiments, the subject is administered with an immunogenic or vaccine composition that elicits a beneficial or protective immune response that could be useful in treating or preventing one or more conditions. In certain embodiments, a condition may be caused by, for example, an infectious pathogen, a malignancy, an autoimmune disease, a transplant, a disease, a human disease, a mammalian disease, a non-mammalian disease, a virus, bacteria, fungi, or a condition may be caused by a combination of the foregoing.

The vaccine composition administered to the subject in accordance with the embodiments described herein may be designed to prevent a single condition or a plurality of conditions.

In some embodiments, the immunogenic or vaccine compositions used in accordance with the methods for eliciting a protective immune response are designed to elicit an immune response to about 2 to about 20 antigens or pieces of antigens. In some embodiments, the vaccine composition is designed to elicit a protective immune response to about 20 to about 50 antigens or pieces of antigens. In some embodiments, the vaccine composition is designed to elicit a protective immune response to about 50 to about 100 antigens or pieces of antigens. In some embodiments, the vaccine composition is designed to elicit a protective immune response to about 100 to about 500 antigens or pieces of antigens. In some embodiments, the vaccine composition is designed to elicit a protective immune response to about 500 to about 1000 antigens or pieces of antigens. In some embodiments, the vaccine composition is designed to elicit a protective immune response to about 1000 to about 5000 antigens or pieces of antigens. In some embodiments, the vaccine composition is designed to elicit a protective immune response to about 5000 to about 10000 antigens or pieces of antigens. In some embodiments, the vaccine composition is designed to elicit a protective immune response to about 10000 to about 15000 antigens or pieces of antigens. In some embodiments, the vaccine composition is designed to elicit a protective immune response to about 15000 to about 20000 antigens or pieces of antigens. In some embodiments, the vaccine composition is designed to elicit a protective immune response to more than 20000 antigens or pieces of antigens. In some embodiments, the immunogenic or vaccine compositions elicit a non-protective but nonetheless beneficial immune response. For example, the immunogenic composition or vaccine composition may elicit a non-protective immune response that—when co-administered with an adjuvant or otherwise combined with another agent or method—produces an enhanced or synergistic effect against the pathogen or protein targeted by the composition.

According to some embodiments, the methods for antigen screening are combined with the methods for eliciting an immune response. For example, methods for antigen screening allow the discovery of new antigenic targets to an established vaccine that may enhance or improve existing vaccines. Thus, the methods for eliciting an immune response provided herein may include immunogenic or vaccine compositions that can be updated to include new antigens to new strains of pathogens or variants/mutants of proteins as they are identified by the screening methods.

According to some embodiments, vaccine compositions include adjuvants. Embodiments described herein enable the differential use of adjuvants, wherein adjuvants may be matched with appropriate antigens. For example, an adjuvant that promotes an antibody response can be co-loaded with B cell target antigens, while T cell target antigens can be co-loaded with adjuvants that promote a T cell response.

Adjuvants that may be used in combination with the immunogenic or vaccine compositions are described in detail above. For example, suitable adjuvants may include, but are not limited to, one or more molecules that provide for non-systemic blockade of one or more immunomodulatory molecules including, but not limited to, RNAi molecules (e.g., siRNA, shRNA, or the like), genetic adjuvants, or DNA encoding *Escherichia coli* heat-liable enterotoxin LT. For example, the adjuvant molecule may be one of these molecules that provides for non-systemic blockade against programmed death-ligand 1 (PDL-1), programmed death-ligand 2 (PDL-2), a toll-like receptor (TLR), TLR1, TLR2, TLR3, TLR4, TLR5, TLR6, TLR7, TLR8, TLR9, TLR19, TLR11, TLR12, TLR13, B7 family members (e.g., B7-H3, B7-H4 and the like), ligands to TLR and B7 family members, salts, gels, aluminum salts, aluminum gels, monophosphoryl lipid A, bacterial adjuvants, or other suitable adjuvants. In certain embodiments, the immunogenic or vaccine composition includes an inhibitor against PDL-1, PDL-2, or both. In some aspects of this embodiments, the inhibitor is an RNAi molecule, and in one aspect the RNAi molecule is an shRNA. The adjuvant may be part of the immunogenic composition as described above, or may be co-administered with the immunogenic composition.

In some embodiments, methods to prevent a condition or a plurality of conditions are provided wherein a vaccine composition is administered to a subject at a spaced interval. A spaced interval may be any interval deemed appropriate to maintain prevention of the condition, plurality of conditions, or a subset of the plurality of conditions that the method is designed to prevent.

Protection Against Specific Groups of Diseases and Conditions

In certain embodiments, the immunogenic compositions are comprised of the immunogenic or "vaccine" compositions described in the working examples below.

The compositions, vaccines and methods described herein may be directed to identifying protective antigens to one or more diseases or conditions, and to methods of protecting a subject from such diseases or conditions. As described herein, the HPI platform is well suited to antigen discovery and vaccine development related to any disease or condition, or any combination of diseases or conditions. In certain embodiments, the immunogenic compositions described herein include a plurality of nucleic acid fragments (or minigenes) that encode different antigens that are determined to be effective in protecting a targeted group of subjects from one or more diseases or conditions. In certain aspects, immunogenic compositions described herein include a plurality of nucleic acid fragments (or minigenes) that encode different antigens that are determined to be effective in protecting a targeted group of subjects from a selected group of diseases or conditions (i.e., two or more diseases or conditions). In such embodiments, the immunogenic composition may include a plurality of nucleic acid fragments that encode antigenic portions of proteins associated with one or more childhood diseases or conditions, one or more diseases that pose a threat to travelers, or one or more weaponizable diseases. Other examples include one or more diseases that pose a threat to elderly subjects, one or more diseases that pose a threat to pregnant subjects, one or more disease that pose a threat to livestock, or any other group of diseases that can affect a particular group of subjects.

As a non-limiting example, the plurality of nucleic acid fragments or minigenes that are part of a immunogenic composition may encode antigens that are associated with one or more diseases or conditions that pose a threat to travelers. Examples of diseases or conditions that pose a threat to travelers include, but are not limited to, African Tick-Bite Fever, African Trypanosomiasis (African Sleeping Sickness), Avian Flu (Bird Flu), Chagas Disease (American Trypanosomiasis), Chikungunya, Dengue, Diphtheria, Ebola, Flu (Influenza), HIV, Hand, Foot, and Mouth Disease, Hepatitis A, Hepatitis B, Hepatitis C, Hepatitis E, Japanese Encephalitis, Leptospirosis, Malaria, Measles, Meningococcal Disease (Neisseria meningitidis), Mumps, Murray Valley Encephalitis virus, Pertussis (Whooping Cough), Plague, Pneumococcal Disease (Streptococcus pneumoniae), Polio, Rabies, Rift Valley Fever, Ross River virus disease, Rubella, Scabies, Schistosomiasis, Tetanus, Tick-borne Encephalitis, Tuberculosis (TB), Typhoid Fever, West Nile virus, Yellow Fever, and Zika. In accordance with this embodiment, one or more immunogenic compositions may be formulated for travelers going to a particular region of the world where one or more of the aforementioned diseases may pose a threat. Using the HPI methods described herein, these compositions may be tailored to deliver all necessary immunizations to a subject prior to travelling to a particular region—in a single vaccine. Thus, in such embodiments, the immunogenic composition comprises a plurality of nucleic acid fragments or minigenes that encode antigens that are associated with one or more of the aforementioned diseases or conditions. In some embodiments, the immunogenic composition comprises a plurality of nucleic acid fragments or minigenes that encode antigens that are associated with two or more, three or more, four or more, five or more, six or more, seven or more, eight or more, nine or more, ten or more, more than ten, or of the aforementioned diseases or conditions.

In another non-limiting example, the plurality of nucleic acid fragments or minigenes that are part of a immunogenic composition may encode antigens that are associated with one or more childhood diseases or conditions that are part of recommended vaccination schedules for children. Examples of childhood diseases or conditions that are given to children in accordance with a recommended vaccination schedule include, but are not limited to, Chicken Pox, Diphtheria, Influenza, Hepatitis A, Hepatitis B, HIB, Human Papillomavirus (HPV), Measles, Meningococcal, Mumps, Polio, Pneumococcal, Rotavirus, Rubella, Tetanus, TDAP, and Pertussis (Whooping Cough). In accordance with this embodiment, one or more immunogenic compositions may be formulated for children to be used in a recommended vaccination schedule. Using the HPI methods described herein, these compositions may be tailored to deliver all necessary immunizations to a child at one time, or at each recommended age during the recommended schedule—in a single vaccine. Thus, in such embodiments, the immunogenic composition comprises a plurality of nucleic acid fragments or minigenes that encode antigens that are associated with one or more of the aforementioned childhood diseases or conditions.

In another non-limiting example, the plurality of nucleic acid fragments or minigenes that are part of a immunogenic composition may encode antigens that are associated with one or more weaponizable diseases or conditions that pose a threat to military or civilian subjects. Examples of weaponizable diseases or conditions that pose a threat to travelers include, but are not limited to, Ebola (EBOV), Marburg (MARV), Lassa (LASV), Venezuelan equine encephalitis (VEE), Western equine encephalitis (WEE), Eastern equine encephalitis (EEE), DENV types 1-4, Chikungunya (CHIKV), Crimean-Congo hemorrhagic fever (CCHF), Japanese encephalitis virus (JEV), enterovirus 71 (EV71) and West Nile virus (WNV).

The following examples are provided to better illustrate the embodiments and are not to be interpreted as limiting the scope of any claimed embodiment. The extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention. Further, all references cited herein are hereby incorporated by reference in their entirety as if fully set forth herein.

EXAMPLES

Example 1: Identification of Dominant and Subdominant T Cell Antigens

As discussed herein, an antigen discovery and immunization platform was developed address the shortcomings of the conventional approaches known in the art. This platform utilizes a high-throughput synthetic "minigene" pipeline to enable rapid and flexible synthetic DNA library vaccine production (~50 protein experimental vaccines) in a matter of weeks. In contrast to the conventional approach, vaccination of naïve animals with minigene libraries followed by a single exposure to sporozoites allows the efficient detection of dominant and sub-dominant responses, including liver-stage responses.

Methods

Vaccine Design. Eighty-nine liver stage *P. yoelii* 17XNL proteins predicted to contain a signal peptide and/or have transmembrane domains were selected using filters built into PlasmoDB. (www.plasmodb.orq; see PlasmoDB: a functional genomic database for malaria parasites. Nucleic Acids Res. 2008 Oct. 31. Aurrecoechea C, et al., which is incorporated by reference herein). Coding sequences were downloaded and broken into sequential 33 codon segments overlapping by 14 codons. All permutations of closely spaced variations were included as alternate minigenes. A pool specific primer unique to groups of 10 minigenes followed by a start codon were appended onto the 5' end of each segment, while a common primer sequence was appended onto the 3' end of each segment. The reverse compliment of each 150 base minigene template was ordered as a single oligo-pool synthesis from CustomArrays Inc. (Bothell, Wash.). Gene identifiers and product descriptions from PlasmoDB.org are listed in FIG. 16.

Vaccine Assembly. Each pool of 10 minigenes was amplified using individual pool-specific primers combined with the common primer. Pool specific primers included a T7 promoter sequence on the 5' end. Equivalent amounts of each pool were then combined and subjected to "dial-out" error correction strategy as described by Schwartz and Shendure (Schwartz & Shendure 2012). Briefly, random tags were added by amplifying the combined library using step-out primers hybridizing to the T7 and common primer sequences. The tagged library was sequenced using base paired-end reads on an Illumina miSeq by a commercial vendor. Reads were aligned with the original library design and dial-out primer pairs flanking accurate minigenes were selected. Dial out primer pairs for each minigene were ordered from IDT. Error-corrected minigenes were amplified using the selected dial-out primers. Each minigene was individually recombined as an amino-terminal fusion with the mouse LC3 coding sequence in a modified pNGVL3 vector using SLiCE ligation-independent cloning (Zhang et al. 2014). Recombined plasm ids were transformed into DH10G hosts by electroporation using an AMAXA 96-well shuttle and cultured individually in 1.2 mls of LB in deep-well 96-well plates. Groups of 10 cultures were pooled, centrifuged and frozen pending purification. Bacterial pellets were processed using a Qiagen 96-Plus Endotoxin-free kit according to the manufacturers' instructions. Typical yields were between 100 and 300 ng/ul for each pool.

Loading of Gene Gun Cartridges. Nine µl of each plasmid pool was combined with 1 ul of 200 ng LT adjuvant (Arrington et al. 2002) plasmid in a single well of a 96-well V-bottom assay plate. Each well was diluted with 10 ul 50 mM spermidine and 1 mg of 1 um gold beads (Inbios Gold). Plates were agitated on a horizontal shaker while 10 ul of 10% CaCl2 was added to each well. DNA coated gold particles were spun down and washed 3 X with 100% ethanol and gold particles were suspended in 10 µl of 100% ethanol with 50 ug/ml polyvinylpyrrolidone (PVP). One quarter of all pools in a vaccine (24 wells or the equivalent of ~12 40 kdal proteins) were combined and loaded into Tefzel gene gun cartridges using a homemade tube "turner". Gene gun cartridge tubes were dried, sliced and stored desiccated at 4° C.

Mice. All animal studies were approved by the University of Washington Institutional Animal Care and Use Committee (protocol 4317-01). BALB/cj mice were obtained from Jackson Laboratories (Bar Harbor, Me.) and housed in approved facilities at the University of Washington. Thy1.1+ BALB/c mice were bred at the University of Washington from a pair originally obtained from Jackson Laboratories. Humane sacrifice was performed by flow-metered carbon dioxide overdose.

Vaccinations. Female Balb/cj (~8 wk old) mice were shaved on their abdomen and administered the DNA vaccine corresponding to 0.5-1.0 µg total DNA using a PowderJect XR1 biolistic delivery device (Pertmer et al. 1995). On days 0, 21, and 49, each mouse received four separate cartridges, one cartridge corresponding to each quarter of a vaccine. At later time points, vaccinated mice were humanely sacrificed and splenocytes harvested and pooled for screening as described below.

Generation of screening templates. One µl of each vaccine pool was diluted 1:100 and further amplified using Rolling Circle amplification using a TempliPhi kit (GE BioSciences). RC amplified DNA from each minigene pool was used as a template to amplify short linear expression cassettes from the CMV promoter through the human beta-globin 3'UTR/polyA signal. PCR reactions utilized 20 ng template combined with a CMV promoter-specific primer and a 3' human beta-globin UTR antisense primer and Phusion polymerase. Cycling conditions were 35 cycles of 98 C (15 sec), 55 C (15 sec), and 72 C (2 min) each. Products were purified using 96-well filter plates (Qiagen, Valencia, Calif.) and resuspended in 20 µL 10 mM Tris (pH 7.8).

Library screening. Ready-Set-Go mouse IFNγ ELISPOT kits (eBioscience, San Diego, Calif.) were used to evaluate responses to vaccine encoded antigens. Briefly, 2 µL of PCR-amplified expression cassettes from each minigene pool in each vaccine were transfected into $1 \times 10^6$ freshly dividing P815 cells using the RAW 264.7 program of an AMAXA 96-well shuttle. Splenocytes ($1 \times 10^6$/well) were added to each ELISPOT well as responders and ELISPOT plates were incubated overnight. ConA was included as a positive control and mock transfected P815's were used as negative controls. Plates were developed according to the manufacturers' instructions and scanned and analyzed using an ImmunoSPOT counter (Cellular Technology Limited, Shaker Heights, Ohio). Transfection efficiency was also controlled by checking GFP expression and viability by flow cytometry of separate wells of P815 cells transfected on each plate of wells.

Sporozoite immunizations. Where indicated, BALB/cj mice were singly or doubly immunized with $1 \times 10^4$ wild-type P. yoelii sporozoites and were then administered azithromycin i.p. (0.8 mg/d) on Days 1-3 postimmunization. In other experiments, mice were immunized once or twice with combinations of PyRAS and/or genetically-attenuated Pyfabb/f- sporozoites (Vaughan et al. 2009) as described (Murphy et al. 2013). Sporozoites were obtained from the Center for Mosquito Production and Malaria Infection Research (CeMPMIR, Center for Infectious Disease Research, Seattle, Wash).

MHC binding assay. RMA/S cells expressing $H2\text{-}K^d$ were used to test MHC binding as described (Murphy et al. 2013; Mullbacher et al. 1999).

In vivo cellular cytotoxicity assay. The in vivo killing assay was performed to measure cellular cytotoxicity as previously reported [26] although three populations of target cells were differentially labeled here with Cell Proliferation Dye eFluorl®670 (eBioscience) at 5 µM (PyMDH), 0.75 µM (PyCSP) and 0.1 µM (mock).

Immunization-challenge experiments. To generate DNA and Listeria-based vaccines for single antigen immunization, minigene-encoded antigens were isolated and further cloned into the delivery vectors. Briefly, minigene expression constructs encoding the dominant PyCSP epitope SYVPSAEQI and the dominant PyMDH epitope SYQKSINNI were cloned separately into the pNGVL3.LC3 vector for use as DNA vaccines. Recombinant PyCSP-expressing actA-/in1γ- L. monocytogenes was a kind gift from Aduro Biotech. PyMDH-expressing actA- L. monocytogenes was constructed by cloning a minigene encoding the PyMDH epitope into the pPL2-N4 vector. The resulting pPL2-N4. MDH plasmid was transformed into SM10 hosts and conjugated into actA- Lm10403S. Using these materials, a gene gun DNA prime/recombinant Listeria boost protocol was used to vaccinate mice against single antigens prior to sporozoite challenge. For each arm of the experiment, mice were primed against either PyCSP or PyMDH using two gene gun cartridges on Days 0 and 2. Three weeks later, animals were boosted i.v. with $5 \times 10^6$ CFU recombinant Lm expressing the cognate antigen and treated with 2 mg/mL ampicillin in the drinking water for 3 days thereafter. Animals were challenged three weeks later with $1 \times 10^4$ wild-type P. yoelii sporozoites i.v. Forty-four hours later, animals were humanely sacrificed and livers perfused with PBS. Livers were harvested and emulsified in a bead beater with NucliSens lysis buffer (bioMérieux, Durham, N.C.) to preserve RNA. Total nucleic acid was extracted using a NucliSens EasyMag (bio-Mérieux) and Plasmodium 18S rRNA and murine GAPDH were measured by RT-PCR as described [26]. Liver burden is reported as log 10 changes between mice for Plasmodium 18S rRNA copy number normalized to mouse GAPDH. At the time of humane sacrifice, spleens were also harvested for ELISPOT analysis as a measure of T cell frequency at the time of challenge (no T cell expansion during 0-44 hours post-challenge).

Results

Synthetic biology methods enable rapid production of multi-protein synthetic minigene libraries suitable for T cell vaccination and subsequent screening. Two minigene libraries encoding peptides from 36 (Vaccine 1) or 53 (Vaccine 2) P. yoelii proteins each were synthesized (FIG. 16). Error-correction including Dial-out tagging, sequencing, analysis and re-amplification was completed in 4 weeks. The libraries were designed to contain the complete peptide compliment of all included proteins, but after error correction by dial-out PCR, a fraction of minigenes could not be recovered as error-free sequences. Vaccine 1 contained 91.9% of the intended proteome (95% CI: 87.4-96.4%) and Vaccine 2 contained 91.1% (95% CI: 87.0-95.3%). Plasmid insertion and plasmid culture/isolation were accomplished in three weeks. Spot-checking individual cultures by sequencing showed that >90% of clones encoded the intended sequence. The proteins included in the libraries are listed FIG. 16. Minigenes were adjuvanted with the LT-encoding plasmid (Arrington et al. 2002) and loaded onto individual aliquots of gold particles for biolistic delivery.

Response to vaccination. Library vaccination and minigene screening lead to identification of library vaccine-induced IFNγ-producing T cell responses. BALB/cj mice (n=5/group) were vaccinated with Vaccine 1 or Vaccine 2 on Days 0, 21 and 49 using a PowderJect research device (i.e., a gene gun). Aside from mild erythema at the gene gun vaccination site for 1-2 days post-vaccination, the mice tolerated the DNA vaccination without any obvious signs of distress. IFNγ responses were evaluated using pooled splenocytes harvested six days after the final gene gun vaccination. To evaluate the >100 minigene pools per vaccine, duplicate wells of target cells (P815) were each transfected with PCR-amplified expression cassettes corresponding to each minigene pool in a vaccine (10 minigenes/pool). The transfected target cells ($1\times10^6$/well) were combined with $1\times10^6$ splenocytes from library-vaccinated mice in overnight IFNγ ELISPOT assays as previously reported [26]. Compared to previous minigene-transfected ELISPOT screens of sporozoite-immunized mice [26], background production of IFNγ in these experiments on DNA minigene library-vaccinated mice was extremely low (<3 SFU/million splenocytes). Such low background signal is critical for detection of responses in the setting of multi-protein vaccination. Two antigens in each vaccine induced responses significantly above baseline (FIGS. 2A and 2B). Each of the antigenic pools contained minigenes from a single protein such that the initial screen identified responses to the products of genes PY00619 (a hypothetical protein) and PY00638 (protein disulfide isomerase) in Vaccine 1 and PY01906 (heat shock protein) and PY03376 (malate dehydrogenase) in Vaccine 2.

Recall response to Sporozoites. A subset of the minigene library vaccinated animals were administered $2\times10^4$ irradiated P. yoelii sporozoites (PyRAS) 16 days after the final gene gun vaccination and splenocytes were harvested 7 days after RAS exposure. Minigene-transfected P815 ELISPOT screening was again conducted to identify vaccine-primed, RAS-recalled responses. Recall responses were observed against pools encoding PY00619, PY00638 and PY03376 whereas responses against the PY01906 pool were undetectable (FIGS. 2C and 2D).

Vaccine antigens primed by exposure to Sporozoites. To determine if RAS alone could induce these responses, completely naïve BALB/cj mice were administered $2\times10^4$ PyRAS and evaluated by minigene-transfected P815 ELISPOT one week later. In mice exposed only to PyRAS, the only detectable response was to the pool for PY03376, which encodes P. yoelii malate dehydrogenase (PyMDH) (FIGS. 2E and 2F).

Figure 3:
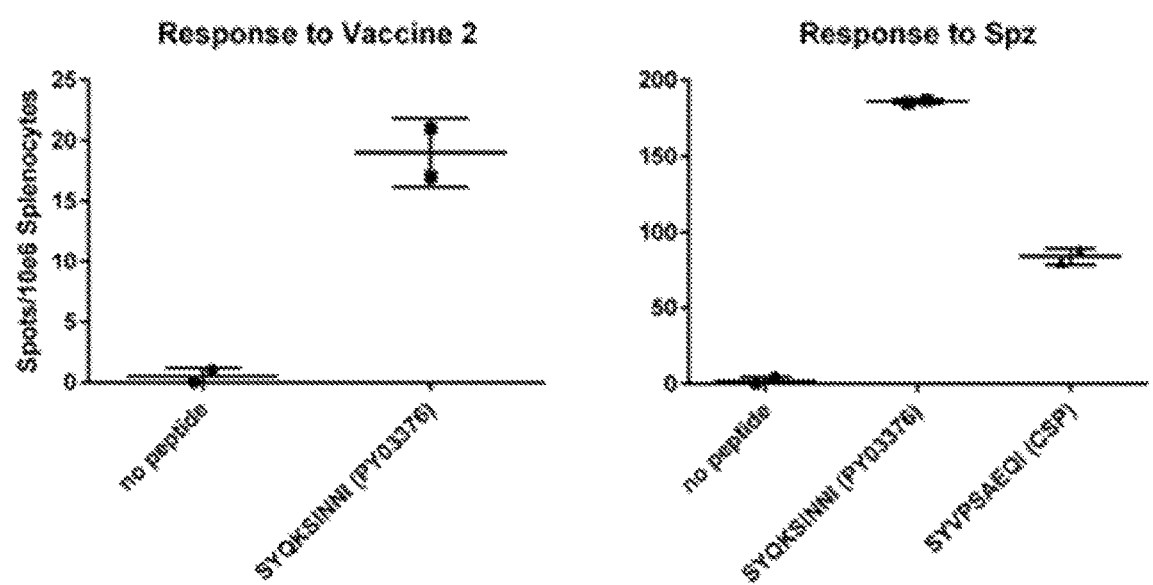
FIG. 3 shows the results of an antigen screening method according to certain embodiments described herein. In this FIG., SYQKSINNI was identified as the minimal target epitope of the novel Plasmodium antigen malate dehydrogenase encoded by PY03376. Both Vaccine 2 (left) and exposure to whole sporozoites in the absence of vaccination (right) induce IFNγ responses against SYQKSINNI. Y-axis, IFNγ spots/$10^6$ splenocytes. X-axis, target peptides.
Figure 4:
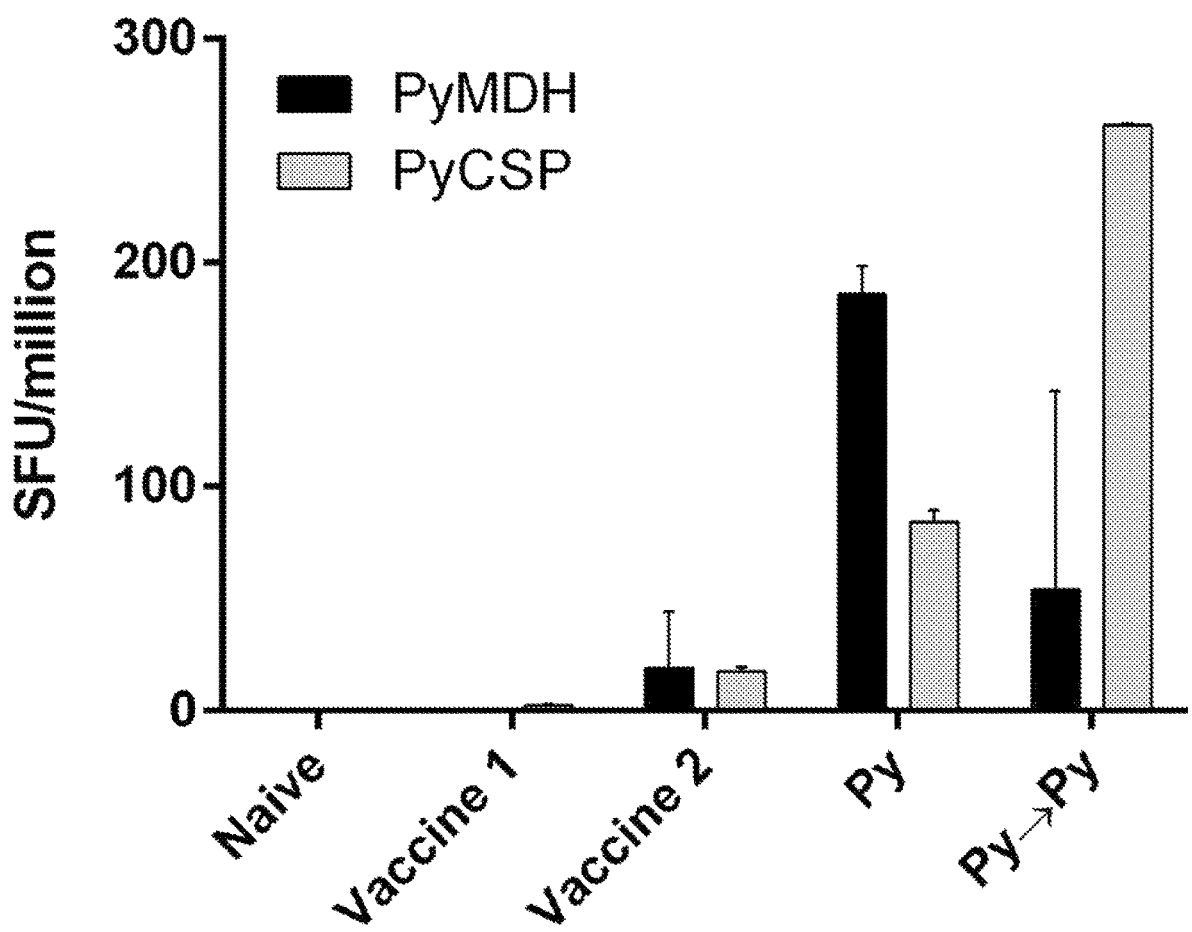
FIG. 4 shown the identification of SYQKSINNI as a dominant natural epitope in P. yoelii malate dehydrogenase. Cryopreserved splenocytes were obtained from library-vaccinated mice (Vaccine 1 or Vaccine 2) or from mice singly (Py) or doubly (PyPy) with doses of 1×104 wild-type Py sporozoites administered with azithromycin (0.8 mg/d) on Days 1-3 post-immunization); for PyPy, immunizations were spaced 3 wks apart. In all situations, splenocytes were harvested 6 d after the final immunization. Cells were thawed and tested by IFNγ ELISPOT against purified peptides corresponding to PyMDH (SYQKSINNI), PyCSP (SYVPSAEQI) and PyL3. Bars indicate mean and 95% confidence interval.

Identification of a Class I epitope in P. yoelii malate dehydrogenase (PY03376). Three adjacent minigene pools from P. yoelii malate dehydrogenase (PyMDH) were targeted in the primary screens. These pools included a total of 23 overlapping minigenes that were required to encode all permutations of four closely-spaced, non-synonymous sequence variants reported in the genome of P. yoelii strain 17XNL. It is unknown whether these reported variations are genuine or are the result of sequencing errors. In an attempt to identify a targeted epitope, the translated sequence of each variant minigene was evaluated for predicted Class I MHC binding using the NetMHC Pred 3.4 tool (Lundegaard et al. 2008) (available at http://www.cbs.dtu.dk/services/NetMHC-3.4/). Prediction was limited to MHC Class I H2$^d$ molecules since mastocytoma P815 targets used in the screens do not express MHC class II. The peptide SYQKSINNI yielded strong predicted binding characteristics for H2-K$^d$ and corresponded to a homologous, invariant sequence reported for P. berghei (PBANKA_1117700) Malate Dehydrogenase (MDH). This peptide was synthesized and tested by ELISPOT using frozen splenocytes from animals vaccinated with Vaccine 2 and from animals exposed to one or two doses of $1\times10^4$ Py wild-type sporozoites with concurrent prophylactic azithromycin drug treatment to prevent onset of erythrocyte-stage infection. Both responder populations exhibited a specific IFNγ response to peptide SYQKSINNI (FIG. 3), identifying SYQKSINNI as the minimal target epitope. Animals exposed to two doses of Py sporozoites was reduced compared to a single dose of sporozoites (FIG. 4). Sequencing of a genomic PCR product amplified from the P. yoelii 17XNL isolate used for PyRAS production confirmed that SYQKSINNI was the encoded peptide. Sequencing revealed no evidence of nonsynonymous variation within the SYQKSINNI-coding region.

The same approach was used to bioinformatically predict H2$^d$ and H2$^b$ binders for PY00619, PY00638, and PY01906. The PY00619, PY00638 and PY01906 minigene pools were indeed antigenic as they were each able to induce >100 SFU/million when administered to mice as a single pool gene gun immunization (data not shown).

Figure 5:
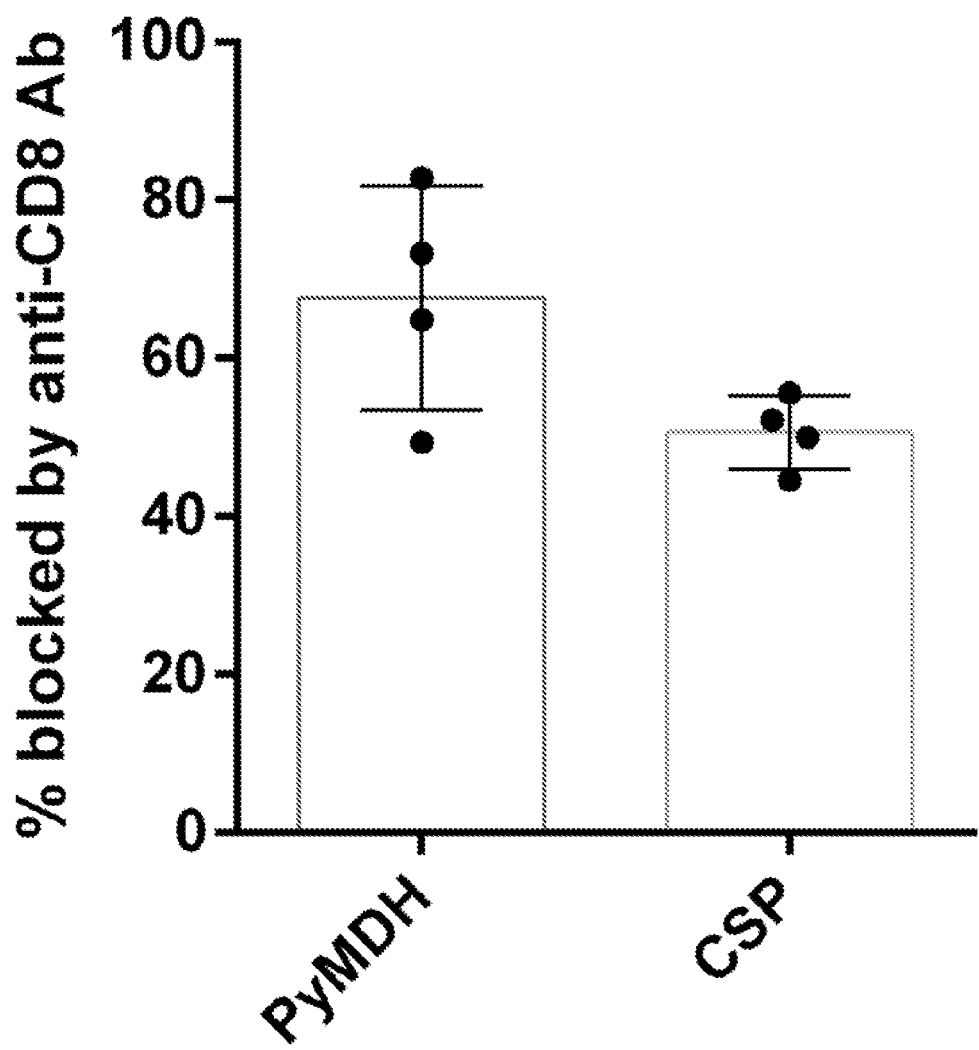
FIG. 5 illustrates that the PyMDH-specific response is CD8 T cell-dependent. ELISPOT wells were treated with anti-CD8 blocking antibody (clone 2.43, final 10 μg/mL) and compared to isotype-control treated wells. The y-axis shows the percentage reduction in SFU/million splenocytes for antibody-treated versus untreated wells. Splenocytes were from BALB/cj mice immunized with $5\times10^4$ wild-type P. yoelii sporozoites administered with azithromycin prophylaxis on Days 0-2 post-challenge. Bars indicate mean and 95% confidence interval.

When ELISPOT assays were conducted in the presence or absence of anti-CD8a antibodies, PyCSP- and PyMDH-specific T cell responses were comparably reduced, indicating IFNγ production in both antigen-specific responses was CD8+ T cell-dependent (FIG. 5).

Figure 6:
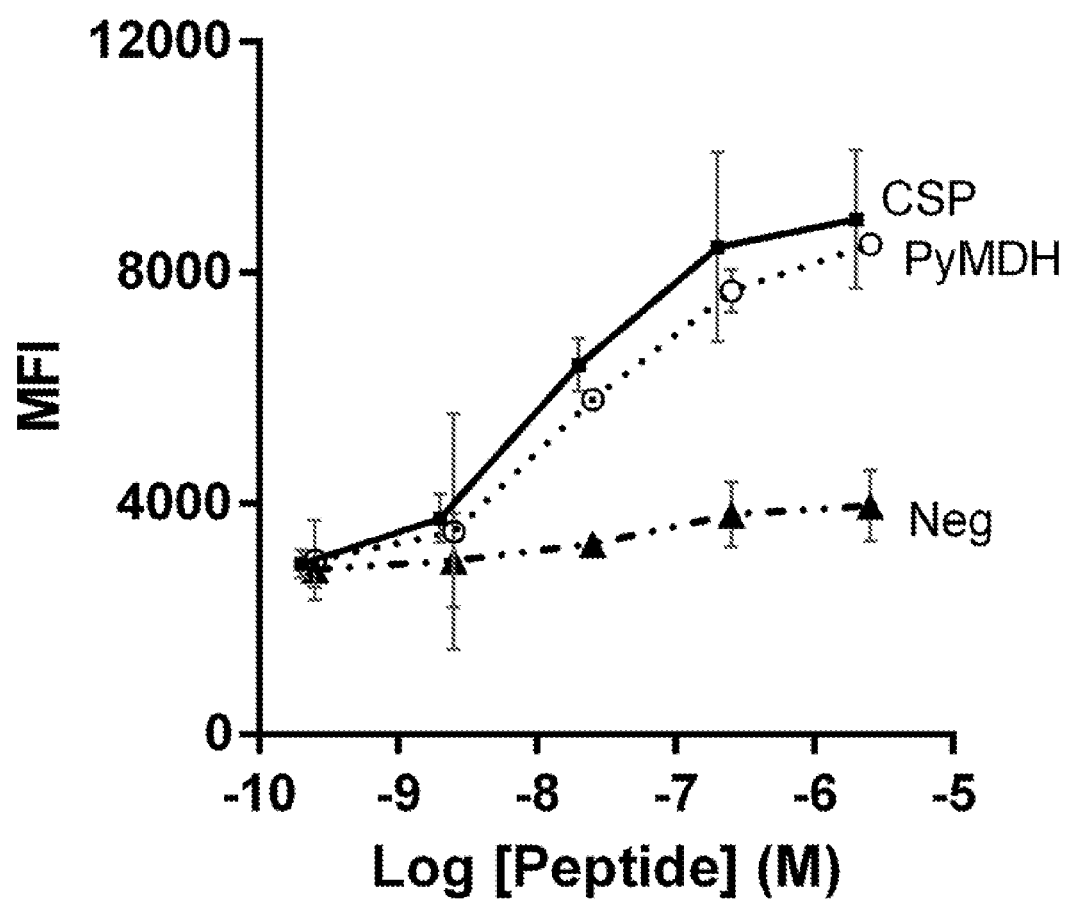
FIG. 6 shows that the PyMDH epitope binds to murine H2-Kd. RMA/S cells expressing H2-Kd were incubated with peptides for PyCSP (squares), PyMDH (circles) or non-specific peptide. PyCSP and PyMDH peptides stabilized H2-Kd, indicative of specific MHC binding. Error bars indicate the 95% confidence interval.

The MDH epitope SYQKINNI binds to murine H2-K$^d$. The affinity of SYQKSINNI for H2-K$^d$ was determined using an RMA/S lymphoma cell line expressing H2-K$^d$ as previously described [26, 54]. H2-K$^d$ was stabilized by a known binder (PyCSP-derived SYVPSAEQI) and with similar affinity by PyMDH-derived SYQKSINNI. The apparent Kd for the peptides was 11.6 nM (PyMDH) compared to 9.6 nM (PyCSP) (FIG. 6).

Figure 7:
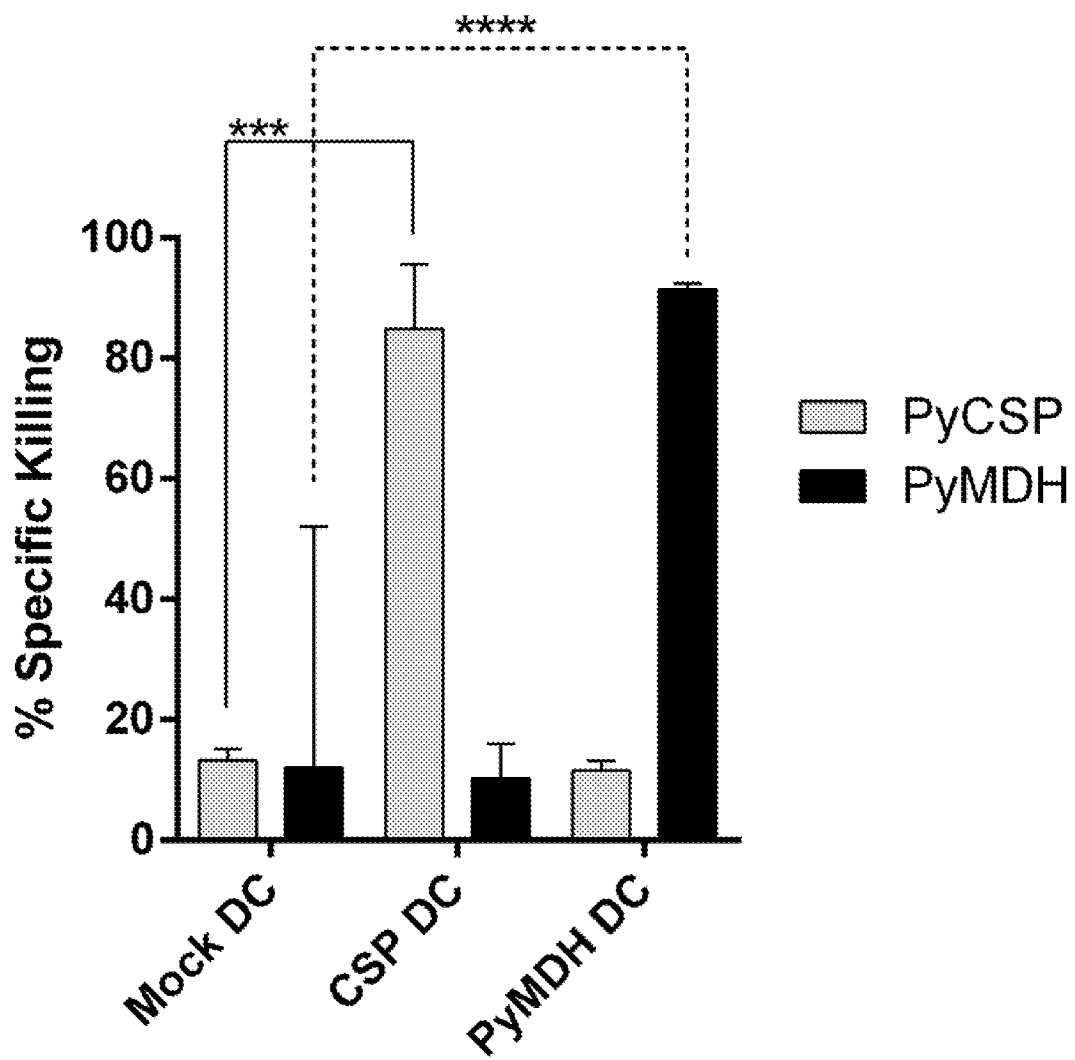
FIG. 7 illustrates that PyMDH-specific T cells are capable of antigen-specific cytotoxic killing. Mice were previously immunized with $1\times10^6$ mature DCs pulsed with 1 μg/mL pf the antigenic peptide (PyCSP DC or PyMDH DC). Six days later mice were administered equal numbers of PyCSP peptide-coated CFSEHI and PyMDH-peptide coated CFSELO target splenocytes; antigen-specific killing was monitored 18 hours later by flow cytometry. Like cytotoxic PyCSP-specific T cells, PyMDH-specific T cells demonstrate a high rate of antigen-specific killing. Bars indicate mean and 95% confidence interval; *p<0.001; **p<0.0001 (Student's t test).

Mice primed with SYQKSINNI peptide kill peptide pulsed targets in-vivo. To evaluate the functional capacity of PyMDH-specific T cells, BALB/cj (Thy1.2+) mice were primed i.v. with $2\times10^6$ GM-CSF-bone marrow-derived dendritic cells activated and pulsed overnight with lipopolysaccharide (0.1 µg/mL) and either 1 µg/mL PyCSP or PyMDH or no peptide. Six days later, splenocytes from Thy1.1 BALB/c mice were pulsed with PyCSP or PyMDH peptides or with no peptide and were differentially stained, mixed and injected into animals primed against individual peptides. Eighteen hours later, spleens were harvested and peptide-specific killing measured by flow cytometry. Animals immunized against the PyCSP peptide specifically killed 84% of PyCSP-pulsed targets, and animals sensitized to the PyMDH peptide killed 91% of PyMDH-pulsed targets (FIG. 7).

Figure 8:
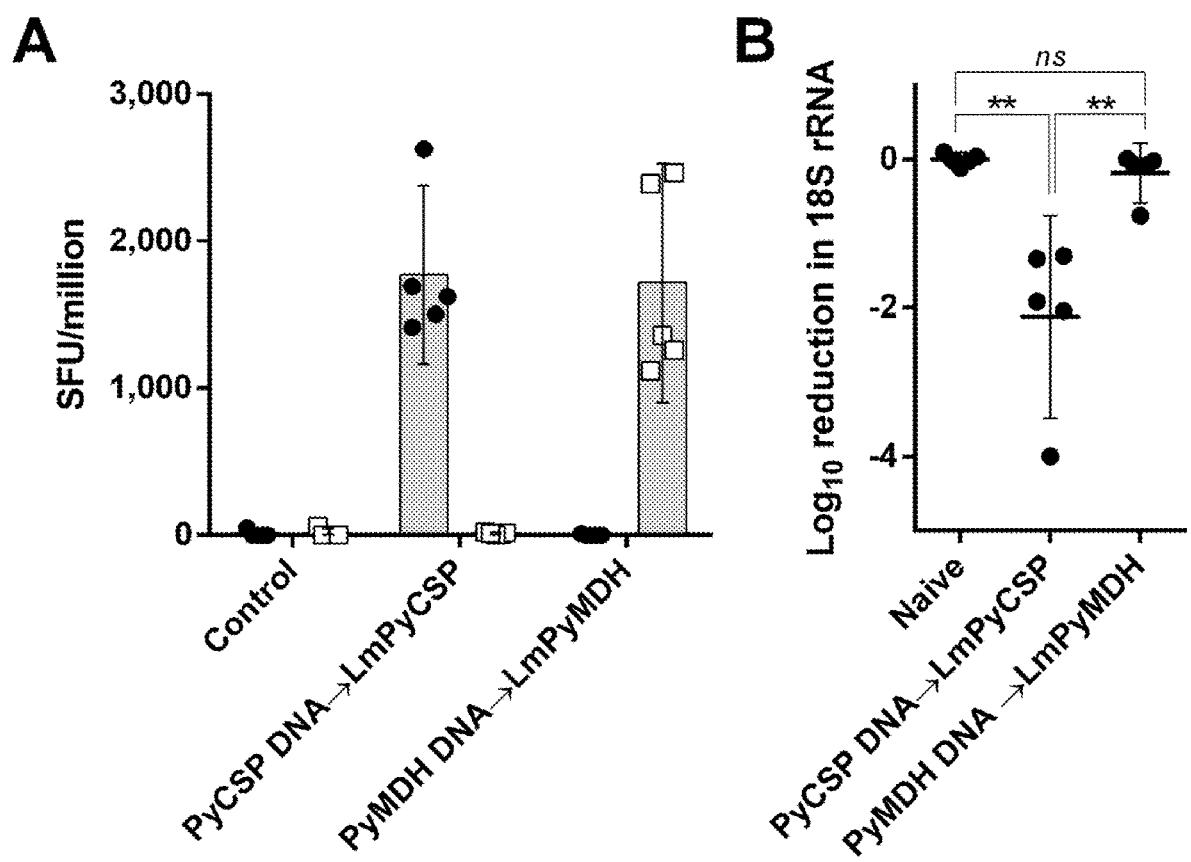
FIG. 8 illustrates antigen-specific, high frequency IFNγ-producing responses to PyCSP and PyMDH in appropriately immunized mice. BALB/cj mice were DNA gene gun vaccinated against Class I epitopes from PyCSP or PyMDH and boosted 21 days later with $5\times10^6$ cfu attenuated Listeria monocytogenes expressing the same epitope. Mice were challenged with $1\times10^4$ PyWT sporozoites i.v. and sacrificed for spleen and liver harvest 44 hours post-challenge. (A). ELISPOT performed on splenocytes at the 44 hr time point reflects the frequency of antigen-specific T cells at the time of challenge. Circles, PyCSP peptide; squares, PyMDH peptide; bars indicate mean and 95% confidence interval. (B). Liver stage infection was monitored by Plasmodium 18S rRNA RT-PCR. Bars indicate mean and 95% CI for Plasmodium 18S rRNA normalized to mouse GAPDH mRNA content; **p<0.01 (Student's t-test).

P. yoelii sporozoite challenge. Five animals per group were vaccinated with either PyCSP or PyMDH using a DNA prime/Listeria boost protocol. At a memory time point, all vaccinated mice plus five naïve infectivity control mice were challenged with $1\times10^4$ wild-type P. yoelii sporozoites. ELIS- POT performed at the time of liver harvest demonstrated antigen-specific, high frequency IFNγ-producing responses to PyCSP and PyMDH in appropriately immunized mice (FIG. 8A). Compared to infectivity control mice, 5/5 PyCSP-vaccinated mice showed significant vaccine-induced protection, with one animal showing undetectable Py 18S RNA in the liver indicating sterile protection (FIG. 8B). The Py 18S rRNA concentration in animals vaccinated with PyMDH was indistinguishable from that of the infectivity controls (FIG. 8B), indicating no protection despite high frequency PyMDH-specific T cell responses.

Figure 9:
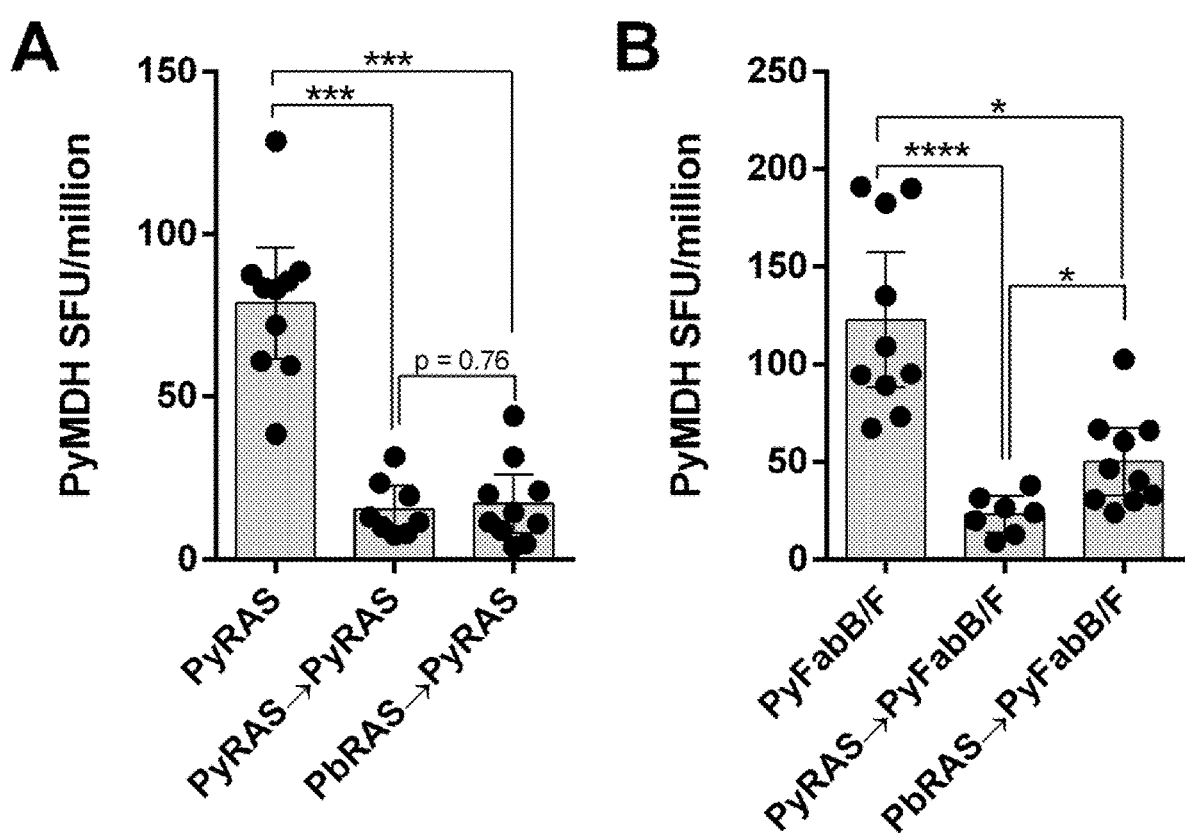
FIG. 9 shows that PyMDH-specific T cells can be recalled by heterologous cross-species immunization. (A) BALB/cj mice were immunized with nothing or with $1\times10^4$ PyRAS or PbRAS and three wks later all groups received 1.5×105 purified PyRAS. IFNγ ELISPOT was performed on splenocytes obtained 6 days after the final vaccination. (B) BALB/cj mice were immunized with nothing or with 1×104 PyRAS or PbRAS and three wks later all groups received $1.5\times10^5$ purified, genetically-attenuated Pyfabb/f- sporozoites. IFNγ ELISPOT was performed as in (A). Bars show mean +/−95% confidence interval; *p<0.05, *p<0.001; **p<0.0001 (Student's t-test).
Figure 10:
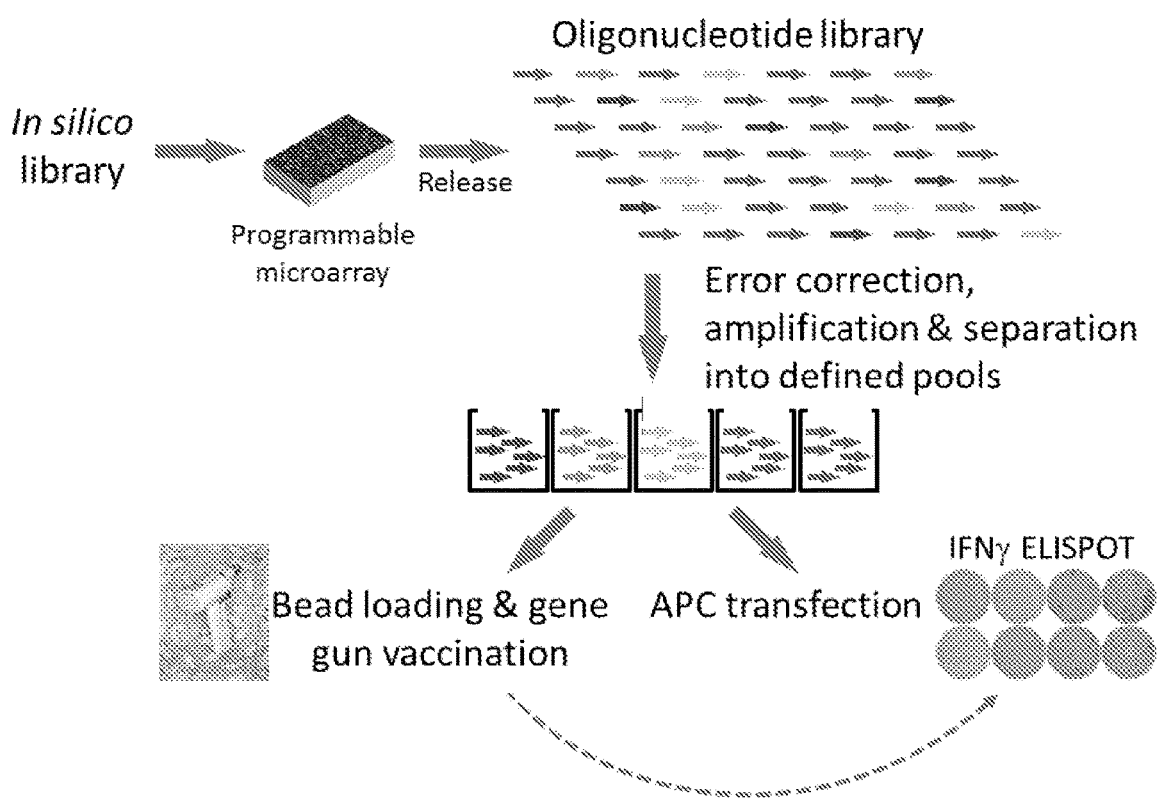
FIG. 10 is a schematic showing the method for antigen discovery in the HPI platform in accordance with one embodiment. This Figure illustrates an example of antigen screening and discovery to generate a library of defined pools of antigens, delivering those antigens to antigen presenting cells (APCs) and screening for an immune response using a screening method, in this illustration the screening method is INFγ ELISPOT.

Heterologous cross-species immunization with a late-arresting sporozoite re-expands the PyMDH-specific T cell population more than homologous immunizations. Previous studies showed that T cell responses to pre-erythrocytic antigens could either be expanded by repeated homologous (same-species) sporozoite immunization (e.g., CSP-specific CD8 T cells) or failed to re-expand (e.g., L3-specific CD8 T cells) (Murphy et al. 2013). Recent unpublished work has shown that immunization with two different murine-infecting Plasmodium species (P. yoelii 17XNL and P. berghei ANKA) could recall the L3-specific response to the epitope shared between species if the secondary immunization was with a late-arresting, genetically attenuated sporozoite (S. Murphy, pers. comm.-manuscript in review). Since the PyMDH epitope was also conserved between P. yoelii and P. berghei, mice underwent homologous or heterologous immunizations with combinations of PyRAS, PbRAS and Pyfabb/f- parasites. As observed for L3, when RAS parasites were used, neither homologous (PyRAS→PyRAS) nor heterologous (PbRAS→PyRAS) regimens re-expanded the PyMDH-specific cells (FIG. 9A). However, when the secondary immunization was switched to the less-attenuated Pyfabb/f-strain, the heterologous regimen (PbRAS→Pyfabb/f-) expanded PyMDH-specific responses more so than the homologous regimen (PyRAS→Pyfabb/f-), although not to the level observed with a single Pyfabb/f-immunization (FIG. 9B). This finding suggests that PyMDH-specific responses and those against other proteins with similar protein expression kinetics may be boosted by heterologous more so than homologous species immunizations.

Discussion

In these proof-of-principle studies, minigene vaccination resulted in the identification of four novel T cell antigens from among 89 pre-erythrocytic stage P. yoelii proteins. These included one dominant antigen encoded by PY03376 (PyMDH), and three antigens encoded by PY00619, PY0638 and PY01906 minigene pools. The peptide SYQK-SINNI was identified as a major PyMDH epitope. Robust responses against PyMDH were detected in animals receiving the vaccine alone and in response to sporozoite immunization in the absence of DNA vaccination. PyMDH-specific responses in DNA-vaccinated animals could be recalled by sporozoites. The PyMDH response was also evaluated in mice exposed to one or two rounds of sporozoite immunizations. The PyMDH-specific response was not potently recalled by homologous sporozoite immunizations, although the epitope is shared with P. berghei ANKA MDH and recall could be partially augmented by immunization with two different species of murine-infecting Plasmodium sporozoites. Thus, PyMDH appears to be an antigen in the same category as that of the recently described pre-erythrocytic P. yoelii ribosomal protein L3, which also displayed robust pre-erythrocytic immunogenicity but no protective efficacy and poor recall by repeated homologous sporozoite exposures (Murphy et al. 2013).

Animals receiving PyRAS 16 days after the final DNA library vaccine exhibited low level responses against PY00619 and PY00638 minigene pools but not to PY01906, and additional studies will be required to determine whether these responses represent true parasite recall or simply residual, declining responses from the initial DNA vaccination. Each of these three minigene pools was able to induce IFNγ responses in mice vaccinated with single pool DNA vaccines.

Because robust responses against PyMDH are not protective, the epitope may not be displayed on the surface of an infected hepatocyte harboring live proliferating parasites, or may be presented by the hepatocyte at a time point that is too late to provide protection. To be displayed on the surface of the hepatocyte, PyMDH would probably need to be exported from the parasite and across the hepatocyte-derived vacuole membrane to the hepatocyte cytoplasm. However unlike erythrocyte-stage parasites (Hiller et al. 2004; Marti et al. 2004), there is currently no known consensus motif that directs pre-erythrocytic protein export from the vacuolar parasite to the hepatocyte cytoplasm. Responses to PyMDH-like epitopes may be driven either entirely or in part by cross-presentation of dead or dying parasites. Other antigens with similar response profiles have been identified (Murphy et al. 2013; Van Braechel-Budmir & Harty 2015; Doll et al. 2014). This type of antigen may represent an immune evasion strategy employed by the parasite whereby epitopes derived from proteins that are not protective serve as "decoys", directing immune system resources toward non-protective targets. There is increasing evidence that this decoy antigen phenomena also occurs in bacterial and viral infections (Novotny & Bakaletz 2003; Guo et al. 2008). Such antigens may be under selective pressure to remain invariant as T cell responses against them could promote survival of the parasite. In contrast, T cell epitopes from proteins that are protective are likely to be expressed and presented by hepatocytes during liver-stage infection and therefore may be under selective pressure to alter their primary sequence to avoid immune detection. Separating antigenic protective antigens (the "wheat") from dispensable antigens such as PyMDH and P. yoelii ribosomal protein L3 (the "chaff") represents a major hurdle to the understanding of the Plasmodium-specific T cell repertoire and to development of effective subunit vaccines for malaria. The HPI platform described herein can effectively screen for and distinguish between such antigens.

During construction of the vaccines reported here, each of the more than 100 minigene pools (10 cloned minigenes/pool) in each vaccine were individually precipitated onto separate aliquots of gold beads in parallel in an effort to promote diverse responses against multiple vaccine-encoded antigens. Such physical segregation of antigens onto different pools of gold beads is known to promote both antibody and T cell response diversity in other studies of gene gun-delivered antigens (Hooper et al. 2000; Hooper et al. 2003; Fuller et al. 2012).

Several methods may increase the intensity and breadth of responses induced by complex DNA library vaccines. First, as mentioned earlier, a standard 5' UTR and a ubiquitin fusion design has been adopted. This design has proven superior to the design used in the LC3-based vaccines. Ubiquitin-tagged proteins have shown increased CD8+ T cell immunogenicity in many systems (Reguzova et al. 2015; Hospers et al. 2009; Imai et al. 2008; Goldwich et al. 2008; Fu et al. 1998) including for some malaria DNA vaccine antigens (Dobano et al. 2007). Simply increasing the dose of DNA on gold beads is unlikely to yield a significant effect as previous titration studies with the gene gun (Pertmer et al. 1995) suggest that the dose of DNA required to stimulate a response is well within the range of each construct achieved in this protocol. In contrast, increasing the number of DNA vaccination cartridges administered per animal would result in an increase in the number of DNA-coated particles delivered to dermal APCs, potentially boosting the number of responders induced against multiple antigens. In addition, using the sub-optimal CSP minigene, novel adjuvants targeting B7 family inhibitory receptors were tested and a significant increase in the number of responders induced was observed. Furthermore, a P815 cell line that overexpresses the co-stimulatory molecule B7.1 was tested (La Motte et al. 1998) as APCs in minigene-transfected ELISPOT screening assays and observed five-fold higher sensitivity for IFNγ producing cells, indicating that additional antigens may be discoverable by ELISPOT with optimized transfection-compatible APCs.

Example 2: Induction of a T Cell Response Against a Protective Antigen During HPI Minigenes encoding three known *P. yoelii* epitopes (CSP, ribosomal protein L3 and Malate Dehydrogenase) each separately linked to an amino-terminal Ubiquitin tag, were spiked into separate minigene pools within a minigene expression library encoding 13 irrelevant proteins. Each pool was combined with adjuvant and loaded onto gold beads separately as described for highly parallel immunization, then combined into a single vaccine. Mice were immunized with a single prime and two boosts at week 4 and 8. Mice were harvested on week 12 and an ELISPOT was performed to assess responses against each spiked antigen (FIG. 17).

Example 3: Optimized Synthetic Minigene Vaccination and Discovery of Protective Vaccine Subunits Here, a follow-on proof-of-concept study is performed to synergistically apply several enhancements to test 200 highly expressed pre-erythrocytic stage *Plasmodium* antigens. Novel antigens discovered using this pipeline are also tested for protective efficacy using murine models for vaccine development. Enhancements to the HPI system tested here improve sensitivity by including better antigen targeting, incorporating novel genetic adjuvants, using potent nanoplasmid backbones and adding enhanced target cell lines for screening.

Antigen Discovery

A summary of the high-throughput HPI platform used in the method described below is illustrated in FIG. 10. This method can define a large set of vaccine-inducible, parasite recalled CD8 T cell responses. And, although the methods below are directed to malaria, the platform can be adapted for other pathogens including complex organisms and for antigenically diverse and/or emerging pathogens.

Library design and electrochemistry. In this example, an antigen library is generated for use with certain embodiments described herein. In this example, 200 pre-erythrocyte stage proteins are selected based upon published proteomics and expression microarray data. This represents ~10% of the pre-erythrocytic proteome. In this example, coding domains of these genes from *Plasmodium yoelii* 17XNL are computationally arranged into 33-codon fragments overlapping by 14 codons on each end. These short open reading frames (ORFs) are codon optimized for mammalian expression. Additional sequences are added to allow cloning. The final ~150 bp minigenes are produced as custom libraries by massively parallel microarray electrochemistry (CustomArrays, Inc., Bothell, Wash.). The oligonucleotides are cleaved from the array and provided as a single pool. The complete pre-erythrocytic gene library as described in this example requires a total of 4,000 minigenes.

Post-electrochemistry library construction. Raw microarray-synthesized oligonucleotide libraries have a high error rate. In this example, to select accurate oligonucleotides for each minigene, a variation of "Dial-out" technology is used (Schwartz & Shendure 2012). This step involves a single amplification reaction for each set of oligos using primers that add random sequence "tags" onto both ends of each oligo. The tagged library is sequenced by next-generation sequencing technologies (Illumina MiSeq), which reveal accurate oligos along with their associated unique tag pairs. Each accurate oligo is then re-amplified individually using the flanking tags as primer sites. An acoustic transfer liquid handling robot may be used for large-scale library construction. This allows for rapid "cherry picking" and transfer of appropriate pre-synthesized primers, thereby eliminating the cost of unique dialout primers while enabling the efficient, accurate setup of thousands of individual PCR reactions required for large-scale library construction. For smaller-scale library construction, traditional Dial-out PCR may be performed by purchasing specific primers as determined by tagged library sequencing results. Real time qPCR may be performed with melting curve analyses for each minigene to assess successful amplification. Failures may be re-amplified using alternate tags. Individual, error-corrected minigenes may be cloned into nanoplasmids (NTC9384R from Nature Technologies) in-frame with an amino-terminal Ubiquitin tag to promote CD8 T cell responses. Each minigene construct may be transformed into the appropriate host and cultured individually in deep 96-well plates. Cultures representing consecutive minigenes from a single protein may be combined into a pool and prepped using a Qiagen 96-Plus Endotoxin free kit. In this example, minigenes encoding sets of 50 proteins at a time are processed through this pipeline. In other embodiments, minigenes encoding sets of different numbers of proteins are processed through this or a similar pipeline. In this example, randomly-selected minigenes may be sequenced from each plate to confirm the performance of the pipeline. In addition, the finished library may be sequenced using Illumina technology to confirm representation and uniformity.

Vaccine formulation, delivery, screening, and analysis. In this example, nanoplasmid expression cassettes representing individual proteins are mixed with a traditional genetic adjuvant [for example, DNA encoding *Escherichia coli* heat-labile enterotoxin LT (Arrington et al. 2002)]. In some embodiments, a plurality of adjuvants may be included, for example a novel adjuvant that includes shRNA targeting PDL1/PDL2. In this example, material is loaded onto 1 mg of 1 μm diameter gold beads by conventional calcium chloride precipitation. Beads encoding groups of 12-13 proteins may be combined and loaded into gene gun cartridges using a commercial tube turning device. In this example, subjects (for example, groups of 5 Balb/c mice) are vaccinated with a plurality of cartridges encoding ~12 proteins each using a gene gun. These vaccinations may be referred to as DNA library vaccinations. In this example, DNA library vaccinations utilize a 'cluster' approach (Peng et al. 2008; Wick et al. 2011) at 0, 1 and 2 months followed by recall vaccination with sporozoites 3-4 weeks after the final library vaccination.

In this example, splenocytes are harvested 7 days after sporozoite vaccination, pooled from alike subjects and screened against all antigens included in the library vaccine by overnight direct ex vivo IFNγ ELISPOT using $1 \times 10^6$ splenocytes as effectors and $1 \times 10^6$ library-transfected B7.1-expressing P815 cells as APCs. A separate aliquot of cells may be transfected with and without GFP plasmid to evaluate transfection efficiency. ELISPOT controls may include empty expression cassettes as negative controls as well as CSP peptide (SYVPSAEQI) and a SYVPSAEQI-encoding minigene as positive controls for the vaccination regimen and screen, respectively. ELISPOTs in this example may be developed after 18 hours and counted using an automated reader.

Validation

In this example, immunogenic or proteins are downselected on the basis of protection in mice that are highly sensitized to the antigen(s) of interest as described below. The responses induced by the protocol described above may be reviewed in light of data on antigen expression, protein features, relative abundance, conserved vs. variable regions and other available data. Antigens that can be DNA primed and boosted and/or recalled by sporozoite immunization are of particular interest. In addition, sporozoite-only immunized subjects are analyzed to identify 'subdominant' antigens that are not induced primarily by sporozoite but that can be primed by DNA libraries and recalled by the parasite.

Construction of a Listeria sub-library expressing immunogenic proteins, DNA prime-Listeria boost, and protection. Certain embodiments described herein relate to a library-based DNA vaccination and screening approach that is a discovery tool capable of readily inducing and detecting T cell responses to antigens by ELISPOT. Because it is undesirable to falsely label antigens as non-protective, potentially protective antigens or fragments thereof may individually assessed for protective effects using a potent prime-boost regimen that maximizes antigen-specific T cell frequencies allowing for delineation between protective and non-protective outcomes. In some embodiments, full length proteins are used. In this example, mice are primed with DNA encoding each immunogenic protein and boost with non-lethal recombinant Listeria strains engineered to express the protein of interest.

GeneBlocks (IDT DNA, Inc.) encoding full-length coding sequence for each immunogenic protein are used to generate recombinant Listeria using pPL2-N4 (Lauer et al. 2002). Listeria-boosted vaccines can generate high frequency responses (Murphy et al. 2013).

DNA prime-Listeria boost and protection studies in mice. Mice (5 BALB/c per antigen) are DNA primed with minigenes from immunogenic protein-specific pools and boosted with attenuated Listeria encoding the corresponding full length protein. Two weeks after Listeria immunization, pooled PBMCs are evaluated for antigen-specific responses using minigene-transfected B7.1 P815s as described above. One month post-immunization, mice are challenged intravenously with 10,000 Py17XNL sporozoites and protection is assessed at 40-44 hours post-challenge by liver-stage RT-PCR. Splenocytes are cryopreserved at the liver harvest timepoint for future studies. Antigens that show protection in the BALB/c model are subsequently re-tested by DNA/Listeria immunization and challenged in the C57BL/6 model to test whether the antigens are applicable on a different MHC background.

Discussion

The studies described above provide proof of concept that the HPI platform described herein is applicable for discovery of protective antigens. Specifically, the HPI methods produce (i) a set of sequence-verified, codon-optimized P. yoelii minigenes encompassing approximately 150 proteins useful for vaccination and screening as described herein, and also for whole gene assembly for antibody screening at a later time; (ii) a large set of longer gene fragments in P. yoelii, including those that are protective in their respective models; and (iii) a pathogen-independent antigen discovery pipeline that can be flexibly applied to other pathogens.

Unbiased vaccination and screening with complex minigene libraries as described above can identify novel protective antigens not discoverable through screening of parasite hyperimmunized animals. This approach can identify a variety of antigenic proteins, a subset of which are useful vaccine subunits. Further, if applied to a comprehensive set of 1,000+ proteins, this unbiased approach represents at least three orders of magnitude increase in throughput compared with conventional "candidate antigen" approaches, and thus represents the best available opportunity to evaluate all possible candidates.

Advantages Over Conventional Approaches

While sporozoite-based approaches have induced experimental protection in humans (Seder et al. 2013)), evidence from animal models indicates that protection requires extremely high CD8+ T cell frequencies (Schmidt et al. 2010); Schmidt et al. 2008). The work discussed here suggests that sporozoite hyperimmunization leads to narrowed T cell responses against immunodominant, preformed antigens on the sporozoite though perhaps not expanded responses to later stage antigens (Murphy et al. 2013). Certainly, protective efficacy of immunodominant preformed antigens like CSP and TRAP/SSP2 discovered by conventional approaches have disappointed in clinical trials (Regules et al. 2011; Dunachie et al. 2006; Moorthy et al. 2003; Richie et al. 2012).

The approach described here diverges from mainstream methods in two significant ways. First, the minigene technology represents a comprehensive, high-throughput, unbiased method for evaluating T cell responses against hundreds or thousands of pathogen-encoded proteins. The libraries/vaccines described herein are codon-optimized for expression in mammalian antigen presenting cells (APCs) and are produced and screened in an ordered, non-redundant fashion. In contrast, conventional studies routinely assess responses against much smaller groups of manually cloned, non-codon optimized "candidate antigens", relying on guesswork and luck that a significant target is included in their analysis.

A second major advantage that the system described herein offers is that vaccinations are performed on naïve animals that have not been previously exposed to parasites. This is in contrast to conventional approaches that use hyperimmunization with whole organisms as the paradigm for antigen discovery. This is significant for two reasons. First, as discussed in the Examples below, the prevailing paradigm of sporozoite hyperimmunization leads to boosted responses against sporozoite-expressed antigens (e.g., CSP by Py→Py vaccination, FIG. 11) but fails to recall responses against antigens newly expressed in hepatocytes, even though primary sporozoite exposure primes such responses (e.g., L3 by Py→Py vs. Py only, FIG. 11) (Murphy et al. 2013). Vaccination of naïve animals with experimental vaccines followed by a single sporozoite boost may "level the immunological playing field", efficiently inducing responses to both sporozoite and liver-stage antigens. In addition, experimental vaccine priming followed by sporozoite boosting identifies sub-dominant antigens (i.e., antigens that are not detected following sporozoite exposure, but can be primed by gene gun and recalled by the parasite). Thus, the parasite likely has immune evasion pathways that effectively "hide" a subset of sub-dominant, protective antigens from the immune system.

Not all immunogenic antigens will be protective. Using the comprehensive, unbiased strategies of the methods described herein, it is likely that both protective ("wheat") and non-protective ('chaff') antigens will be encountered. 'Chaff' responses are an unfortunate immunological complication of parasite exposure. Such responses may be induced by antigen deposited during sporozoite migration from the skin to the liver (Stewart et al. 1988) and/or by dead or dying parasites. It is possible that the parasite has evolved to misdirect immune responses, promoting those against dispensable antigens as a mechanism of immune evasion. Certainly, many antigens revealed by homologous sporozoite immunization have proven to be non-protective (Murphy et al. 2013; Mishra et al. 2011). There is as-yet no definitive method to predict protective 'wheat' antigens. However, until such approaches are available, it is believed that a largely unbiased approach to candidate antigen selection is warranted. Consequently, the approach described by the embodiments disclosed herein may be most powerful when applied to large sets (1,000+) of candidate antigens. Thus, the minigene immunization/screening system may likely identify a moderately-complex list of ~50-100 proteins that are both immunogenic and amenable to the described vaccination technology out of every 1,000 proteins screened. By comprehensively studying these proteins to downselect a subset of antigens, commonalities amongst protective antigens that can be used to predict or enrich the search for additional protective antigens may be revealed in the remaining proteome.

Other advantages of the methods described herein are as follows. The molecular front-end of the pipeline is amenable to rapid vaccine reformulation to test different combinations of antigens and utilizes codon optimization to overcome the reduced expression observed when genes are directly cloned from AT-rich *Plasmodium* genomes and expressed in mammalian APCs. This approach to biolistic (gene gun) vaccination is equally innovative and uniquely suited to the library vaccine format. In this system, vaccine DNA is precipitated onto the surface of 1 µm diameter gold beads and propelled into the dermis using a pulse of pressurized nitrogen gas. This deposits DNA-coated gold beads directly into the cytoplasm or nucleus of dermal APCs, with most transfected APCs receiving 1-2 gold beads (D. Fuller, pers. comm.). To reduce antigen and T cell competition at the surface of the APC, pools of 10 minigenes from a single protein were individually loaded onto 1 µm gold beads. This approach has been shown to promote more diverse immune responses compared with particles loaded with a single highly complex DNA mixture where each DNA species is present at extremely low concentrations (Yager et al. 2010; Liu et al. 2006; Hooper et al. 2000; Rodriguez et al. 2002). While DNA electroporation (EP) can also induce robust CD8+ T cell responses, conventional EP approaches do not physically separate distinct antigens in a manner equivalent to that described above for gold bead/gene gun immunization.

Figure 12:
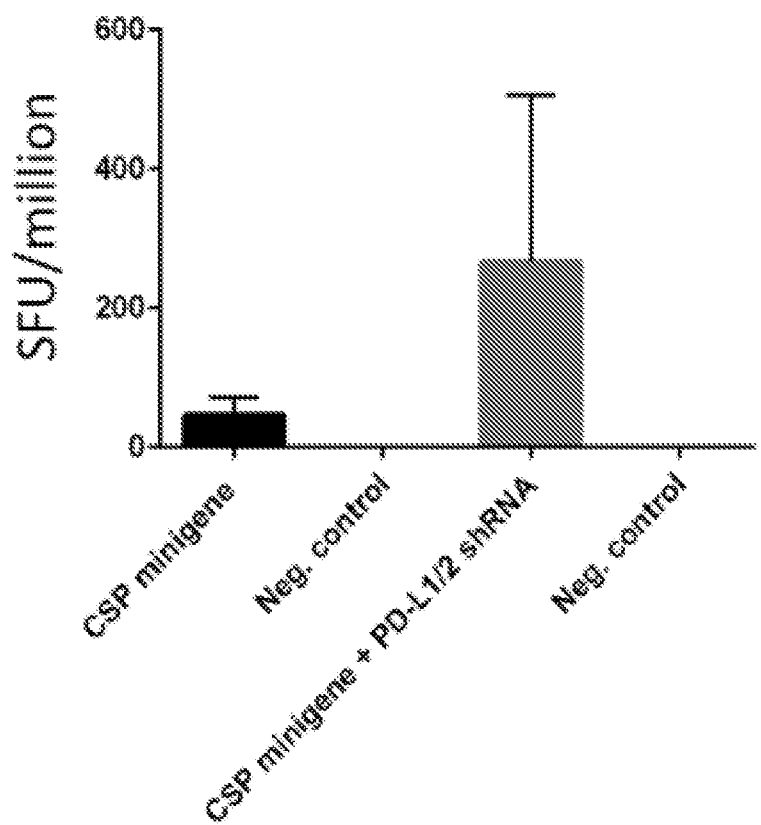
FIG. 12 shows that co-administration of PDL1/PDL2 shRNA enhances antigen-specific responses in accordance with some embodiments.
Figure 13:
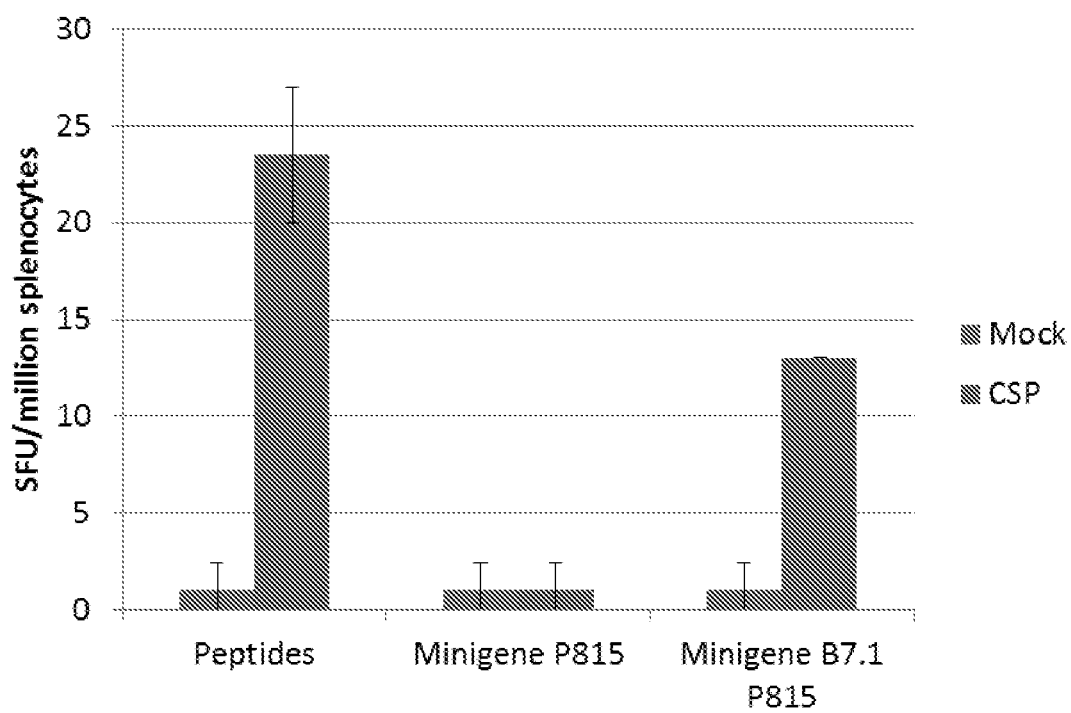
FIG. 13 is a bar graph illustrating that B7.1-expressing P815s increase the signal-to-noise in ELISPOT screening in accordance with some embodiments.

Beyond administration and APC segregation, the sensitivity of the minigene vaccination/screening pipeline has been improved in multiple ways. First, it was found that ubiquitin-tagged minigenes are more potent for triggering and recalling CD8+ T cell responses as compared to the LC3 tag used in initial studies (data not shown). Second, it was found that the potency of DNA library vaccines could be increased by co-administering DNA encoding shRNA to murine PDL1/PDL2 proteins to limit the effects of these immune inhibitory pathways. This addition markedly increased the frequency of CSP-specific T cell responses in BALB/c mice that received the CSP minigene in combination with PDL1/L2 shRNA compared to CSP minigene alone (FIG. 12). Third, the use of a nanoplasmid vector that increases the duration of antigen expression and does not contain an antibiotic resistance gene was adopted (Luke et al. 2009; Williams 2014)). Fourth, the signal-to-noise ratio was bolstered by >5-fold in P815-based ELISPOT screening by switching from conventional P815s to B7.1-expressing P815s (La Motte et al. 1998). When B7.1-expressing P815 cells were used for minigene screening the ability to robustly detect positive responses was increased as compared to normal P815 APCs (FIG. 13).

In addition, DNA primed and Listeria boosted mice against single model antigens such as CSP can be used to achieve protective outcomes post-sporozoite challenge (as shown in the Examples below). This indicates that the protection model described herein is effective.

In all, it is believed that the scientific and technological innovations described herein will converge to accelerate the development of a potent, safe and deliverable malaria vaccine for global use. The technological advances developed for malaria vaccines may also be easily applied to other high priority pathogens such as *Mycobacterium* tuberculosis, *Theileria parva* and additional emerging viruses. To this end, the embodiments described herein may be used to develop a Molecular Vaccine Core to tackle malaria and other infectious diseases affecting humans and livestock.

Example 4: Multi-Pathogen/Multi-Antigen Prophylactic Vaccine Development Through Highly Parallel Immunization Using the HPI platform described herein, multi-virus experimental HPI vaccines, and CD8 T cell antigen discovery is developed against 15 viruses of shared military and civilian importance. This approach is rapid, does not rely on intact pathogens and can be performed under biosafety level 1 (BSL1) conditions. In addition, the a proof-of-concept study described in this example is performed to evaluate the protective efficacy of HPI-identified antigens in a West Nile virus (WNV) model system.

Viruses investigated in this example include several that are of interest to the military as well as to civilians, including EBOV, Marburg (MARV), Lassa (LASV), Venezuelan equine encephalitis (VEE), Western equine encephalitis (WEE), Eastern equine encephalitis (EEE), DENV types 1-4, Chikungunya (CHIKV), Crimean-Congo hemorrhagic fever (CCHF) as well as Japanese encephalitis virus (JEV), enterovirus 71 (EV71) and WNV. Multi-virus HPI vaccines delivered by gene gun that demonstrate feasibility at multi-virus screening and/or WNV protection phases are poised to revolutionize vaccine development.

Methods

For this project, HPI is used to define a set of vaccine-inducible CD8 responses for 15 different viruses and then generate optimized HPI vaccines to immunization-challenge testing in mice using four of these viruses.

Immunization and challenge protocols. This project requires use of laboratory mice for immunogenicity and protection studies. The immune system is a complex multi-organ and tissue system comprised of innate and adaptive cellular and humoral components that cannot be adequately modeled in vitro, especially when antigen discovery from hundreds or thousands of potential antigens is the focus. Mice will be immunized using a gene gun. Gene gun vaccinations are well-tolerated and not painful. Most mice will be immunized repeatedly and later humanely sacrificed for immunogenicity studies. In Aim 2 protection studies, immunized animals will be challenged with virus to evaluate the protective effects of the vaccines. Such mice will be closely monitored post-challenge, and those exhibiting signs and symptoms consistent with severe disease (difficulty walking, seizures, >20% weight loss) will be humanely sacrificed. Some mice may die prior to humane sacrifice, but daily monitoring will be conducted to minimize this risk.

All mice are housed in IACUC-approved University of Washington animal facilities. All experimental protocols are subject to UW IACUC review and approval before any research can begin. Only trained and approved personnel are permitted to work on these animal studies.

Generation and defining a large set of vaccinatable responses to multiple viruses. In this example, HPI is used to define a set of vaccine-inducible CD8 responses for 15 different viruses. Protein-coding regions from the viruses in Table 1 (below) are selected bioinformatically. Sequences are computationally codon optimized, arranged into 33-codon fragments and modified to add targeting/expression tags.

TABLE 1

| Pathogen | Genome* | Minigenes/ Strain** | % HPI Vaccine*** |
|---|---|---|---|
| EBOV | 18-19 | 317 | 32% |
| MARV | 19 | 317 | 32% |
| LASV | 11 | 183 | 18% |
| VEE | 11.5 | 192 | 19% |
| WEE | 11.5 | 192 | 19% |
| EEE | 11.7 | 192 | 19% |
| JEV | 10.3 | 172 | 17% |
| DENV 1-4 | 10.7 | 10/serotype (720) | 18%/serotype (72%) |
| CHIKV | 11-12 | 185 | 18% |
| CCHF | 17.1-22.8 | 315 | 32% |
| WNV | 11 | 183 | 18% |
| EV71 | 6.6 | 110 | 11% |

(*kb; 20 unique aa/minigene; *~1000 minigenes/HPI vaccine)

Minigenes (i.e., nucleic acid fragments) are then synthesized by massively parallel electrochemistry (12,000/array), cleaved from the array and provided as a pool. The viruses in Table 1 require 3,081 minigenes (26% of array) so synthesis can accommodate additional sequence variants and/or other serotypes as needed. Raw oligonucleotides are error corrected by 'dial-out' PCR, cloned and next-gen sequenced. The approach described in this example produces up to ~4,000 error-corrected minigenes. Groups of 10 minigenes from the same parent gene are pooled, mixed with adjuvant plasmids (*Escherichia coli* heat-labile enterotoxin LT (Arrington et al. 2002) and shRNA for murine PDL1/PDL2), and loaded onto gold beads. Loading individual aliquots of beads with related minigenes promotes T cell repertoire diversity by physically segregating antigens at the level of antigen presentation (see Uniqueness). Finally, DNA-coated beads are further grouped and loaded into gene gun cartridges.

Groups of Balb/c mice are HPI vaccinated using 'cluster' priming (Peng et al. 2008; Wick et al. 2011) on Days 0 and 3 and boosted at 4 and 8 wks. Mice are sacrificed at acute and memory timepoints post-HPI. Splenocytes are pooled from alike mice and screened against all antigens in the corresponding HPI vaccine by IFNγ ELISPOT using library-transfected cell lines as APCs. HPI is conducted in BALB/c and later in C57BL/6 mice. Screening 4-5 HPI vaccines as described in this example is sufficient to test all of the proteins from the viruses identified in Table 1.

Optimization of the HPI vaccines and immunization-challenge testing. Based on the tests above, vaccines are reformulated into single-virus vaccines (e.g, WNV-, JEV-, EV71- or DENV2-only vaccines) or into a 'multi-virus' vaccine that includes antigens from two or more viruses (e.g., multi-virus vaccine against WNV, JEV, EV71 and DENV2) and administered to immunocompetent C57BL/6-background strains. Identified viruses with published challenge models were selected as the first candidates: DENV2 (Pinto et al. 2015), JEV (Miura et al. 1990), WNV (De Filette et al.). In addition. a novel T-cell sparing, myeloid-specific IFNα/βR-deficient model is used for EV71. The T cell repertoires in response to WNV, JEV, EV71 and DENV2 are incompletely mapped, and these agents have not previously been approached in a multi-pathogen context. After HPI, a subset of mice is screened to assess response diversity. Vaccinated and control mice are then be challenged with DENV2, JEV, EV71 or WNV. To gauge HPI-dependent protection, viremia and T cell responses are measured by RT-PCR and ELISPOT, respectively.

Further, protection against biosafety level 4 (BSL4) agents may be evaluated using HPI. For these protection studies, mice can be immunized in BSL1 conditions and the challenge can be conducted in containment in a BSL4 lab. Additional challenge models are available for the following agents in adult T cell immunocompetent mice: EBOV (Tsuda et al. 2015), MARV (Warfield et al. 2009), LASV (Goicochea et al. 2012), equine encephalitis viruses (Nagata et al. 2005; Reed et al. 2014) and CCHF (Canakoglu et al. 2015).

Discussion

The methods described in this and other working examples are amenable to rapid vaccine reformulation to test different combinations of antigens or introduce additional components and utilizes codon optimization to maximize expression. Biolistic (gene gun) delivery is well suited for pairing with the HPI format. When vaccine DNA is precipitated onto gold beads and shot into the dermis, the DNA-coated gold beads are deposited directly into the cytoplasm or nucleus of dermal APCs, with most transfected APCs receiving a single gold bead. To reduce antigen and T cell competition at the surface of the APC, pools of minigenes from a single protein are loaded individually onto 1 μm gold beads. This approach is known to diversify immune responses compared to immunization with a complex but completely mixed DNA sample (Yager et al. 2010; Liu et al.

2006; Hooper et al 2000; Rodriguez et al. 2002). Since vaccine-related immune interference is of growing concern (e.g., interference with co-administered WEE and EEE inactivated viruses in humans (Reisler et al. 2012), methods like HPI that are designed to circumvent interference are desirable. DNA electroporation (EP) can also induce CTL responses, but conventional EP does not physically separate distinct antigens like gene gun HPI. Finally, this system may be used with several novel genetic adjuvants (shRNA to murine PDL1/PDL2 and E. coli LT plasmids) that dramatically increase the frequency of antigen-specific responses as described above. These scientific and technological innovations allow for the HPI platform approach to be applied to numerous pathogens.

Example 5: Coxiella Burnetii Vaccine Development Through Highly Parallel Immunization In this example, HPI will be applied to Coxiella burnetii to identify new subunit vaccine candidates. The HPI approach is powerful and cost-effective, allowing us to examine nearly 50% of all C. burnetii protein-coding genes within the proposed scope of this award. HPI can be similarly applied to numerous other pathogens of military/civilian importance.

As described above, many pathogens trigger robust but non-protective immune responses against abundant pathogen-derived proteins. This type of "antigenic misdirection" allows infections to progress despite adaptive immune recognition. Despite this knowledge, most vaccine subunit discovery technologies still rely upon identification of antigens triggered during natural infectious exposures. For simple viral pathogens typically eliminated by adaptive immune responses, this may be appropriate. However, for complex pathogens like Coxiella, identification of the most effective cryptic sub-dominant or dominant vaccine subunits is critical for development of protective subunit vaccines. To more efficiently identify both subdominant and dominant protective antigens, a high-throughput vaccine strategy called "Highly parallel immunization" (HPI) was developed. HPI utilizes DNA vaccines to expand broad immune repertoires prior to infection. HPI vaccines are comprised of plasmid DNA libraries encoding 50-100 proteins per vaccine. Vaccines are delivered to naïve animals by gene gun in a manner that promotes a highly diverse immune response. T cell responses against each individual antigen are evaluated in parallel using ELISPOT assays. Responses to antigens are categorized as dominant (induced by vaccination or challenge), subdominant (induced by vaccination and recalled by challenge, but not induced by challenge alone) or non-significant (little or no response).

Figure 14:
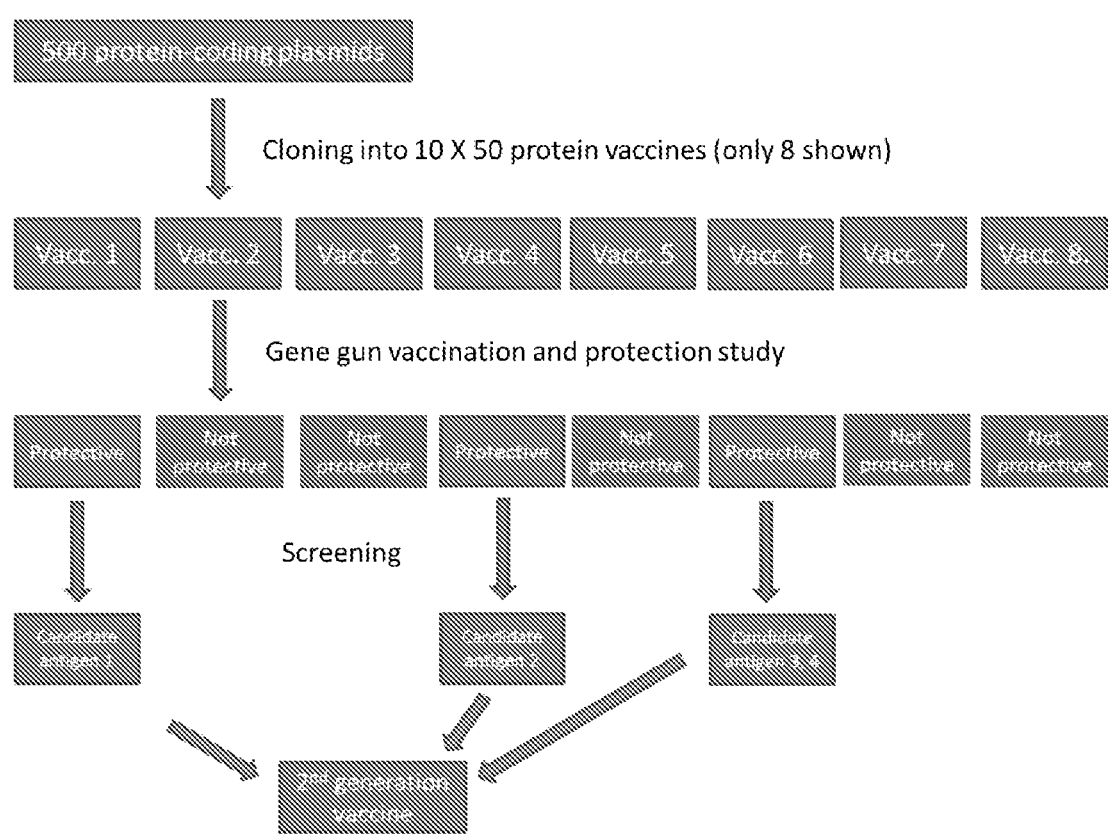
FIG. 14 depicts a general highly parallel immunization strategy for antigen discovery according to one embodiment. This protocol may be used for any pathogen or protein.
Figure 15:
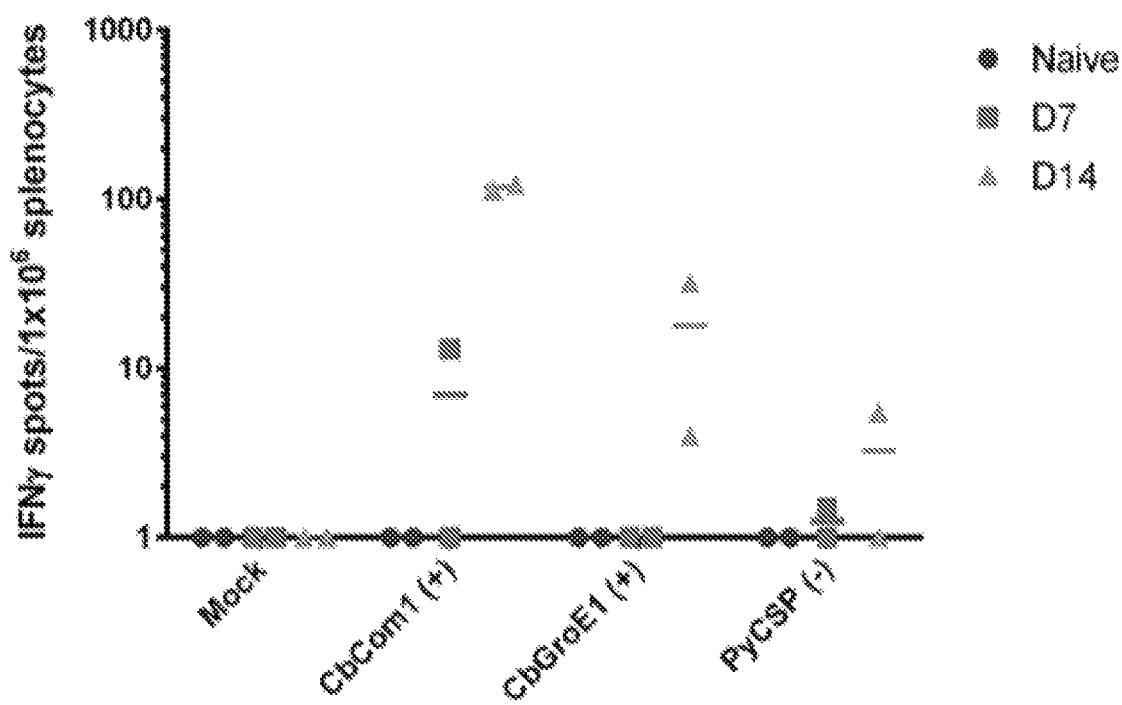
FIG. 15 is a graph showing results of C. burnetii DNA-transfected APC ELISPOT according to one embodiment. EL4 APCs were transfected with denoted recall antigens. Effectors used were spenocytes from C.b. Nine Mile phase II RSA439 straintionally characterized. ** indicates genes that elicited an immune response in accordance with working example 1.
Figure 17:
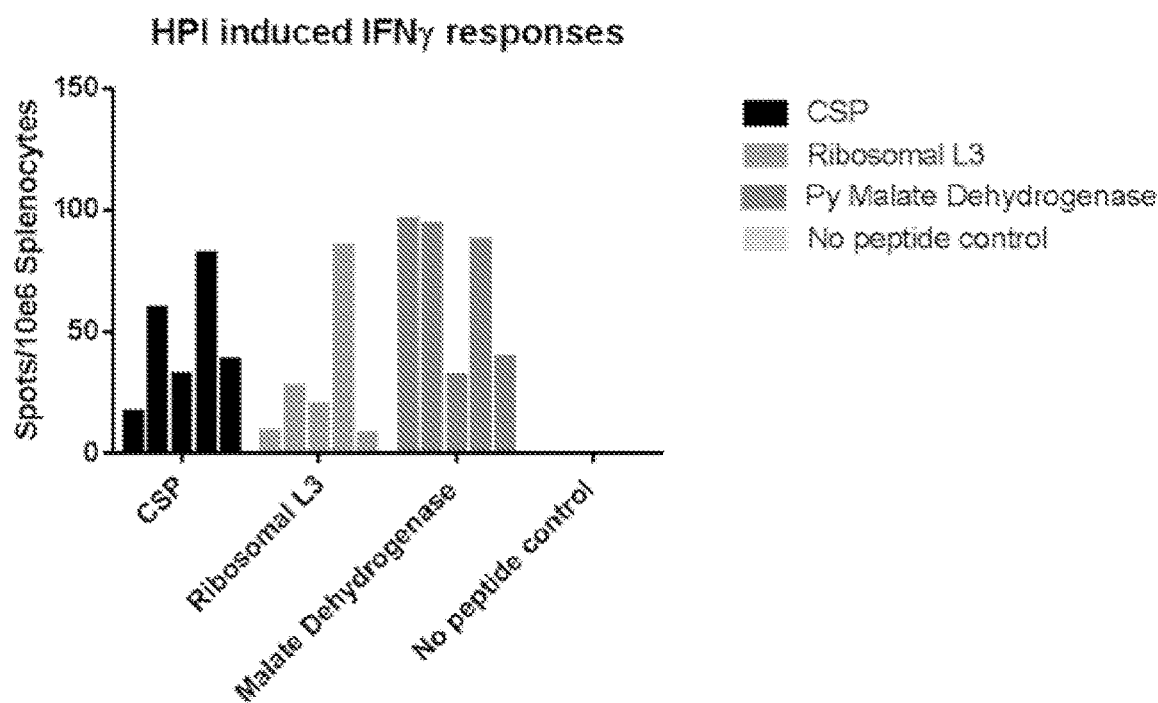
FIG. 17 illustrates HPI induction of responses against three known *P. yoelii* antigens (CSP, ribosomal protein L3, Malate Dehydrogenase), including a known protective antigen (CSP). Minigenes encoding three known Py antigens were spiked into a 13 irrelevant proteins. Delivered dose was <10 ng of each plasmid species/cartridge. Vaccinations were performed at weeks 0, 4 and 8. Responses were measured by IFNγ ELISPOT. Positive controls were wells stimulated with Concanavalin A (data not shown).

HPI is a high-throughput experimental system capable of defining critical T cell antigens for a given pathogen. HPI utilizes large, complex experimental DNA vaccines encoding up to 50 proteins per vaccine. Serial testing of multiple non-overlapping vaccines leads to evaluation of a significant percentage of the entire proteome expressed by the pathogen (FIG. 14). In practice, animals that have not been exposed to a pathogen are first gene-gun vaccinated with a multi-protein-coding vaccine (typically 10-50 proteins/vaccine). Animals are then challenged and evaluated for protection while memory T cell responses are mapped by IFNγ ELISPOT using target cells transfected with the same DNA vaccine library used for vaccination (FIG. 15). Multivalent vaccines targeting the major antigens can then be rapidly reformulated for immunization-challenge studies. Here, large experimental C. burnetii HPI vaccines can be developed using HPI, and T cell antigen discovery and immunization-challenge studies can be performed using an attenuated strain of C. burnetii. Much of the work can be performed under BSL1/2 conditions.

A C. burnetii infection model has been developed in C57BL/6 mice that recapitulates the tissue-specific lesions and bacterial kinetics reported in immunocompetent, but symptomatic acute Q fever patients. Briefly, mice are challenged with Nine Mile Phase II (NMII) strain (BSL2/ABSL2) via oropharyngeal route. This route and method of infection are relevant to natural exposures in humans (i.e. respiratory) and yield consistently similar pathology and bacterial burdens. Survival, clinical signs, body weight, bacterial burdens and distribution in combination with gross and histologic lesions were evaluated weekly (i.e., Day 7, 14 and 21) over a 21-day time course. In this model, mice survive infection but develop moderate granulomatous interstitial pneumonia and marked splenomegaly by Day 7. At 21 days post-infection, mice demonstrate resolution of lesions and substantial decreases in bacterial burdens. Thus, vaccinated mice will be challenged by airway exposure with C. burnetii to determine the efficacy of immunization in the context of lesion severity, bacterial burdens and distribution. This model can also be easily amended to evaluate protection by 2nd generation HPI vaccines in animals challenged with the Nine Mile Phase I variant C. burnetii (NMI; BSL3/ABSL3).

Library Construction and vaccine formulation. 500 C. burnetii proteins are bioinformatically selected for HPI. A novel high-throughput cloning strategy is then applied to produce an ordered, sequence-verified plasmid HPI library encoding all 500 proteins. Each open reading frame will be cloned in-frame with an LC3 tag, which delivers the encoded protein into both the class I and class II pathways (See FIG. 15 for example of C. burnetii Com1 and GroE1 HPI antigens recognized in the context of Class II MHC). Each plasmid species is cultured and isolated individually. Each plasmid is mixed with genetic adjuvants encoding E. coli LT and shRNAs targeting murine PDL1/PDL2 and precipitated onto 1 µm gold beads. DNA coated gold beads will be combined and loaded into gene gun cartridges as complex HPI vaccines.

Develop and refine immunization/challenge models for C. burnetii in mice. Initially, lesion severity (splenomegaly and histopathology), bacterial load (qPCR), and T cell responses to known C. burnetii antigens ComE1 and GroEL are evaluated at Days 7, 14 and 21 post-challenge. The time point closest to the maximum bacterial load is selected when specific T cell responses against known antigens can be clearly detected. If significant non-specific signal in the ELISPOT is encountered at all acute time points, protection is evaluated in one set of mice at the time point with maximal bacterial load, and T cell responses in a second cohort of mice that have been allowed to resolve the infection (e.g. Day 21).

Pilot scale HPI screen. C57/BL6 mice are immunized with two 50 protein sub-library vaccines and immunogenicity and organism-induced recall is evaluated against avirulent BSL2 C. burnetii. Groups of 10 mice will be "cluster" primed with two cartridges on Days 0 and 3 and boosted on Day 30 and 60. Five vaccinated mice are challenged with $1 \times 10^7$ bacteria (NMII) suspended in PBS via oropharyngeal route, while the remaining five vaccinated mice are evaluated without challenge. A group of five unvaccinated mice is challenged and evaluated in parallel. Mice are sacrificed on a predetermined optimal time point determined above, after which, spleens are weighed and harvested for ELISPOT analysis. Pathogen loads are evaluated using qPCR in the lung, liver, and spleen per established protocols, and histologic lesions will be evaluated to determine lesion severity in these tissues. Comparison of vaccinated only, vaccinated and challenged and challenged only will highlight antigens that require vaccination and can be recalled by challenge, but are not highly immunogenic by challenge alone. These responses are then correlated with protective effects.

Example 6: *Theileria Parva* Vaccine Development Through Highly Parallel Immunization East Coast fever, a devastating disease of cattle, sheep and goats, is caused by *Theileria parva*. In this example, the HPI platform described herein is used to immunize six age- and MHC class I-matched Holstein cattle with a small subset of known *T. parva* antigens.

Immunization follows a dose-escalation regimen starting with a cluster prime on Days 0 and 2 and a single boost on Day 28 using three gene gun cartridges per animal. Animals are screened for responses on Day 35 using interferon-gamma ELISPOTs, flow-cytometric cytotoxicity assays, and PIM ELISA or western blot to quantify CD4+, CD8+, and antibody responses. If no demonstrable responses are detected on Day 35, the booster dose is increased to 5 or 10 cartridges in 3 cattle each for a total of two additional boosts. Animals are again screened as above 7 days following the final boost.

Cattle are gene gun-immunized with the known *T. parva* (1-10) antigens, the N and C terminal (more conserved) regions of PIM, P67 (full length minus the signal peptide and membrane anchor), major merozoite surface antigen (p32), p104 and p150 (antigens in the apicomplast—highly expressed in pre-schizont stages) and *T. parva* cyclophilin. All antigens are adjuvanted with LT-encoding DNA and a bovine-specific shRNA immunoregulatory adjuvant. MHC class I-matched, previously infection and treatment method (ITM)-immunized cattle serve as positive controls. Two negative control animals are also immunized with gold beads carrying the LT adjuvant and the bovine-specific shRNA immunoregulatory adjuvant.

Based on the dosing schedule described above, the HPI platform is subsequently used to immunize five age and MHC class-I matched Holstein cattle with the 113 predicted-conserved antigens selected for screening by the Pullman group. All *T. parva* antigens, PIM, P67, p104, P150, and p32 are added to the vaccine mix. Immunization booster doses are administered on an as-needed basis. 4-6 weeks after last boost, animals are challenged with ITM and monitored for recall responses to gene gun-primed antigens. Two MHC class-I matched, previously ITM-immunized cattle are re-exposed to the same dose of ITM and used as a parasite-hyperimmunized positive control for parasite-only induced responses. Two negative control animals are also immunized with gold beads carrying the LT adjuvant and the bovine-specific shRNA immunoregulatory adjuvant.

REFERENCES

The references listed below, and all references cited in the specification are hereby incorporated by reference in their entireties, as if fully set forth herein.

Aguiar J C, Bolton J, Wanga J, Sacci J B, Iriko H, Mazeika J K, et al. Discovery of Novel *Plasmodium* falciparum Pre-Erythrocytic Antigens for Vaccine Development. PLoS one. 2015; 10(8):e0136109. Epub 2015/08/21. doi: 10.1371/journal.pone.0136109 pmid:26292257; PubMed Central PMCID: PMC4546230.

Arrington J, Braun R P, Dong L, Fuller D H, Macklin M D, Umlauf S W, et al. Plasmid vectors encoding cholera toxin or the heat-labile enterotoxin from *Escherichia coli* are strong adjuvants for DNA vaccines. Journal of virology. 2002; 76(9):4536-46. Epub 2002/04/05. pmid:11932419; PubMed Central PMCID: PMC155070. doi: 10.1128/jvi.76.9.4536-4546.2002

Barth S, Glick D, Macleod K F. Autophagy: assays and artifacts. The Journal of pathology. 2010; 221(2):117-24. Epub 2010/03/13. doi: 10.1002/path.2694 pmid:20225337; PubMed Central PMCID: PMC2989884.

Bergmann-Leitner E S, Mease R M, De La Vega P, Savranskaya T, Polhemus M, Ockenhouse C, et al. Immunization with pre-erythrocytic antigen CelTOS from *Plasmodium falciparum* elicits cross-species protection against heterologous challenge with *Plasmodium berghei*. PloS one. 2010; 5(8):e12294. Epub 2010/09/03. doi: 10.1371/journal.pone.0012294 pmid:20808868; PubMed Central PMCID: PMC2924390.

Canakoglu, N., et al., Immunization of knock-out alpha/beta interferon receptor mice against high lethal dose of Crimean-Congo hemorrhagic fever virus with a cell culture based vaccine. PLoS Negl Trop Dis, 2015. 9(3): p. e0003579.

Cardile, A. P., et al., Monitoring Exposure to Ebola and Health of U.S. Military Personnel Deployed in Support of Ebola Control Efforts-Liberia, Oct. 25, 2014-Feb. 27, 2015. MMWR Morb Mortal Wkly Rep, 2015. 64(25): p. 690-4.

Clyde D F, Most H, McCarthy V C, Vanderberg J P. Immunization of man against sporozite-induced falciparum malaria. The American journal of the medical sciences. 1973; 266(3):169-77. Epub 1973/09/01. pmid:4583408. doi: 10.1097/00000441-197309000-00002

De Filette, M., et al., Vaccination of mice using the West Nile virus E-protein in a DNA prime-protein boost strategy stimulates cell-mediated immunity and protects mice against a lethal challenge. PLoS One, 2014. 9(2): p. e87837.

Dobano C, Rogers W O, Gowda K, Doolan D L. Targeting antigen to MHC Class I and Class II antigen presentation pathways for malaria DNA vaccines. Immunol Lett. 2007; 111(2):92-102. doi: 10.1016/j.imlet.2007.05.007 pmid:17604849.

Doll K, Pewe L, Harty J. Protective capacity of CD8 T cells targeting a spectrum of *Plasmodium*-specific epitopes (MPF6P.735). The Journal of Immunology. 2014; 192(1 Supplement): 195.4.

Doolan D L, Hoffman S L. The complexity of protective immunity against liver-stage malaria. J Immunol. 2000; 165(3):1453-62. Epub 2000/07/21. pmid:10903750. doi: 10.4049/jimmunol.165.3.1453

Doolan D L, Sedegah M, Hedstrom R C, Hobart P, Charoenvit Y, Hoffman S L. Circumventing genetic restriction of protection against malaria with multigene DNA immunization: CD8+ cell-, interferon gamma-, and nitric oxide-dependent immunity. The Journal of experimental medicine. 1996; 183(4):1739-46. Epub 1996/04/01. pmid:8666931; PubMed Central PMCID: PMC2192484. doi: 10.1084/jem.183.4.1739

Doolan D L, Southwood S, Freilich D A, Sidney J, Graber N L, Shatney L, et al. Identification of *Plasmodium* falciparum antigens by antigenic analysis of genomic and proteomic data. Proceedings of the National Academy of Sciences of the United States of America. 2003; 100(17):

9952-7. Epub 2003/07/30. doi: 10.1073/pnas.1633254100 pmid:12886016; PubMed Central PMCID: PMC187898.

Duffy P E, Sahu T, Akue A, Milman N, Anderson C. Pre-erythrocytic malaria vaccines: identifying the targets. Expert review of vaccines. 2012; 11(10):1261-80. Epub 2012/11/28. doi: 10.1586/erv.12.92 pmid:23176657; PubMed Central PMCID: PMC3584156.

Dunachie, S J et al., 2006. Infect Immun 74:5933.

Epstein J E, Tewari K, Lyke K E, Sim B K, Billingsley P F, Laurens M B, et al. Live attenuated malaria vaccine designed to protect through hepatic CD8(+) T cell immunity. Science. 2011; 334(6055):475-80. Epub 2011 Sep. 10. doi: 10.1126/science.1211548 pmid:21903775.

Ferraro B, Talbott K T, Balakrishnan A, Cisper N, Morrow M P, Hutnick N A, et al. Inducing humoral and cellular responses to multiple sporozoite and liver-stage malaria antigens using exogenous plasmid DNA. Infection and immunity. 2013; 81(10):3709-20. Epub 2013/07/31. doi: 10.1128/IAI.00180-13 pmid:23897618; PubMed Central PMCID: PMC3811783.

Fidock D A, Bottius E, Brahimi K, Moelans I I, Aikawa M, Konings R N, et al. Cloning and characterization of a novel *Plasmodium* falciparum sporozoite surface antigen, STARP. Molecular and biochemical parasitology. 1994; 64(2):219-32. Epub 1994/04/01. pmid:7935600. doi: 10.1016/0166-6851(94)00012-3

Frevert U, Krzych U. *Plasmodium* cellular effector mechanisms and the hepatic microenvironment. Front Microbiol. 2015;6:482. Epub 2015/06/16. doi: 10.3389/fmicb.2015.00482 pmid:26074888; PubMed Central PMCID: PMC4445044.

Friedrich, T C et al., 2007. J Virology 81:3465. From the Centers for Disease Control and Prevention. Dengue fever among U.S. military personnel—Haiti, September-November, 1994. JAMA, 1995. 273(1): p. 14-5.

Fu T M, Guan L, Friedman A, Ulmer J B, Liu M A, Donnelly J J. Induction of MHC class I-restricted CTL response by DNA immunization with ubiquitin-influenza virus nucleoprotein fusion antigens. Vaccine. 1998; 16(18): 1711-7. pmid:9778746. doi: 10.1016/s0264-410x(98) 00134-0

Fuller D H, Rajakumar P, Che J W, Narendran A, Nyaundi J, Michael H, et al. Therapeutic DNA vaccine induces broad T cell responses in the gut and sustained protection from viral rebound and AIDS in SIV-infected rhesus macaques. PloS one. 2012; 7(3):e33715. doi: 10.1371/journal.pone.0033715 pmid:22442716; PubMed Central PMCID: PMC3307760.

Gibbons, R. V., et al., Dengue and US military operations from the Spanish-American War through today. Emerg Infect Dis, 2012. 18(4): p. 623-30.

Goicochea, M. A., et al., Evaluation of Lassa virus vaccine immunogenicity in a CBA/J-ML29 mouse model. Vaccine, 2012. 30(8): p. 1445-52.

Goldwich A, Hahn S S, Schreiber S, Meier S, Kampgen E, Wagner R, et al. Targeting HIV-1 Gag into the defective ribosomal product pathway enhances MHC class I antigen presentation and CD8+ T cell activation. J Immunol. 2008; 180(1):372-82. pmid:18097038. doi: 10.4049/jimmunol180.1.372

Guerin-Marchand C, Druilhe P, Galey B, Londono A, Patarapotikul J, Beaudoin R L, et al. A liver-stage-specific antigen of *Plasmodium* falciparum characterized by gene cloning. Nature. 1987; 329(6135):164-7. Epub 1987 Sep. 10. doi: 10.1038/329164a0 pmid:3306406.

Guo H, Zhou E M, Sun Z F, Meng X J. Immunodominant epitopes mapped by synthetic peptides on the capsid protein of avian hepatitis E virus are non-protective. Viral immunology. 2008; 21(1):61-7. Epub 2008 Mar. 22. doi: 10.1089/vim.2007.0082 pmid:18355123.

Hassan I A, Wang S, Xu L, Yan R, Song X, XiangRui L. Immunological response and protection of mice immunized with plasmid encoding Toxoplasma gondii glycolytic enzyme malate dehydrogenase. Parasite Immunol. 2014; 36(12):674-83. doi: 10.1111/pim.12146 pmid: 25244501.

Hiller N L, Bhattacharjee S, van Ooij C, Liolios K, Harrison T, Lopez-Estrano C, et al. A host-targeting signal in virulence proteins reveals a secretome in malarial infection. Science. 2004; 306(5703):1934-7. Epub 2004 Dec. 14. doi: 10.1126/science.1102737 pmid:15591203.

Hoffman S L, Vekemans J, Richie T L, Duffy P E. The march toward malaria vaccines. Vaccine. 2015a; 33 Suppl 4:D13-23. Epub 2015 Sep. 2. doi: 10.1016/j.vaccine.2015.07.091 pmid:26324116.

Hoffman S L, Vekemans J, Richie T L, Duffy P E. The March Toward Malaria Vaccines. Am J Prey Med. 2015b; 49(6 Suppl 4):5319-33. doi: 10.1016/j.amepre.2015 Sep. 11 pmid:26590432.

Hooper J W, Custer D M, Schmaljohn C S, Schmaljohn A L. DNA vaccination with vaccinia virus L1R and A33R genes protects mice against a lethal poxvirus challenge. Virology. 2000; 266(2):329-39. Epub 2000 Jan. 20. doi: 10.1006/viro.1999.0096 pmid:10639319.

Hooper J W, Custer D M, Thompson E. Four-gene-combination DNA vaccine protects mice against a lethal vaccinia virus challenge and elicits appropriate antibody responses in nonhuman primates. Virology. 2003; 306(1): 181-95. pmid:12620810. doi: 10.1016/s0042-6822(02) 00038-7

Hospers G A, Meijer C, Dam W A, Roossink F, Mulder N H. Construction of a triple modified p53 containing DNA vaccine to enhance processing and presentation of the p53 antigen. Vaccine. 2009; 28(2):386-91. doi: 10.1016/j.vaccine.2009.10.036 pmid:19878752.

Im, E J et al., 2011. PLoS Pathogens 7:e1002041.

Imai T, Duan X, Hisaeda H, Himeno K. Antigen-specific CD8+ T cells induced by the ubiquitin fusion degradation pathway. Biochem Biophys Res Commun. 2008; 365(4): 758-63. doi: 10.1016/j.bbrc.2007.11.034 pmid:18029260.

Kariu T, Ishino T, Yano K, Chinzei Y, Yuda M. CelTOS, a novel malarial protein that mediates transmission to mosquito and vertebrate hosts. Molecular microbiology. 2006; 59(5):1369-79. Epub 2006 Feb. 14. doi: 10.1111/j.1365-2958.2005.05024.x pmid:16468982.

Keitany G J, Sack B, Smithers H, Chen L, Jang I K, Sebastian L, et al. Immunization of mice with live-attenuated late liver stage-arresting *Plasmodium yoelii* parasites generates protective antibody responses to preerythrocytic stages of malaria. Infect Immun. 2014; 82(12):5143-53. doi: 10.1128/IAI.02320-14 pmid: 25267837; PubMed Central PMCID: PMC4249261.

Khusmith S, Charoenvit Y, Kumar S, Sedegah M, Beaudoin R L, Hoffman S L. Protection against malaria by vaccination with sporozoite surface protein 2 plus CS protein. Science. 1991; 252(5006):715-8. Epub 1991 May 3. pmid:1827210. doi: 10.1126/science.1827210

Kumar S, Miller L H, Quakyi I A, Keister D B, Houghten R A, Maloy W L, et al. Cytotoxic T cells specific for the circumsporozoite protein of *Plasmodium* falciparum. Nature. 1988; 334(6179):258-60. Epub 1988 Jul. 21. doi: 10.1038/334258a0 pmid:2456467.

Kunwar, R. and R. Prakash, Dengue outbreak in a large military station: Have we learnt any lesson? Med J Armed Forces India, 2015. 71(1): p. 11-4.

La Motte R N, Sharpe A H, Bluestone J A, Mokyr M B. Importance of B7-1-expressing host antigen-presenting cells for the eradication of B7-2 transfected P815 tumor cells. J Immunol. 1998; 161(12):6552-8. Epub 1998/12/23. pmid: 9862681.

Lauer, P et al., 2002. J Bacteriology 184:4177.

Liu, J., et al., Modulation of DNA vaccine-elicited CD8+ T-lymphocyte epitope immunodominance hierarchies. J Virol, 2006. 80(24): p. 11991-7.

Luke, J et al., 2009. Vaccine 27:6454.

Lundegaard C, Lamberth K, Harndahl M, Buus S, Lund O, Nielsen M. NetMHC-3.0: accurate web accessible predictions of human, mouse and monkey MHC class I affinities for peptides of length 8-11. Nucleic Acids Res. 2008; 36(Web Server issue):W509-12. doi: 10.1093/nar/gkn202 pmid:18463140; PubMed Central PMCID: PMC2447772.

Marti M, Good R T, Rug M, Knuepfer E, Cowman A F. Targeting malaria virulence and remodeling proteins to the host erythrocyte. Science. 2004; 306(5703): 1930-3. Epub 2004/12/14. doi: 10.1126/science.1102452 pmid: 15591202.

Mishra S, Rai U, Shiratsuchi T, Li X, Vanloubbeeck Y, Cohen J, et al. Identification of non-CSP antigens bearing CD8 epitopes in mice immunized with irradiated sporozoites. Vaccine. 2011; 29(43):7335-42. Epub 2011 Aug. 3. doi: 10.1016/j.vaccine.2011.07.081 pmid:21807053.

Miura, K., et al., A single gene controls resistance to Japanese encephalitis virus in mice. Arch Virol, 1990. 112(3-4): p. 261-70.

Moelans I I, Meis J F, Kocken C, Konings R N, Schoenmakers JG. A novel protein antigen of the malaria parasite *Plasmodium* falciparum, located on the surface of gametes and sporozoites. Molecular and biochemical parasitology. 1991; 45(2):193-204. Epub 1991/04/01. pmid: 2038355. doi: 10.1016/0166-6851(91)90086-I Moorthy, V S et al., 2003. Vaccine 21:1995.

Mueller A K, Labaied M, Kappe S H, Matuschewski K. Genetically modified *Plasmodium* parasites as a protective experimental malaria vaccine. Nature. 2005; 433 (7022):164-7. Epub 2004 Dec. 8. doi: 10.1038/nature03188 pmid:15580261.

Mullbacher A, Lobigs M, Kos F J, Langman R. Alloreactive cytotoxic T-cell function, peptide nonspecific. Scandinavian journal of immunology. 1999; 49(6):563-9. Epub 1999/06/03. pmid:10354367. doi: 10.1046/j.1365-3083.1999.00568.x Murphy S C, Kas A, Stone B C, Bevan M J. A T-cell response to a liver-stage *Plasmodium* antigen is not boosted by repeated sporozoite immunizations. Proceedings of the National Academy of Sciences of the United States of America. 2013; 110(15):6055-60. Epub 2013/03/27. doi: 10.1073/pnas.1303834110 pmid:23530242; PubMed Central PMCID: PMC3625320.

Nagata, L. P., et al., Efficacy of DNA vaccination against western equine encephalitis virus infection. Vaccine, 2005. 23(17-18): p. 2280-3.

Novotny L A, Bakaletz L O. The fourth surface-exposed region of the outer membrane protein P5-homologous adhesin of nontypable Haemophilus influenzae is an immunodominant but nonprotective decoying epitope. J Immunol. 2003; 171(4):1978-83. Epub 2003/08/07. pmid: 12902501. doi: 10.4049/jimmunol.171.4.1978

Nussenzweig R S, Vanderberg J, Most H, Orton C. Protective immunity produced by the injection of x-irradiated sporozoites of *Plasmodium berghei*. Nature. 1967; 216 (5111):160-2. Epub 1967 Oct. 14. pmid:6057225. doi: 10.1038/216160a0

Peng, S., et al., Cluster intradermal DNA vaccination rapidly induces E7-specific CD8+ T-cell immune responses leading to therapeutic antitumor effects. Gene Ther, 2008. 15(16): p. 1156-66.

Pertmer T M, Eisenbraun M D, McCabe D, Prayaga S K, Fuller D H, Haynes J R. Gene gun-based nucleic acid immunization: elicitation of humoral and cytotoxic T lymphocyte responses following epidermal delivery of nanogram quantities of DNA. Vaccine. 1995; 13(15): 1427-30. Epub 1995/01/01. pmid:8578820. doi: 10.1016/0264-410x(95)00069-d Pinto, A. K., et al., Defining New Therapeutics Using a More Immunocompetent Mouse Model of Antibody-Enhanced Dengue Virus Infection. MBio, 2015. 6(5).

Putrianti E D, Silvie O, Kordes M, Borrmann S, Matuschewski K. Vaccine-like immunity against malaria by repeated causal-prophylactic treatment of liver-stage *Plasmodium* parasites. The Journal of infectious diseases. 2009; 199(6):899-903. Epub 2009 May 13. pmid: 19434915. doi: 10.1086/597121

Reed, D. S., et al., Combined alphavirus replicon particle vaccine induces durable and cross-protective immune responses against equine encephalitis viruses. J Virol, 2014. 88(20): p. 12077-86.

Regules, J A et al., 2011. Expert Rev Vaccines 10:589.

Reguzova A, Antonets D, Karpenko L, Ilyichev A, Maksyutov R, Bazhan S. Design and evaluation of optimized artificial HIV-1 poly-T cell-epitope immunogens. PloS one. 2015; 10(3):e0116412. doi: 10.1371/journal.pone.0116412 pmid:25786238; PubMed Central PMCID: PMC4364888.

Reisler, R. B., et al., Immune interference in the setting of same-day administration of two similar inactivated alphavirus vaccines: eastern equine and western equine encephalitis. Vaccine, 2012. 30(50): p. 7271-7.

Reyes-Sandoval A, Pearson F E, Todryk S, Ewer K. Potency assays for novel T-cell-inducing vaccines against malaria. Current opinion in molecular therapeutics. 2009; 11(1): 72-80. Epub 2009 Jan. 27. pmid:19169962.

Richie, T L et al., 2012. Human Vacc Immunother 8:1564.

Robson K J, Hall J R, Jennings M W, Harris T J, Marsh K, Newbold C I, et al. A highly conserved amino-acid sequence in thrombospondin, properdin and in proteins from sporozoites and blood stages of a human malaria parasite. Nature. 1988; 335(6185):79-82. Epub 1988 Sep. 1. doi: 10.1038/335079a0 pmid:3045563.

Rodriguez, F., et al., Immunodominance in virus-induced CD8(+) T-cell responses is dramatically modified by DNA immunization and is regulated by gamma interferon. J Virol, 2002. 76(9): p. 4251-9.

Roestenberg M, McCall M, Hopman J, Wiersma J, Luty A J, van Gemert G J, et al. Protection against a malaria challenge by sporozoite inoculation. The New England journal of medicine. 2009; 361(5):468-77. Epub 2009/07/31. doi: 10.1056/NEJMoa0805832 pmid:19641203.

Ruckwardt, T J et al., 2010. J Immunol 185:4673.

Sanchez G I, Rogers W O, Mellouk S, Hoffman S L. *Plasmodium* falciparum: exported protein-1, a blood stage antigen, is expressed in liver stage parasites. Experimental parasitology. 1994; 79(1):59-62. Epub 1994 Aug. 1. doi: 10.1006/expr.1994.1060 pmid:8050527.

Schmidt, N W et al., 2008. PNAS 105:14017. Schmidt, N W et al., 2010. PLoS Pathogens 6:e1000998. Schwartz J J, Lee C, Shendure J. Accurate gene synthesis with tag-directed retrieval of sequence-verified DNA molecules. Nature methods. 2012; 9(9):913-5. Epub 2012 Aug. 14. doi: 10.1038/nmeth.2137 pmid:22886093; PubMed Central PMCID: PMC3433648.

Sedegah M, Charoenvit Y, Aguiar J, Sacci J, Hedstrom R, Kumar S, et al. Effect on antibody and T-cell responses of mixing five GMP-produced DNA plasmids and administration with plasmid expressing GM-CSF. Genes and immunity. 2004; 5(7):553-61. Epub 2004 Aug. 20. doi: 10.1038/sj.gene.6364125 pmid:15318164.

Sedegah M, Hedstrom R, Hobart P, Hoffman SL. Protection against malaria by immunization with plasmid DNA encoding circumsporozoite protein. Proceedings of the National Academy of Sciences of the United States of America. 1994; 91(21):9866-70. Epub 1994/10/11. pmid:7937907; PubMed Central PMCID: PMC44918. doi: 10.1073/pnas.91.21.9866

Sedegah M, Hollingdale M R, Farooq F, Ganeshan H, Belmonte M, Kim Y, et al. Sterile immunity to malaria after DNA prime/adenovirus boost immunization is associated with effector memory CD8+ T cells targeting AMA1 class I epitopes. PloS one. 2014; 9(9):e106241. Epub 2014 Sep. 12. doi: 10.1371/journal.pone.0106241 pmid:25211344; PubMed Central PMCID: PMC4161338.

Seder R A, Chang L J, Enama M E, Zephir K L, Sarwar U N, Gordon I J, et al. Protection against malaria by intravenous immunization with a nonreplicating sporozoite vaccine. Science. 2013; 341(6152):1359-65. Epub 2013 Aug. 10. doi: 10.1126/science.1241800 pmid:23929949.

Spring M, Murphy J, Nielsen R, Dowler M, Bennett J W, Zarling S, et al. First-in-human evaluation of genetically attenuated *Plasmodium* falciparum sporozoites administered by bite of Anopheles mosquitoes to adult volunteers. Vaccine. 2013; 31(43):4975-83. Epub 2013 Sep. 14. doi: 10.1016/j.vaccine.2013.08.007 pmid:24029408.

Stewart, M J et al., 1988. J Protozool 35:389.

Stoute J A, Slaoui M, Heppner D G, Momin P, Kester K E, Desmons P, et al. A preliminary evaluation of a recombinant circumsporozoite protein vaccine against *Plasmodium* falciparum malaria. RTS,S Malaria Vaccine Evaluation Group. The New England journal of medicine. 1997; 336(2):86-91. Epub 1997/01/09. doi: 10.1056/NEJM199701093360202 pmid:8988885.

Trofa, A. F., et al., Dengue fever in US military personnel in Haiti. JAMA, 1997. 277(19): p. 1546-8.

Tsuda, Y., et al., A cytomegalovirus-based vaccine provides long-lasting protection against lethal Ebola virus challenge after a single dose. Vaccine, 2015. 33(19): p. 2261-6.

Van Braeckel-Budimir N, Harty J. Highly focused TCR Vβ repertoire is associated with a large number of naive precursors and robust CD8 T cell responses specific for a *Plasmodium* antigen (IRM14P.450). The Journal of Immunology. 2015; 194(1 Supplement): 198.10.

Van Braeckel-Budimir N, Harty J T. CD8 T-cell-mediated protection against liver-stage malaria: lessons from a mouse model. Front Microbiol. 2014; 5:272. doi: 10.3389/fmicb.2014.00272 pmid:24936199; PubMed Central PMCID: PMC4047659.

Van Der Most, R G et al., 1996. J Immunol 157:5543.

Van Der Most, R G et al., 1998. Virology 240:158.

Vaughan A M, O'Neill M T, Tarun A S, Camargo N, Phuong T M, Aly A S, et al. Type II fatty acid synthesis is essential only for malaria parasite late liver stage development. Cell Microbiol. 2009; 11(3):506-20. doi: 10.1111/j.1462-5822.2008.01270.x pmid:19068099; PubMed Central PMCID: PMC2688669.

von Seidlein L, Bejon P. Malaria vaccines: past, present and future. Archives of disease in childhood. 2013; 98(12): 981-5. Epub 2013 Sep. 26. doi: 10.1136/archdischild-2013-304173 pmid:24061779.

Wang R, Arevalo-Herrera M, Gardner M J, Bonelo A, Carlton J M, Gomez A, et al. Immune responses to *Plasmodium* vivax pre-erythrocytic stage antigens in naturally exposed Duffy-negative humans: a potential model for identification of liver-stage antigens. European journal of immunology. 2005a; 35(6):1859-68. Epub 2005 May 3. doi: 10.1002/eji.200425807 pmid:15864779.

Wang R, Doolan D L, Charoenvit Y, Hedstrom R C, Gardner M J, Hobart P, et al. Simultaneous induction of multiple antigen-specific cytotoxic T lymphocytes in nonhuman primates by immunization with a mixture of four *Plasmodium* falciparum DNA plasmids. Infect Immun. 1998b; 66(9):4193-202. Epub 1998 Aug. 26. pmid:9712767; PubMed Central PMCID: PMC108505.

Wang R, Doolan D L, Le T P, Hedstrom R C, Coonan K M, Charoenvit Y, et al. Induction of antigen-specific cytotoxic T lymphocytes in humans by a malaria DNA vaccine. Science. 1998a; 282(5388):476-80. Epub 1998 Oct. 17. pmid:9774275. doi: 10.1126/science.282.5388.476

Wang R, Richie T L, Baraceros M F, Rahardjo N, Gay T, Banania J G, et al. Boosting of DNA vaccine-elicited gamma interferon responses in humans by exposure to malaria parasites. Infect Immun. 2005b; 73(5):2863-72. Epub 2005 Apr. 23. doi: 10.1128/IAI.73.5.2863-2872.2005 pmid:15845492; PubMed Central PMCID: PMC1087336.

Warfield, K. L., et al., Development and characterization of a mouse model for Marburg hemorrhagic fever. J Virol, 2009. 83(13): p. 6404-15.

Weiss W R, Jiang C G. Protective CD8+ T lymphocytes in primates immunized with malaria sporozoites. PloS one. 2012; 7(2):e31247. Epub 2012 Feb. 23. doi: 10.1371/journal.pone.0031247 pmid:22355349; PubMed Central PMCID: PMC3280278.

Weiss W R, Mellouk S, Houghten R A, Sedegah M, Kumar S, Good M F, et al. Cytotoxic T cells recognize a peptide from the circumsporozoite protein on malaria-infected hepatocytes. The Journal of experimental medicine. 1990; 171(3):763-73. Epub 1990 Mar. 1. pmid:1689762; PubMed Central PMCID: PMC2187765. doi: 10.1084/jem.171.3.763 WHO Global Malaria Programme. World Malaria Report 2014. Geneva: World Health Organization, 2014.

Wick, D. A., et al., Profound CD8+ T cell immunity elicited by sequential daily immunization with exogenous antigen plus the TLR3 agonist poly(I:C). Vaccine, 2011. 29(5): p. 984-93.

Williams, J A, 2014. Curr Gene Ther 14:170.

Yager, E. J., et al., Particle-mediated DNA vaccines against seasonal and pandemic influenza viruses elicit strong mucosal antibody and T cell responses in the lung. Procedia in Vaccinology, 2010. 3: p. 2-11.

Zhang Y, Werling U, Edelmann W. Seamless Ligation Cloning Extract (SLiCE) cloning method. Methods in molecular biology. 2014; 1116:235-44. doi: 10.1007/978-1-62703-764-8_16 pmid:24395368.

Zhu J, Hollingdale M R. Structure of *Plasmodium* falciparum liver stage antigen-1. Molecular and biochemical parasitology. 1991; 48(2):223-6. Epub 1991 Oct. 1. pmid: 1840628. doi: 10.1016/0166-6851(91)90117-o

What is claimed is:

1. An immunogenic composition comprising:
   two or more plasmid pools, including a first plasmid pool and a second plasmid pool;
   where at least the first plasmid pool is loaded onto a first delivery medium and where at least the second plasmid pool is loaded onto a second delivery medium;
   where the first and the second delivery media are loaded into a dosing container;
   where the first plasmid pool comprises a first plurality of plasmids and where the second plasmid pool comprises a second plurality of plasmids different from the first plurality of plasmids;
   where each plasmid in the two or more plasmid pools contains one or more nucleic-acid sequences encoding a protein, or proteins, or a protein fragment;
   where the first and the second delivery media comprise particles, each smaller than the size of the cell receiving the particle, or micro-needles; and
   where at least the first and the second plasmid pools in the dosing container together contain more than one of the nucleic-acid sequences.

2. The immunogenic composition of claim 1 where the particles or micro-needles are gold.

3. The immunogenic composition of claim 1 where the number of plasmid pools is three or more.

4. The immunogenic composition of claim 1 where each of the plasmid pools encodes for a different set of proteins or protein fragments.

5. An immunogenic composition comprising:
   two or more nucleic-acid pools, including a first nucleic-acid pool and a second nucleic-acid pool;
   where at least the first nucleic-acid pool is loaded onto a first delivery medium and where at least the second nucleic-acid pool is loaded onto a second delivery medium;
   where the first and the second delivery media are loaded into a dosing container;
   where the first nucleic-acid pool comprises a first plurality of nucleic-acid fragments and where the second nucleic-acid pool comprises a second plurality of nucleic-acid fragments different from the first plurality of nucleic-acid fragments;
   where each nucleic-acid fragment in the two or more nucleic-acid pools contains one or more nucleic-acid sequences encoding a protein, or proteins, or a protein fragment;
   where the first and the second delivery media comprise particles, each smaller than the size of the cell receiving the particle, or micro-needles;
   where at least the first and the second nucleic-acid pools in the dosing container together contain more than one of the nucleic-acid sequences.

6. The immunogenic composition of claim 5 where the particles or micro-needles are gold.

7. The immunogenic composition of claim 5 where the number of nucleic-acid pools is three or more.

8. The immunogenic composition of claim 5 where each of the nucleic-acid pools encodes for a different set of proteins or protein fragments.

9. A method of eliciting an immune response in a subject comprising administering the immunogenic composition of claim 1 to the subject to treat a disease or condition, wherein the disease or condition is caused by one or more of an infectious pathogen, by a malignancy, by an autoimmune disease, or by transplantation.

10. The method of claim 9, wherein the disease or condition is malaria.

11. A method of eliciting an immune response in a subject comprising administering the immunogenic composition of claim 5 to the subject to treat disease or condition, wherein the disease or condition is caused by one or more of an infectious pathogen, by a malignancy, by an autoimmune disease, or by transplantation.

12. The method of claim 11, wherein the disease or condition is malaria.

13. A method of screening candidate antigens or epitopes associated with a disease or condition comprising:
    exposing one or more subjects to the immunogenic composition of claim 1;
    analyzing one or more biological samples obtained from the one or more subjects using an assay to measure the response to the immunogenic composition; and
    identifying a nucleic acid fragment that is part of the immunogenic composition as encoding a candidate antigen or epitope when the nucleic acid fragment elicits a response measured by the assay in the one or more biological samples.

14. A method of screening candidate antigens or epitopes associated with a disease or condition comprising:
    exposing one or more subjects to the immunogenic composition of claim 5;
    analyzing one or more biological samples obtained from the one or more subjects using an assay to measure the response to the immunogenic composition; and
    identifying a nucleic acid fragment that is part of the immunogenic composition as encoding a candidate antigen or epitope when the nucleic acid fragment elicits a response measured by the assay in the one or more biological samples.

* * * * *

UNITED STATES PATENT AND TRADEMARK OFFICE
CERTIFICATE OF CORRECTION

PATENT NO. : 10,925,950 B2
APPLICATION NO. : 15/749928
DATED : February 23, 2021
INVENTOR(S) : Sean C. Murphy et al.

Page 1 of 1

It is certified that error appears in the above-identified patent and that said Letters Patent is hereby corrected as shown below:

In the Claims

Claim 11, Column 50 Line 22, before "disease or condition" insert --a--.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*